(12) United States Patent  
Carlson et al.

(10) Patent No.: US 8,391,957 B2
(45) Date of Patent: Mar. 5, 2013

(54) ROBOTIC CATHETER SYSTEMS AND METHODS

(75) Inventors: Christopher R. Carlson, Menlo Park, CA (US); Federico Barbagli, San Francisco, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1375 days.

(21) Appl. No.: 12/079,500

(22) Filed: Mar. 26, 2008

(65) Prior Publication Data
US 2008/0255505 A1 Oct. 16, 2008

Related U.S. Application Data

(60) Provisional application No. 60/920,328, filed on Mar. 26, 2007.

(51) Int. Cl.
*A61B 5/05* (2006.01)
(52) U.S. Cl. ...................... 600/429; 604/95.04
(58) Field of Classification Search ............... 604/95.04; 600/310, 407, 411, 417, 425, 427, 429
See application file for complete search history.

(56) References Cited

U.S. PATENT DOCUMENTS

| | | |
|---|---|---|
| 2002/0087048 A1 | 7/2002 | Brock et al. |
| 2004/0193146 A1 | 9/2004 | Lee et al. |
| 2005/0137478 A1 | 6/2005 | Younge et al. |
| 2005/0197530 A1 | 9/2005 | Wallace et al. |
| 2005/0222554 A1 | 10/2005 | Wallace et al. |
| 2006/0057560 A1 | 3/2006 | Hlavka et al. |
| 2006/0084945 A1 | 4/2006 | Moll et al. |
| 2006/0095022 A1 | 5/2006 | Moll et al. |
| 2006/0100610 A1 | 5/2006 | Wallace et al. |
| 2006/0111692 A1 | 5/2006 | Hlavka et al. |
| 2006/0200026 A1 | 9/2006 | Wallace et al. |
| 2006/0253108 A1 | 11/2006 | Yu et al. |
| 2006/0276775 A1 | 12/2006 | Rosenberg et al. |
| 2007/0043338 A1 | 2/2007 | Moll et al. |
| 2007/0156123 A1 | 7/2007 | Moll et al. |
| 2007/0197896 A1 * | 8/2007 | Moll et al. ................ 600/407 |
| 2007/0197939 A1 | 8/2007 | Wallace et al. |

OTHER PUBLICATIONS

PCT Invitation to pay additional fees and Partial Search Report for PCT/US2008/003997 of the International Searching Authority, Applicant Hansen Medical, Inc., Form PCT/ISA/206 and Annex to Form PCT/ISA/206, mailed Nov. 7, 2008 (6 pages).
PCT International Search Report and Written Opinion for PCT/US2008/003997, Applicant Hansen Medical, Inc., Form PCT/ISA/210, 220 and 237, mailed Mar. 12, 2009 (17 pages).

* cited by examiner

Primary Examiner — Melanie Hand
(74) Attorney, Agent, or Firm — Vista IP Law Group LLP

(57) ABSTRACT

A robotic instrument system having an elongate sheath instrument and an elongate catheter instrument positioned within a working lumen of the sheath instrument is controlled by selectively operating an instrument driver coupled to the catheter instrument to place a control element extending through the catheter instrument in tension, and thereby articulate at least a distal end portion the catheter instrument, while automatically compensating for a torsional force exerted on the sheath instrument in a first direction due to articulation of the distal end portion of the catheter, by urging the sheath instrument to twist in a second direction opposite of the first direction.

12 Claims, 54 Drawing Sheets

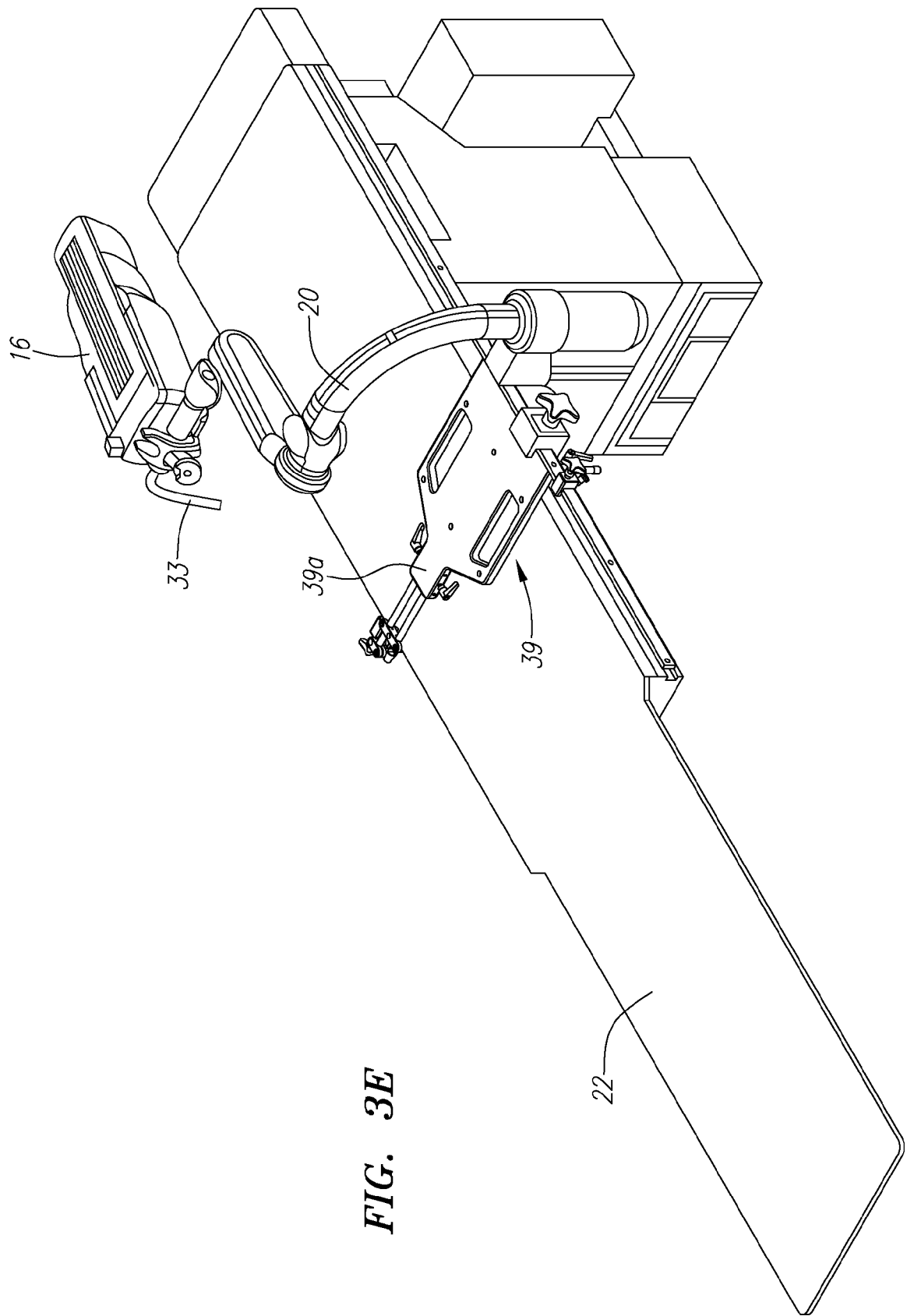

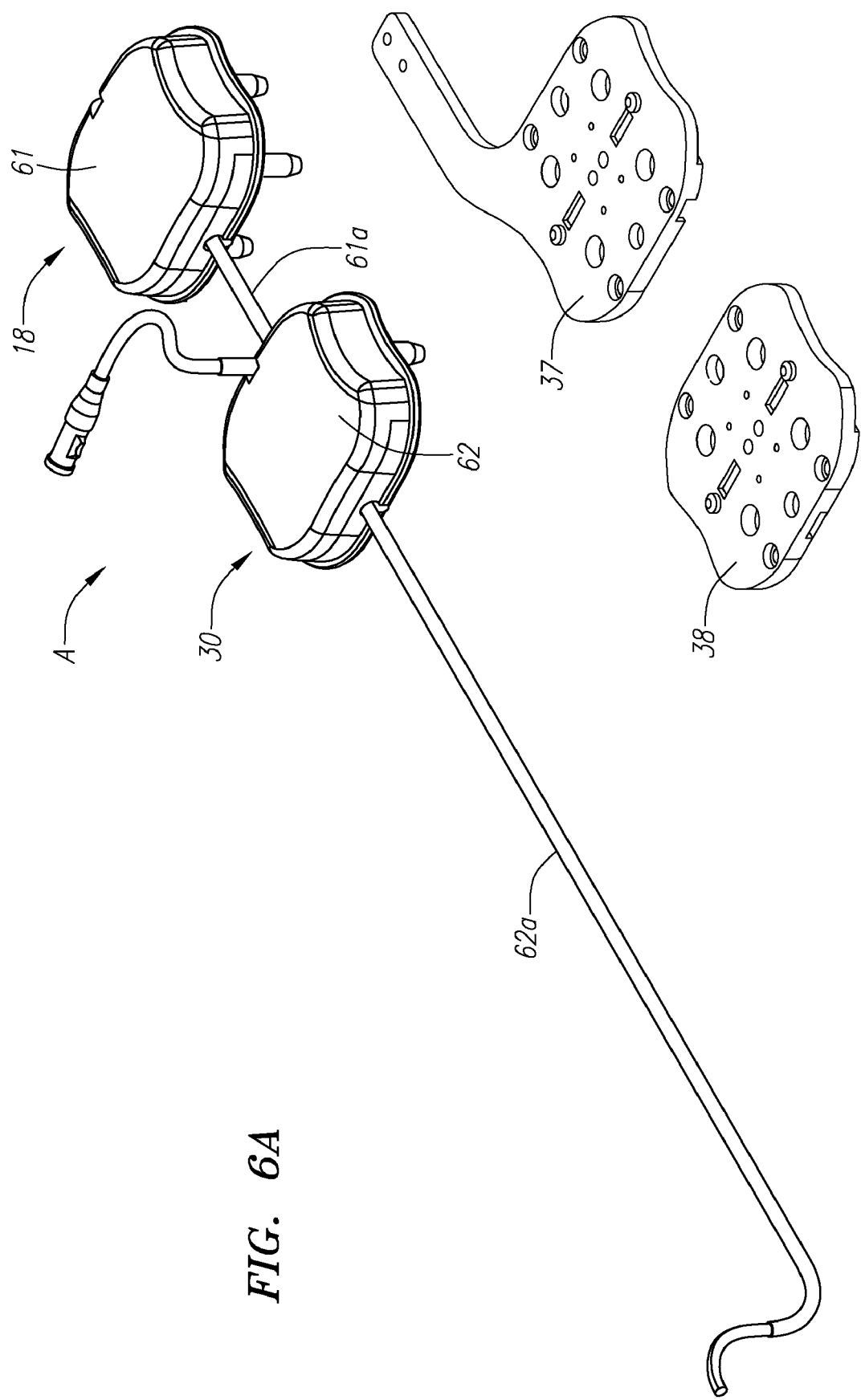

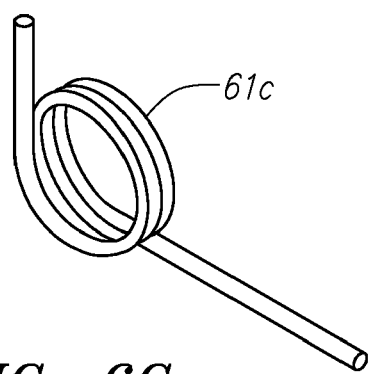
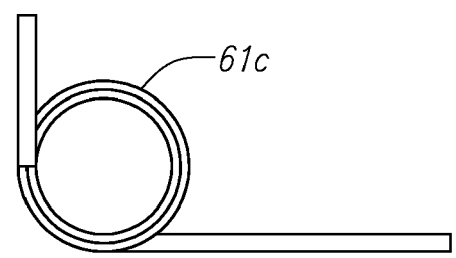
FIG. 6G  FIG. 6H
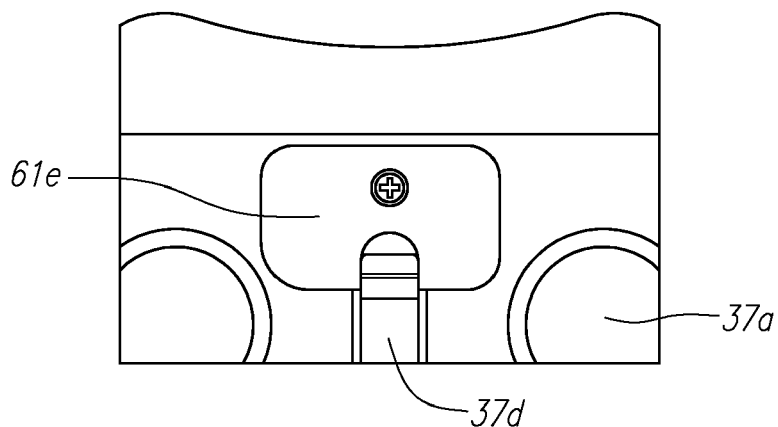
FIG. 6I
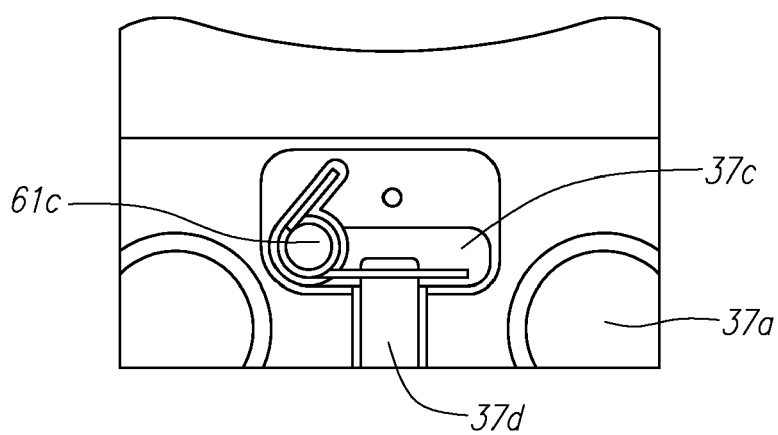
FIG. 6J

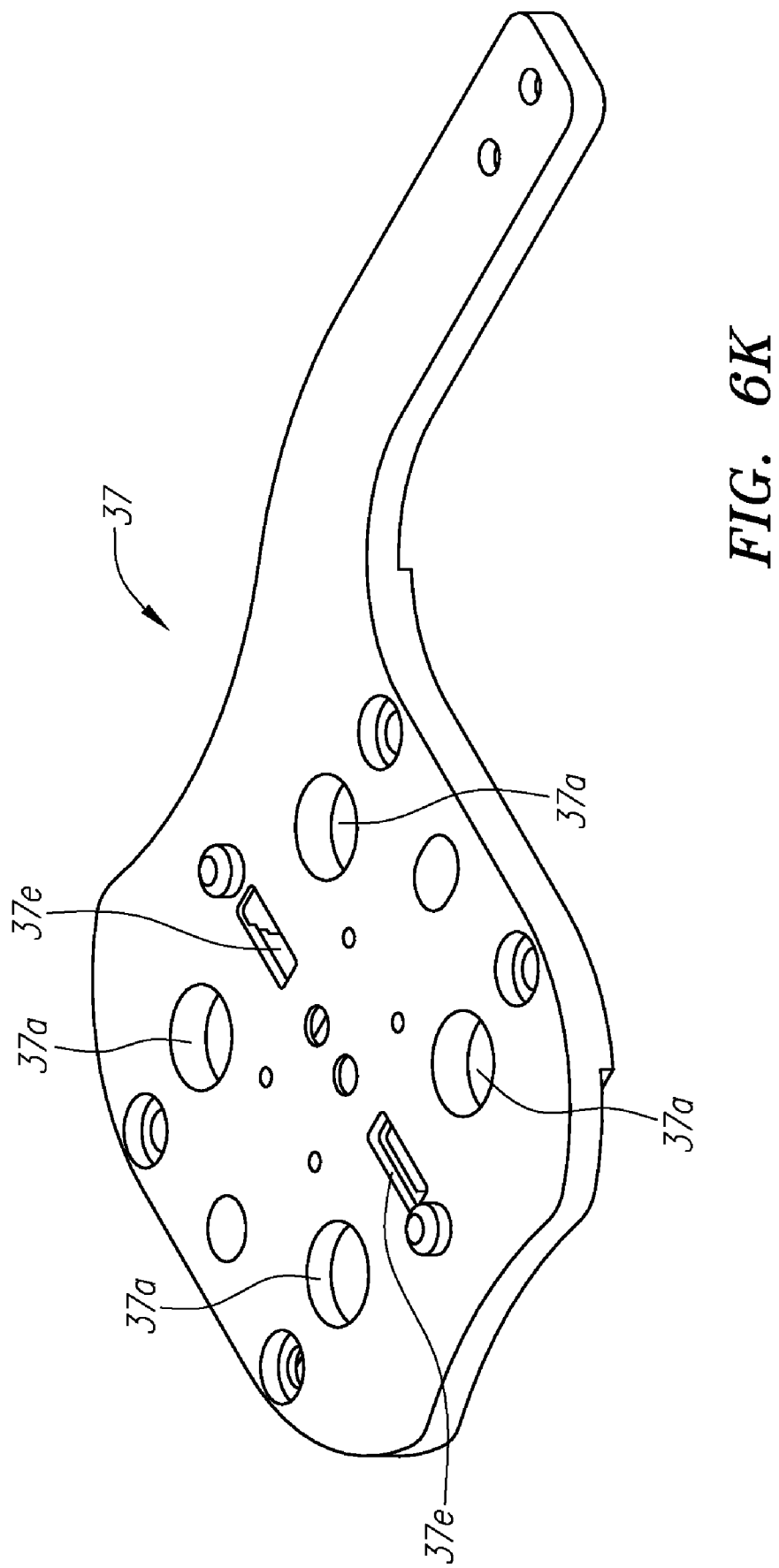

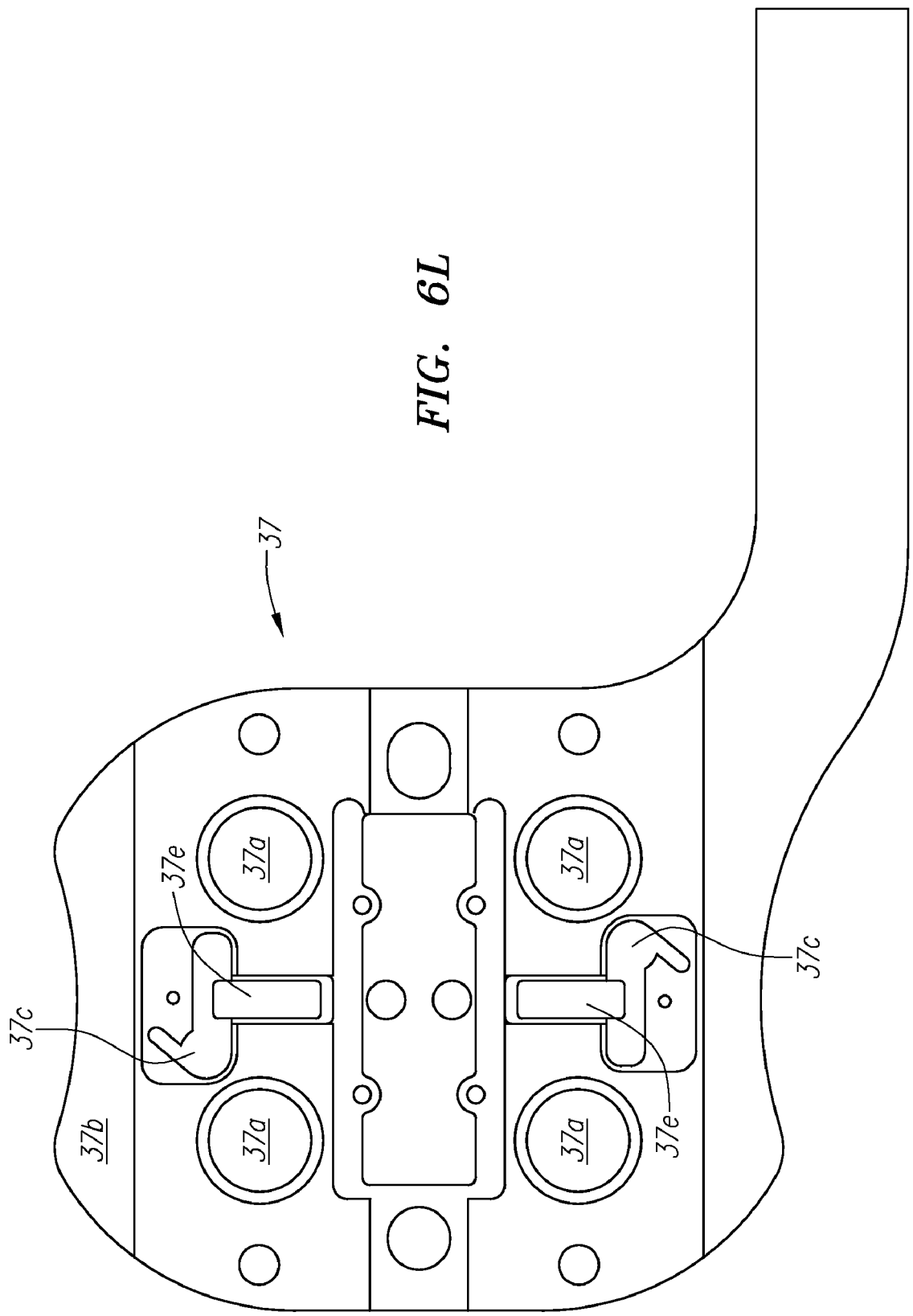

ROBOTIC CATHETER SYSTEMS AND METHODS

CROSS-REFERENCE TO RELATED APPLICATION

The present application claims the benefit under 35 U.S.C. §119 to U.S. Provisional Application No. 60/920,328, filed Mar. 26, 2007, the contents of which are incorporated herein by reference as though set forth in full.

The present application may also be related to subject matter disclosed in the following applications and patents, the contents of which are also incorporated herein by reference as though set forth in full: U.S. patent application Ser. No. 10/923,660, filed Aug. 20, 2004; U.S. patent application Ser. No. 10/949,032, filed Sep. 24, 2005; U.S. patent application Ser. No. 11/073,363, filed Mar. 4, 2005; U.S. patent application Ser. No. 11/173,812, filed Jul. 1, 2005; U.S. patent application Ser. No. 11/176,954, filed Jul. 6, 2005; U.S. patent application Ser. No. 11/179,007, filed Jul. 6, 2005; U.S. patent application Ser. No. 11/185,432, filed Jul. 19, 2005; U.S. patent application Ser. No. 11/202,925, filed Aug. 12, 2005; U.S. Provisional Patent Application No. 60/750,590, filed Dec. 14, 2005; U.S. Provisional Patent Application No. 60/756,136, filed Jan. 3, 2006; U.S. patent application Ser. No. 11/331,576, filed Jan. 13, 2006; U.S. Provisional Patent Application No. 60/776,065, filed Feb. 22, 2006; U.S. Provisional Patent Application No. 60/785,001, filed Mar. 22, 2006; U.S. Provisional Patent Application No. 60/788,176, filed Mar. 31, 2006; U.S. patent application Ser. No. 11/418,398, filed May 3, 2006; U.S. Provisional Patent Application No. 60/801,355, filed May 17, 2006; U.S. Provisional Patent Application No. 60/801,546, filed May 17, 2006; U.S. Provisional Patent Application No. 60/801,945, filed May 18, 2006; U.S. patent application Ser. No. 11/481,433, filed Jul. 3, 2006; U.S. Provisional Patent Application No. 60/833,624, filed Jul. 26, 2006; U.S. Provisional Patent Application No. 60/835,592, filed Aug. 3, 2006; U.S. Provisional Patent Application No. 60/838,075, filed Aug. 15, 2006; U.S. Provisional Patent Application No. 60/840,331, filed Aug. 24, 2006; U.S. Provisional Patent Application No. 60/843,274, filed Sep. 8, 2006; U.S. Provisional Patent Application No. 60/873,901, filed Dec. 8, 2006; U.S. patent application Ser. No. 11/637,951, filed Dec. 11, 2006; U.S. patent application Ser. No. 11/640,099, filed Dec. 14, 2006; U.S. Provisional Patent Application No. 60/879,911, filed Jan. 10, 2007; U.S. Provisional Patent Application No. 60/899,048, filed Feb. 1, 2007; U.S. Provisional Patent Application No. 60/900,584, filed Feb. 8, 2007; U.S. Provisional Patent Application No. 60/902,144, filed Feb. 15, 2007; and U.S. patent application Ser. No. 11/678,016, filed Feb. 22, 2007.

FIELD OF THE INVENTION

The invention relates generally to robotically controlled systems, such as tele-robotic surgical systems, and more particularly, to a robotic catheter system for performing minimally invasive diagnostic and therapeutic procedures.

BACKGROUND

Robotic interventional systems and devices are well suited for performing minimally invasive medical procedures as opposed to conventional techniques wherein the patient's body cavity is open to permit the surgeon's hands access to internal organs. Traditionally, surgery utilizing conventional procedures meant significant pain, long recovery times, lengthy work absences, and visible scarring. However, advances in technology have lead to significant changes in the field of medical surgery such that less invasive surgical procedures, in particular, minimally invasive surgery (MIS), are increasingly popular.

A "minimally invasive medical procedure" is generally defined as a procedure that is performed by entering the body through the skin, a body cavity, or an anatomical opening utilizing small incisions rather than large, open incisions in the body. Various medical procedures are considered to be minimally invasive including, for example, mitral and tricuspid valve procedures, patent formen ovale, atrial septal defect surgery, colon and rectal surgery, laparoscopic appendectomy, laparoscopic esophagectomy, laparoscopic hysterectomies, carotid angioplasty, vertebroplasty, endoscopic sinus surgery, thoracic surgery, donor nephrectomy, hypodermic injection, air-pressure injection, subdermal implants, endoscopy, percutaneous surgery, laparoscopic surgery, arthroscopic surgery, cryosurgery, microsurgery, biopsies, videoscope procedures, keyhole surgery, endovascular surgery, coronary catheterization, permanent spinal and brain electrodes, stereotactic surgery, and radioactivity-based medical imaging methods. With MIS, it is possible to achieve less operative trauma for the patient, reduced hospitalization time, less pain and scarring, reduced incidence of complications related to surgical trauma, lower costs, and a speedier recovery.

Special medical equipment may be used to perform MIS procedures. Typically, a surgeon inserts small tubes or ports into a patient and uses endoscopes or laparoscopes having a fiber optic camera, light source, or miniaturized surgical instruments. Without a traditional large and invasive incision, the surgeon is not able to see directly into the patient. Thus, the video camera serves as the surgeon's eyes. The images of the interior of the body are transmitted to an external video monitor to allow a surgeon to analyze the images, make a diagnosis, visually identify internal features, and perform surgical procedures based on the images presented on the monitor.

MIS procedures may involve minor surgery as well as more complex operations that involve robotic and computer technologies, which may be used during more complex surgical procedures and have led to improved visual magnification, electromechanical stabilization, and reduced number of incisions. The integration of robotic technologies with surgeon skill into surgical robotics enables surgeons to perform surgical procedures in new and more effective ways.

Although MIS techniques have advanced, physical limitations of certain types of medical equipment still have shortcomings and can be improved. While known devices may have been used effectively, they may lack the required or desired degrees of freedom and range of controllable motion. These issues may be particularly relevant in procedures involving routing of surgical devices around a number of turns or bends. Consequently, control of a tool or working instrument at the distal tip of an instrument that has traversed a number of curves may be difficult with known devices, thereby resulting in more complicated and/or less effective procedures.

SUMMARY

In accordance with a first aspect of the inventions disclosed herein, a robotic instrument system having an elongate sheath instrument and an elongate catheter instrument positioned within a working lumen of the sheath instrument is controlled by selectively operating an instrument driver coupled to the catheter instrument to place a control element extending through the catheter instrument in tension, and thereby articulate at least a distal end portion the catheter instrument, while automatically compensating for a torsional force exerted on the sheath instrument in a first direction due to articulation of the distal end portion of the catheter, by urging the sheath instrument to twist in a second direction opposite of the first direction. Compensating for the torsional force may be performed when the catheter instrument is bent in a first plane and the sheath instrument is bent in a second plane different than the first plane. The sheath instrument may be urged to twist by operating the instrument driver to place a control element of the sheath instrument in tension. Additionally, the sheath instrument may define a first axis and is bent to define a second axis, and the catheter instrument is bent to define a third axis, wherein compensating for the torsional force is based on: $\beta=K \sin(\theta)\sin(\alpha)$, wherein $\beta$=compensation of the rotational position of the catheter instrument within the sheath instrument, $\alpha$=an angle defined between the first axis and the second axis, $\theta$=an angle defined between the second axis and the third axis, K=a tuning gain factor.

In accordance with a second aspect of the inventions disclosed herein, a robotic instrument system having an elongate flexible sheath instrument and an elongate flexible catheter instrument positioned within a working lumen of the sheath instrument has a controller configured to determine a length of a distal end portion of the catheter instrument that extends beyond a distal end opening of the sheath instrument, and then selectively actuate one or more motors in an instrument driver coupled to the respective sheath and catheter instruments to thereby cause articulation of a distal end portion of the catheter instrument extending through a distal end opening of the sheath instrument, wherein actuation of the motors is based at least in part on the determined length so that the resulting articulation of the distal end portion of the catheter instrument is scaled.

In one embodiment, articulation of the distal end portion of the catheter instrument may be scaled based on a filtered curvature relationship, $KF=a*KC$ wherein $KF$=a filtered or adjusted position or curvature of the catheter instrument, $KC$=the commanded position or curvature of the catheter instrument, and "a"=a scaling factor. Also, the scaling factor "a" may be a non-linear function. The non-linear function is a function of the length "l" of the catheter instrument that extends beyond the distal end of the sheath instrument, based on the expression:

$$a(l) = 1 - \frac{1-b}{1+\frac{l^c}{d}}$$

wherein "b", "c", and "d" are tuning factors for shaping the non-linear function.

Further, the scaling may be a minimum for maximum compensation of articulation of the catheter instrument when the catheter instrument is fully retracted within the sheath instrument.

In accordance with yet another aspect of the disclosed inventions, a robotic instrument system includes an elongate flexible instrument; a controller configured to selectively actuate one or more motors operably coupled to the instrument to thereby selectively move a distal end portion of the instrument within an anatomical workspace in which the instrument is located; and an imaging device coupled the distal end portion of the instrument and configured to acquire images of tissue regions and structures located within in a field of view, wherein the controller is further configured to determine which tissue regions and structures within the anatomical workspace are locatable within the field of view of the imaging device based, at least in part, upon a present relative position of the instrument distal end portion. In one embodiment, the imaging device comprises an ICE catheter positioned in a working lumen of the instrument.

In one embodiment, the controller determines a reach of the instrument distal end portion and of the field of view of the imaging device within the based at least in part on a kinematic model of the instrument. Embodiments of the system may further comprise a display in communication with the controller, wherein the controller displays the determined reach of the field of view of the imaging device on the display, or wherein the controller displays the tissue regions and structures in the anatomical workspace determined to be within reach of the field of view of the imaging device on the display. In one such embodiment, the controller displays the tissue regions and structures in the anatomical workspace determined to be within reach of the field of view of the imaging device overlaying an image of the anatomic workspace, wherein the image of the anatomic workspace may be obtained from a model of the workspace, from an imaging system, or both.

Other and further embodiments and aspects will be apparent in view of the following detailed description read in conjunction with the figures.

BRIEF DESCRIPTION OF THE DRAWINGS

Referring now to the drawings in which like reference numbers represent corresponding parts throughout and in which:

FIG. 3E further illustrates how the adapter base plate assembly is utilized to attach a support assembly and instrument driver to an operating table or surgical bed;

FIG. 6A illustrates a sheath and guide catheter assembly positioned over respective mounting plates;

FIG. 6G is a perspective view of a torsion spring that can be positioned within a pocket or space defined by an interface plate for interfacing with a mating structure or notch of a splayer cover;

FIG. 6H is a side view of the torsion spring shown in FIG. 6G;

FIG. 6I illustrates an interface plate including a cover applied over a torsion spring;

FIG. 6J shows the cover shown in FIG. 6I removed to show the torsion spring;

FIG. 6K is a perspective view of an example of a guide catheter interface plate;

FIG. 6L is a top view of the interface plate shown in FIG. 6K;

DETAILED DESCRIPTION OF ILLUSTRATED EMBODIMENTS

Embodiments of the invention generally relate to apparatus, systems and methods for robotic surgical systems. Robotic surgical system in which embodiments of the invention may be implemented are described with reference to FIGS. 1-6T. Apparatus, system and method embodiments are described with reference to FIGS. 7A-13D. More particularly, embodiments directed to correcting or compensating for rolling or rotation of a guide catheter within a sheath as a result of the torsional compliance of a guide catheter within the sheath are described with reference to FIGS. 7A-G. Embodiments directed to compensating for catheter tip "hotness" variances in the control over the distal portion of the catheter tip depending on how far the tip extends beyond the distal end of the sheath are described with reference to FIGS. 8A-D. Hotness compensation embodiments may involve a model that accounts for roll compensation, manipulating sheath pull wires to counter torsional forces, scaling adjustments and/or utilizing a more rigid sheath. Embodiments directed to indicating catheter insertion forces as the catheter engages tissue or another object are described with reference to FIGS. 9A-G. Embodiments directed to using a two-dimensional (2D) input device, such as a mouse, for controlling 2-D or three-dimensional (3D) motion, e.g., position and/or orientation, of a guide catheter or other working instrument are described with reference to FIGS. 10A-B. Embodiments directed to determining reachability of catheter instrument and viewability or fields of view at different reachable locations are described with reference to FIG. 11. Embodiments directed to utilizing an optical light source such as a laser for purposes of performing depth indications or distances between an instrument and an object of interest are described with reference to FIGS. 12A-B. Embodiments related to stereovision utilized by robotic surgical systems are described with reference to FIGS. 13A-D.

Figure 1:
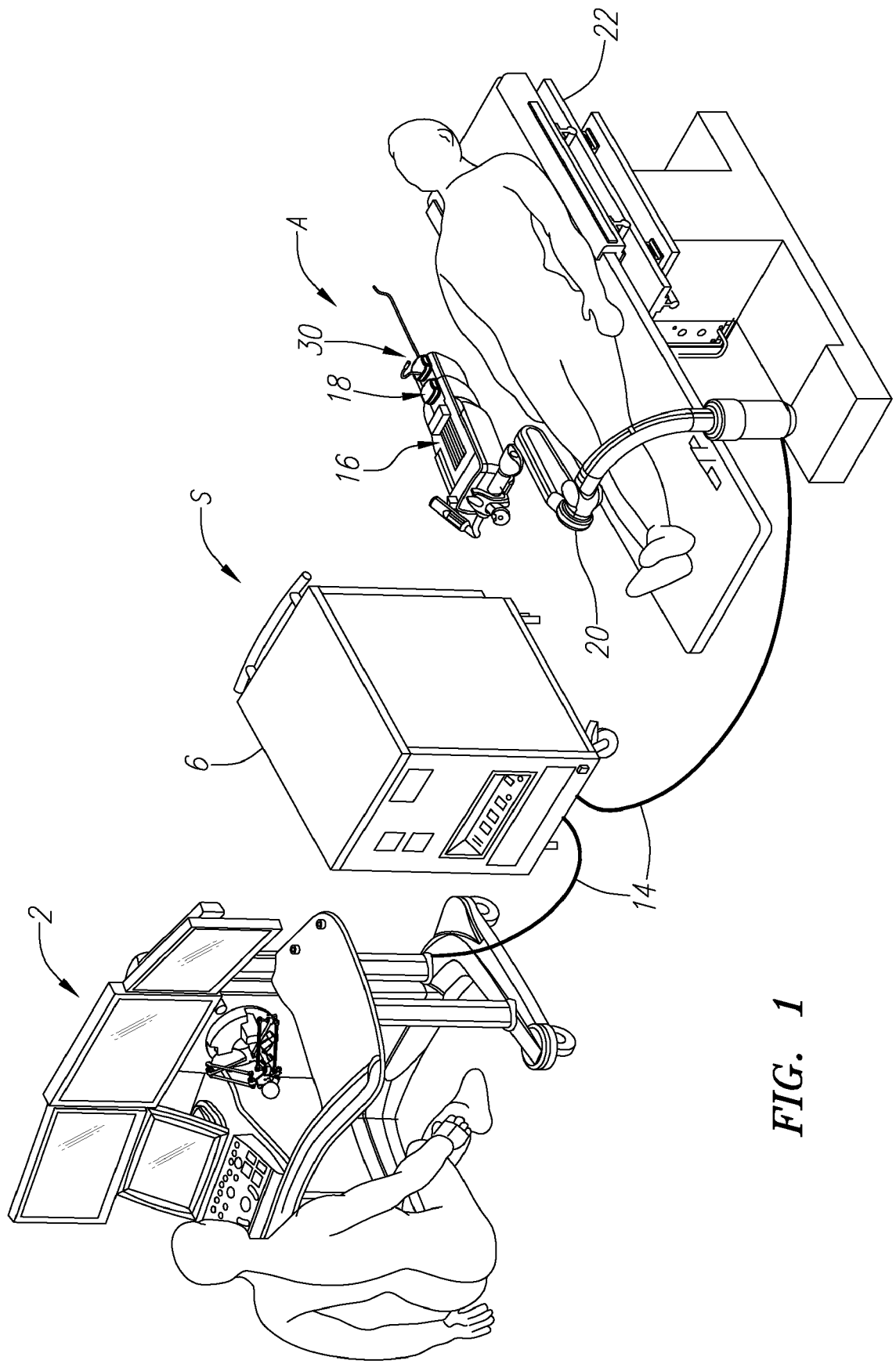
FIG. 1 illustrates a robotic surgical system in which apparatus, system and method embodiments may be implemented.

Referring to FIG. 1, a robotically controlled surgical system (S) in which apparatus, system and method embodiments of the invention may be implemented includes a robotic catheter assembly (A) having a robotic or first or outer steerable complement, otherwise referred to as a sheath instrument (30) (generally referred to as "sheath" or "sheath instrument") and/or a second or inner steerable component, otherwise referred to as a robotic catheter or guide or catheter instrument (18) (generally referred to as "catheter" or "catheter instrument"). The sheath instrument (30) and catheter instrument (30) are controllable using a robotic instrument driver (16) (generally referred to as "instrument driver"). During use, a patient is positioned on an operating table or surgical bed (22) (generally referred to as "operating table") to which a robotic catheter assembly (A) is coupled or mounted. In the illustrated example, the system (S) includes an operator workstation (2), an electronics rack (6) and associated bedside electronics box, a setup joint mounting brace (20), and the instrument driver (16). A surgeon is seated at the operator workstation (2) and can monitor the surgical procedure, patient vitals, and control one or more catheter devices.

Various system (S) components in which embodiments of the invention may be implemented are illustrated in close proximity to each other in FIG. 1, but embodiments may also be implemented in systems (S) in which components are separated from each other, e.g., located in separate rooms. For example, the instrument driver (16), operating table (22), and bedside electronics box may be located in the surgical area with the patient, and the operator workstation (2) and the electronics rack (6) may be located outside of the surgical area and behind a shielded partition. System (S) components may also communicate with other system (S) components via a network to allow for remote surgical procedures during which the surgeon may be located at a different location, e.g., in a different building or at a different hospital utilizing a communication link transfers signals between the operator control station (2) and the instrument driver (16). System (S) components may also be coupled together via a plurality of cables or other suitable connectors (14) to provide for data communication, or one or more components may be equipped with wireless communication components to reduce or eliminate cables (14). In this manner, a surgeon or other operator may control a surgical instrument while being located away from or remotely from radiation sources, thereby decreasing the operator's exposure to radiation.

Figure 2:
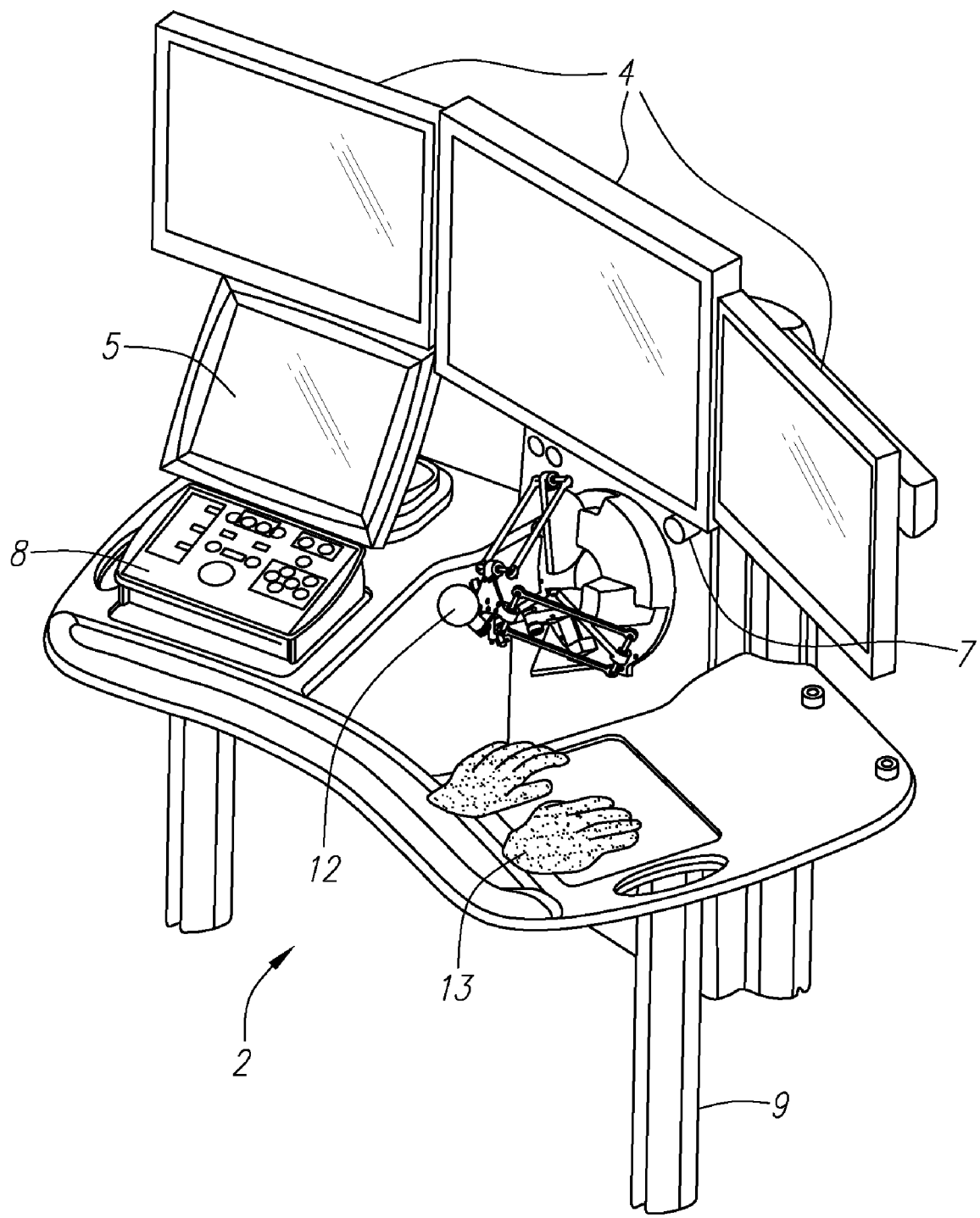
FIG. 2 illustrates an example of an operator workstation of the robotic surgical system shown in FIG. 1 with which a catheter instrument can be manipulated using different user interfaces and controls.

Referring to FIG. 2, one example of an operator workstation (2) that may be used with the system (S) shown in FIG. 1 includes three display screens (4), a touch screen user interface (5), a control button console or pendant (8), and a master input device (MID) (12). The MID (12) and data gloves (13) serve as user interfaces through which the surgeon can control operation of the instrument driver (16) and attached instruments. By manipulating the pendant (8) and the MID (12), a surgeon or other operator can cause the instrument driver (16) to remotely control a catheter instrument (18) and/or a sheath instrument (30) mounted thereon. A switch (7) may be provided to disable activity of an instrument temporarily. The console (9) in the illustrated system (S) may also be configurable to meet individual user preferences. For example, in the illustrated example, the pendant (8) and the touch screen (5) are shown on the left side of the console (9), but they may also be relocated to the right side of the console (9). Further, optional keyboard may be connected to the console (9) for inputting user data. The workstation (2) may also be mounted on a set of casters or wheels to allow easy movement of the workstation (2) from one location to another, e.g., within the operating room or catheter laboratory. Further aspects of examples of suitable MID (12), data glove (13), and workstation (2) arrangements are described in further detail in U.S. patent application Ser. No. 11/481,433 and U.S. Provisional Patent Application No. 60/840,331, the contents of which were previously incorporated herein by reference.

Figure 3A:
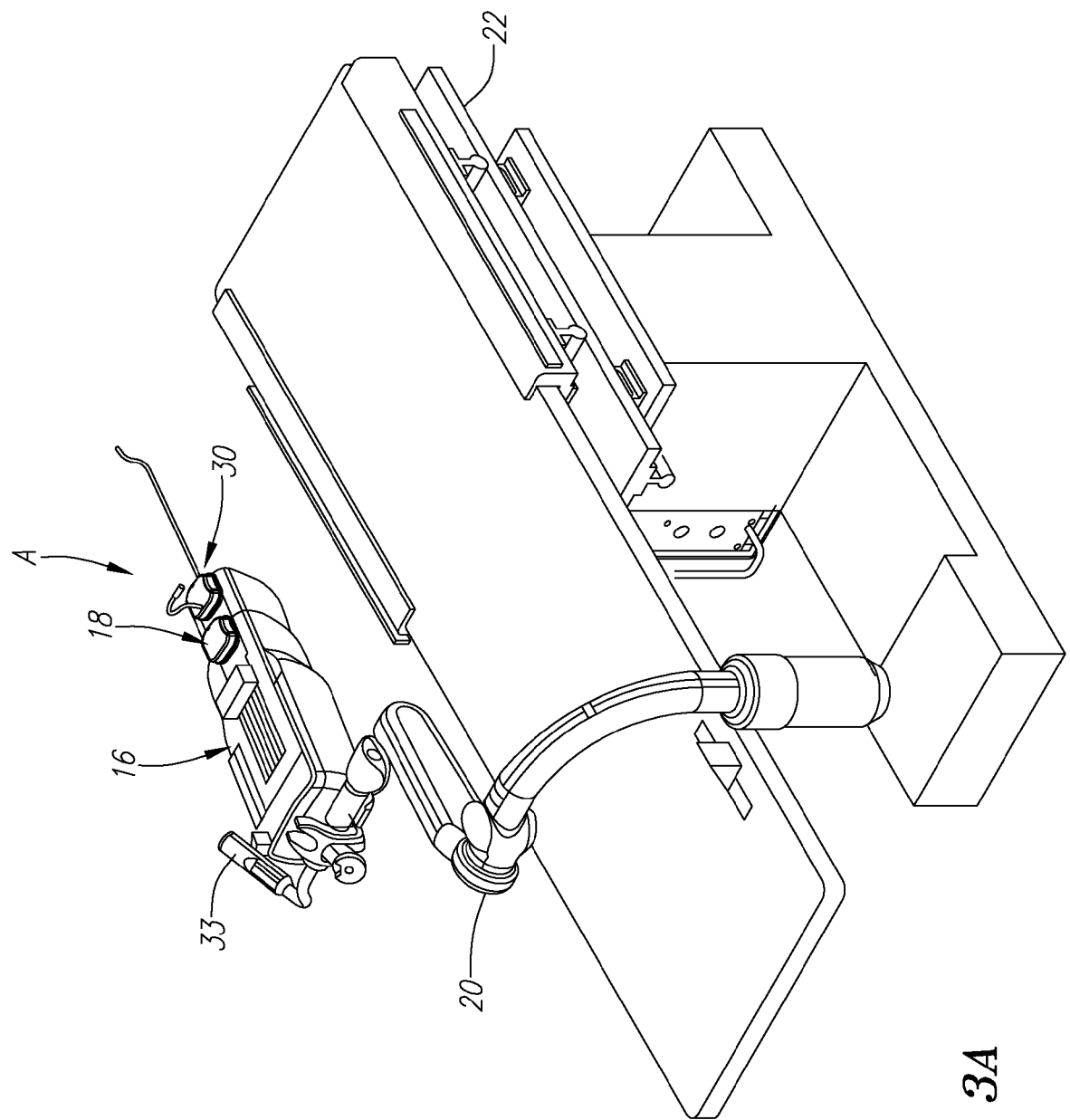
FIG. 3A illustrates a support assembly or mounting brace for a instrument driver of a robotic surgical system.
Figure 3B:
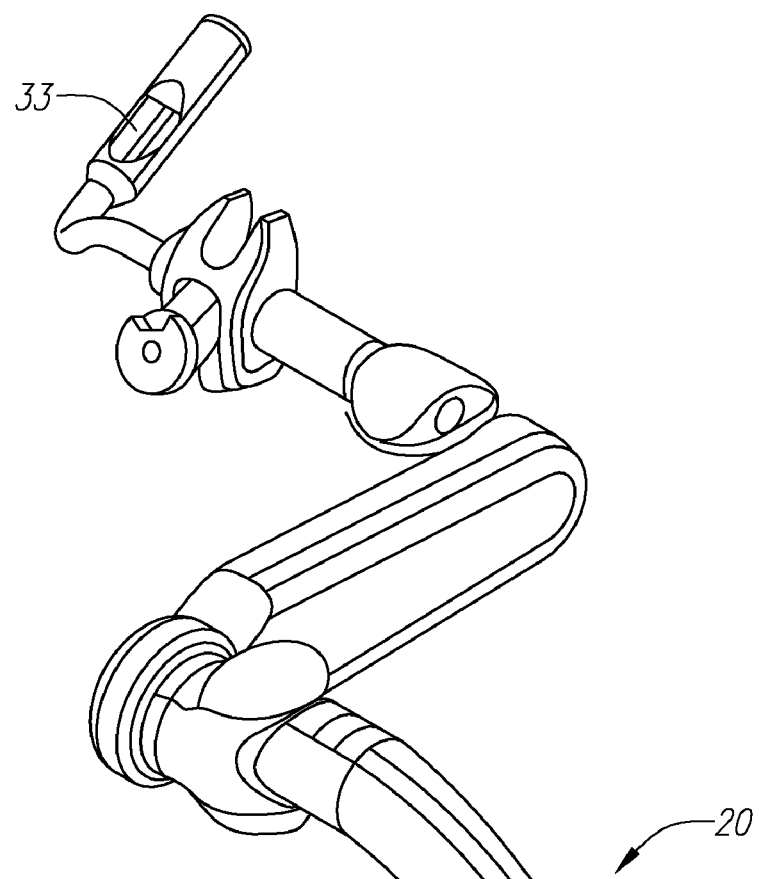
FIG. 3B further illustrates the support assembly illustrated in FIG. 3A.
Figure 3C:
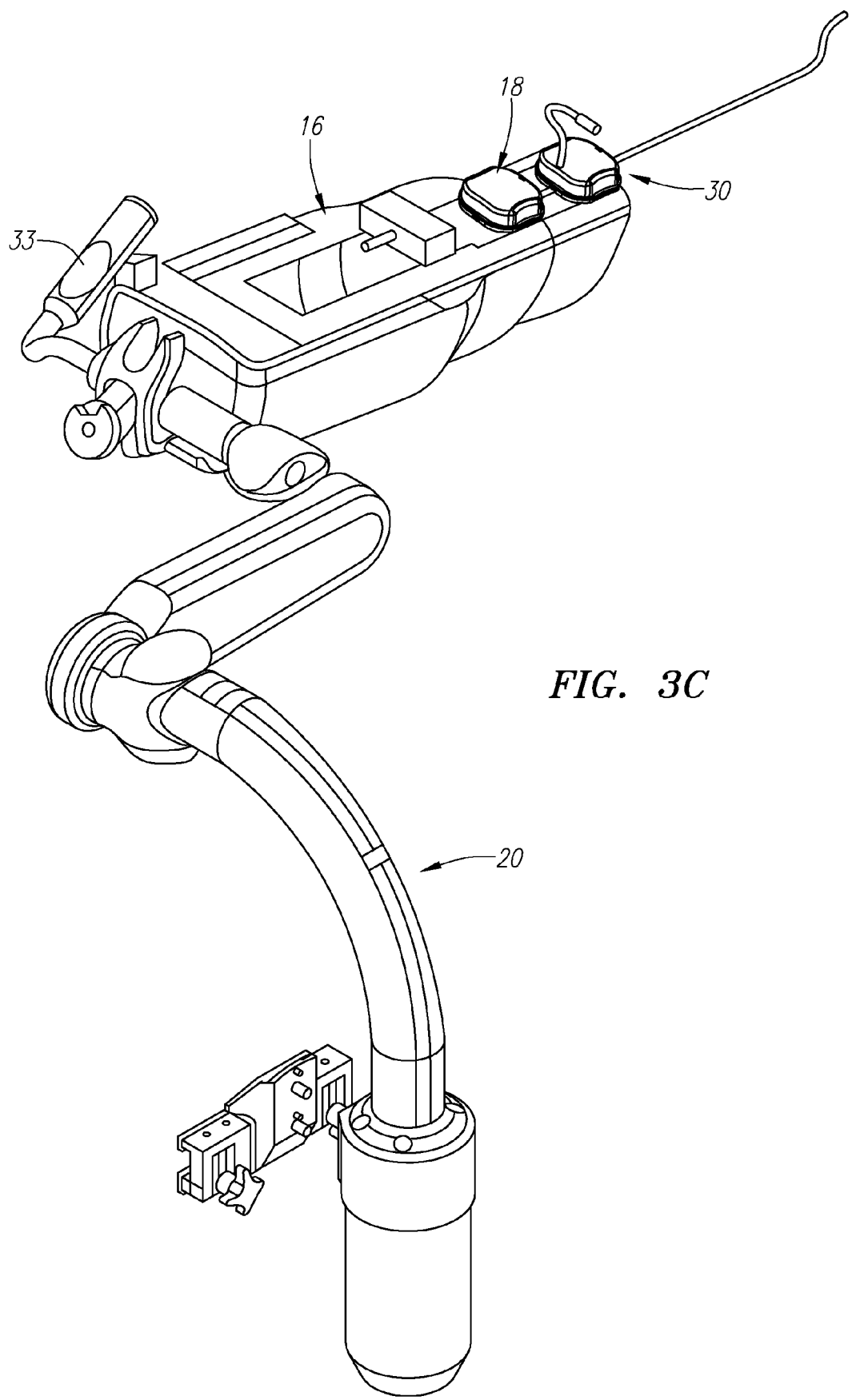
FIG. 3C is another view of the support assembly shown in FIGS. 3A-B with an attached instrument driver.

Referring to FIGS. 3A-C, a system (S) includes a setup joint or support assembly (20) (generally referred to as "support assembly") for supporting or carrying the instrument driver (16) over the operating table (22). One suitable support assembly (20) has an arcuate shape and is configured to position the instrument driver (16) above a patient lying on the table (22). The support assembly (20) may be configured to movably support the instrument driver (16) and to allow convenient access to a desired location relative to the patient. The support assembly (20) may also be configured to lock the instrument driver (16) into a certain position.

In the illustrated example, the support assembly (20) is mounted to an edge of the operating table (22) such that a catheter and sheath instruments (18, 30) mounted on the instrument driver (16) can be positioned for insertion into a patient. The instrument driver (16) is controllable to maneuver the catheter and/or sheath instruments (18, 30) within the patient during a surgical procedure. The distal portion of the setup joint (20) also includes a control lever (33) for maneuvering the setup joint (20).

Although the figures illustrate a single guide catheter (18) and sheath assembly (30) mounted on a single instrument driver (16), embodiments may be implemented in systems (S) having other configurations. For example, embodiments may be implemented in systems (S) that include a plurality of instrument drivers (16) on which a plurality of catheter/sheath instruments (18, 30) can be controlled. Further aspects of a suitable support assembly (20) are described in U.S. patent application Ser. No. 11/481,433 and U.S. Provisional Patent Application No. 60/879,911, the contents of which were previously incorporated herein by reference.

Figure 3D:
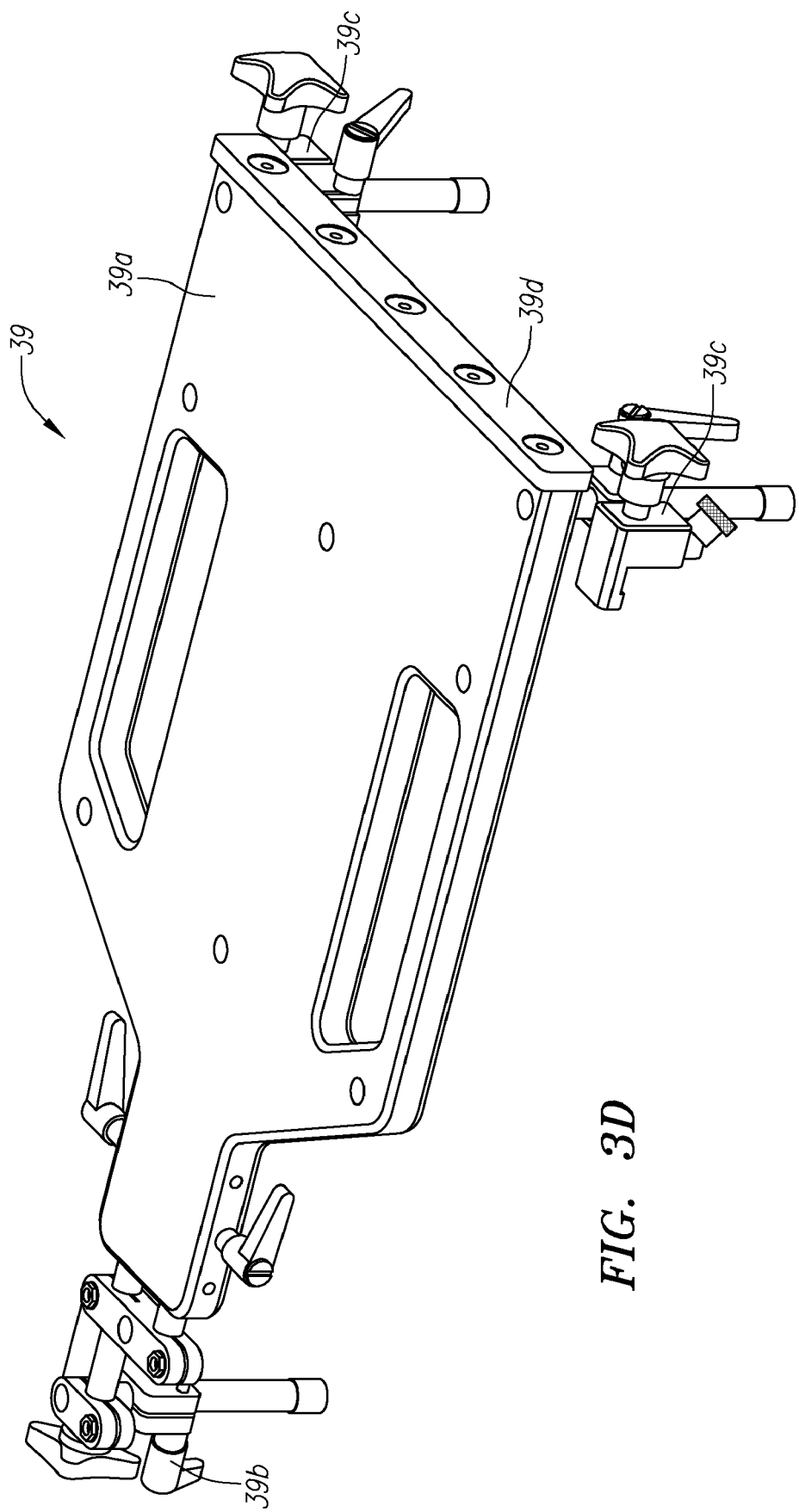
FIG. 3D is a perspective view of a support arm adapter base plate assembly configured for attaching a support assembly to an operating table or surgical bed.
Figure 4:
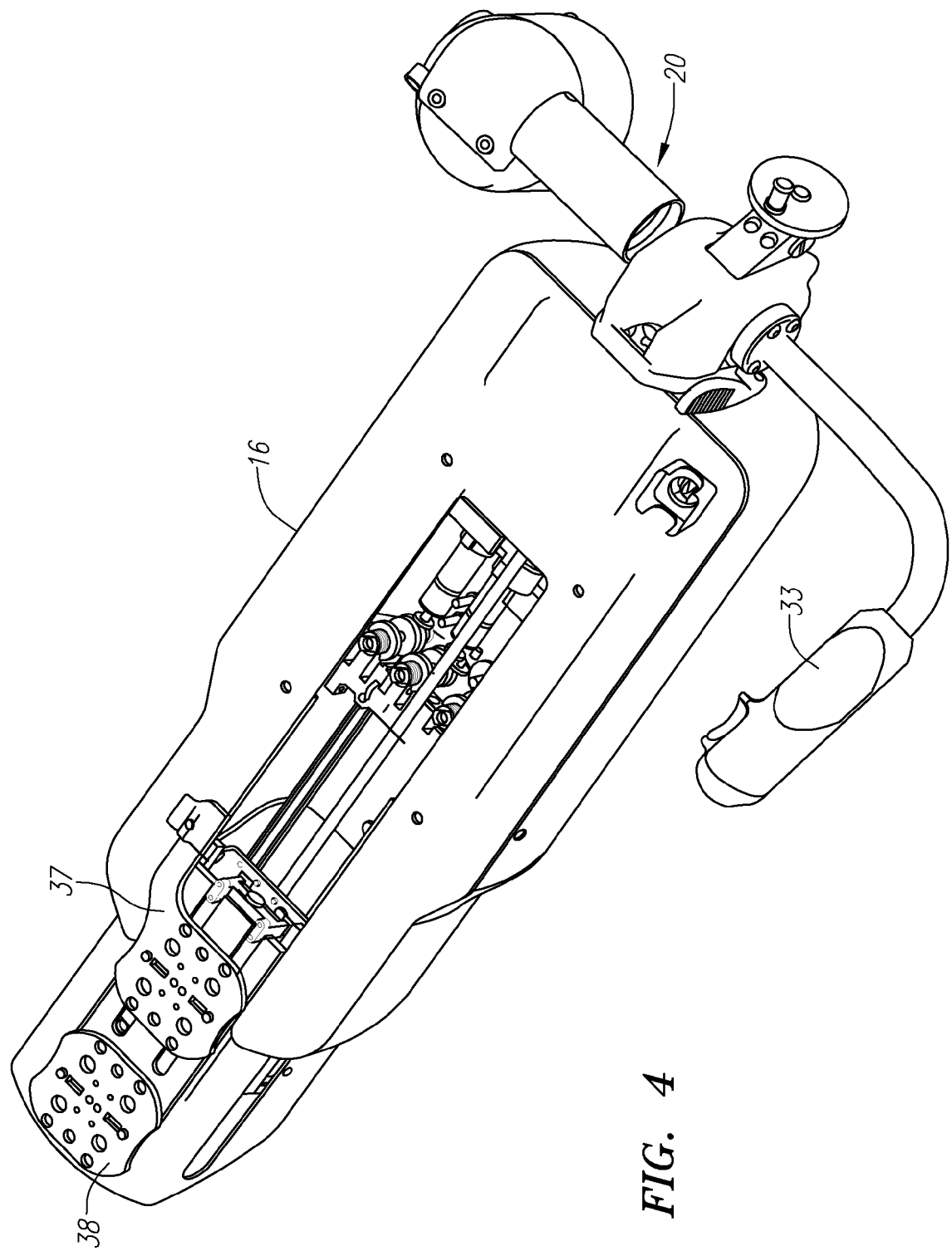
FIG. 4 illustrates an instrument driver mounted to a distal segment of a support assembly.

Referring to FIGS. 3D-E, the support assembly (20) may be mounted to an operating table (22) using a universal adapter base plate assembly (39), similar to those described in detail in U.S. Provisional Patent Application No. 60/899,048, incorporated by reference herein in its entirety. The adapter plate assembly (39) mounts directly to the operating table (22), and the support assembly (20) can be mounted to the adapter plate assembly (39). One suitable adapter plate assembly (39) includes a large, flat main plate (39a) which is positioned on top of the operating table (22). The assembly (39) provides for various adjustments to allow it to be mounted to different types of operating tables (22). An edge of the adapter plate assembly (39) may include a rail that mimics the construction of a traditional surgical bedrail. By placing this rail on the adapter plate (39a) itself, a user may be assured that the component dimensions provide for proper mounting of the support assembly (20). Furthermore, the large, flat surface of the main plate (39a) provides stability by distributing the weight of the support assembly (20) and instrument driver (16) over an area of the table (22), whereas a support assembly (20) mounted directly to the operating table (22) rail may cause its entire load to be placed on a limited and less supportive section of the table (22).

In order to mount the adapter plate assembly (39), table clamp assemblies (39b, 39c) located on both sides of the adapter plate (39a) are configured to clamp the assembly (39) to the operating table (22). In this example, a single table (22) clamp assembly is used on the surgeon's side of the table (22) to minimize the amount of space consumed by the adapter plate assembly (39). FIG. 3D illustrates the adapter plate assembly (39) in a first, retracted configuration. To mount the adapter plate assembly (39), a clamp assembly (39b) on the surgeon's side of the table (22) may be removed or extended out of the way and the adapter plate assembly (39) is placed on the top surface of the operating table (22). The clamp assembly (39b) is repositioned and the bed clamp assemblies (39b) on the surgeon's side and the clamp assemblies (39c) on the other side are tightened onto the operating table rails. The support assembly (20) may then be mounted to the adapter plate rail (39d) and bedding may be placed over the entire adapter plate assembly (39).

Figure 5A:
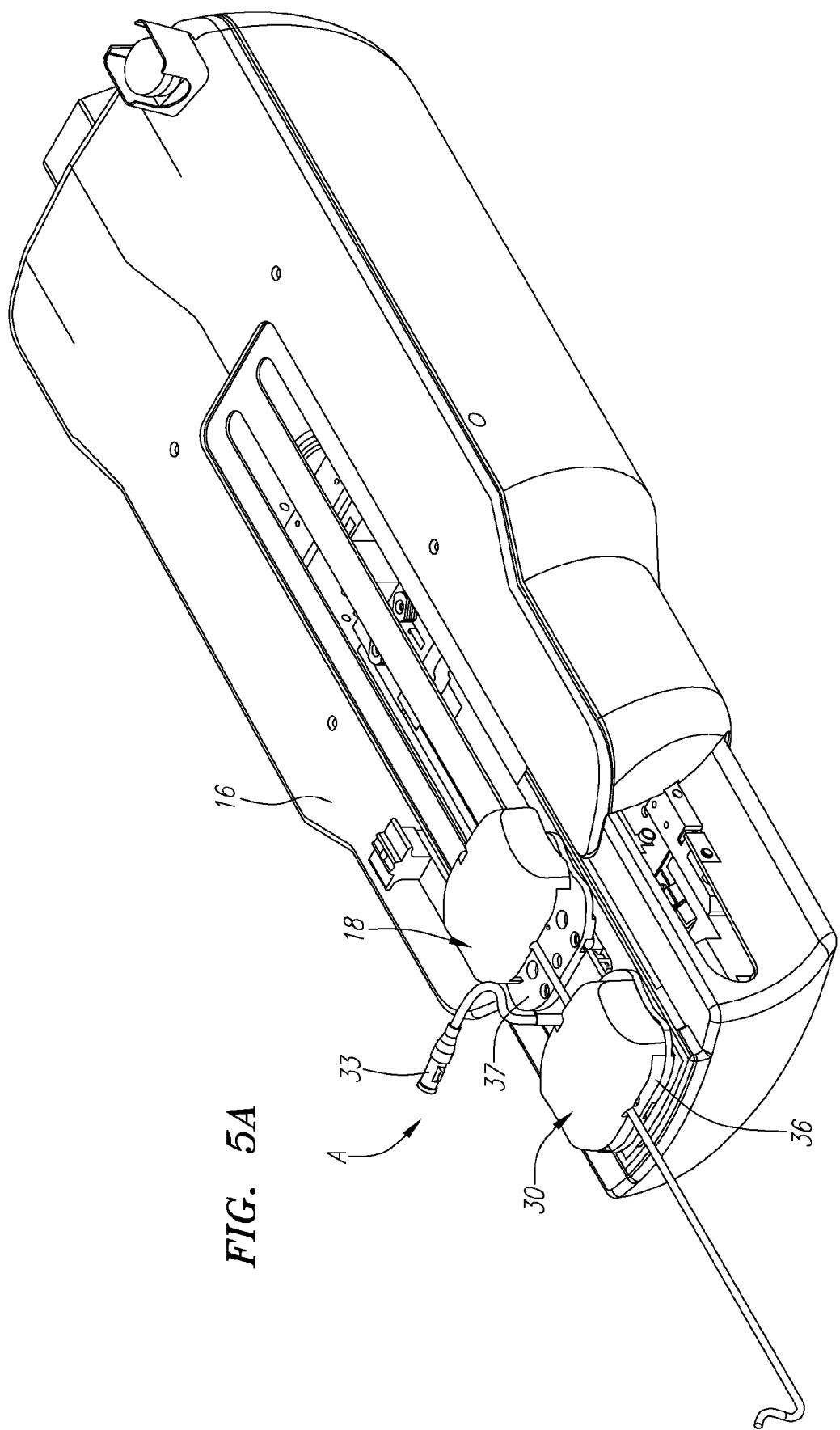
FIG. 5A illustrates a sheath and guide catheter assembly mounted on an instrument driver.
Figure 5B:
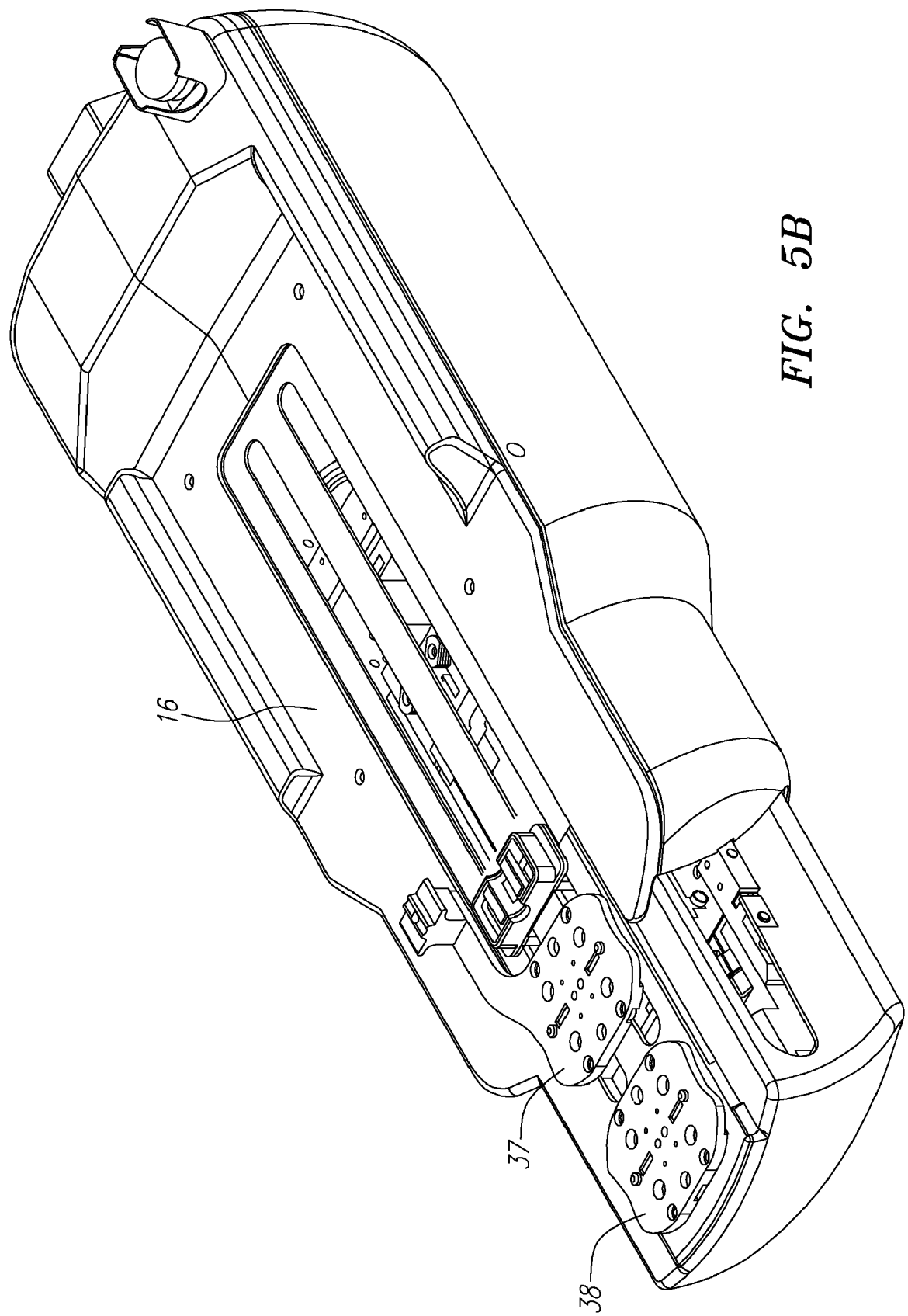
FIG. 5B further illustrates the instrument driver shown in FIG. 5A without the sheath and guide catheter assembly.
Figure 5C:
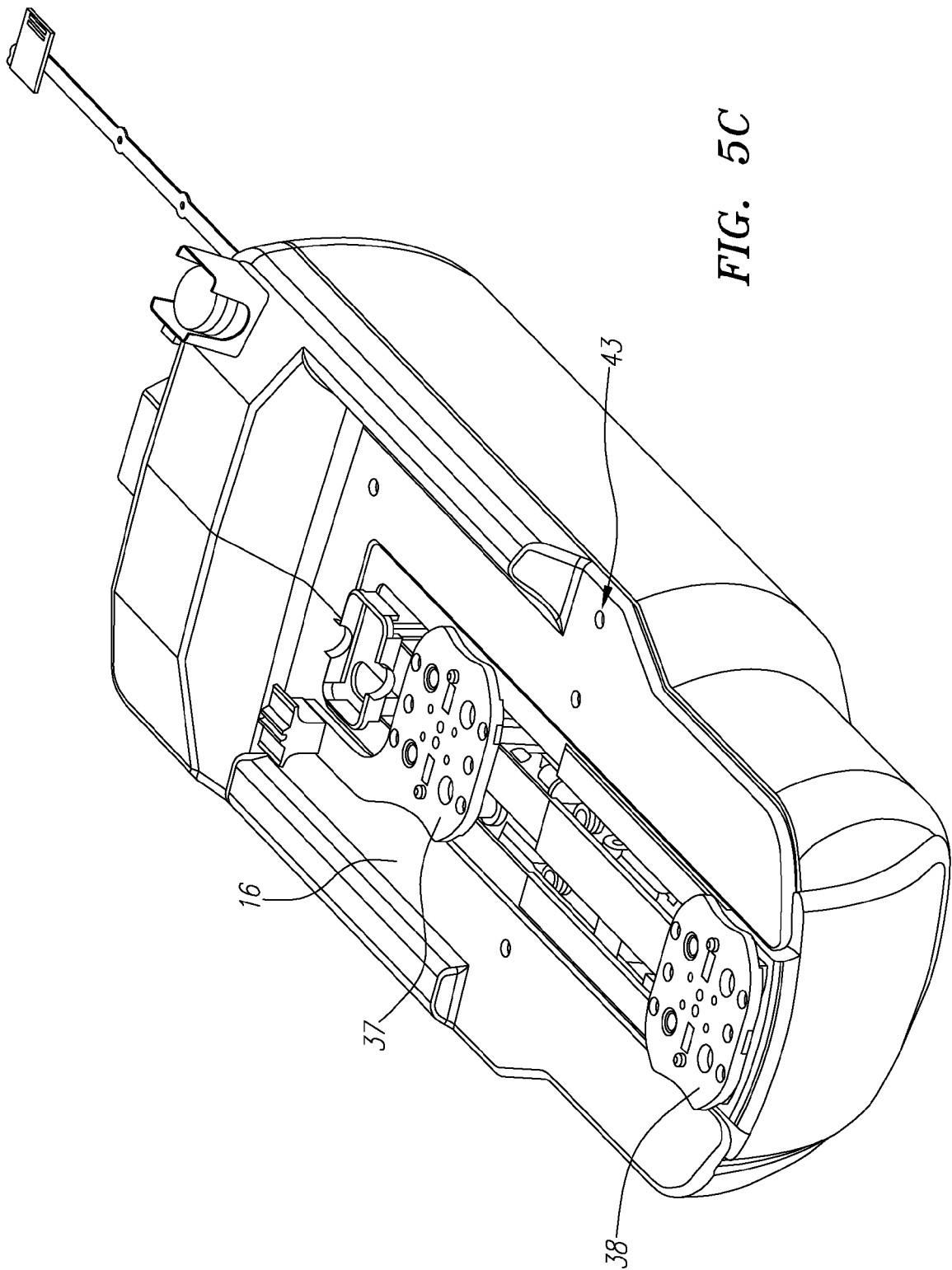
FIG. 5C further illustrates the instrument driver shown in FIG. 5B and one of the mounting plates being moved relative to the mounting plate arrangement shown in FIG. 5B.
Figure 5D:
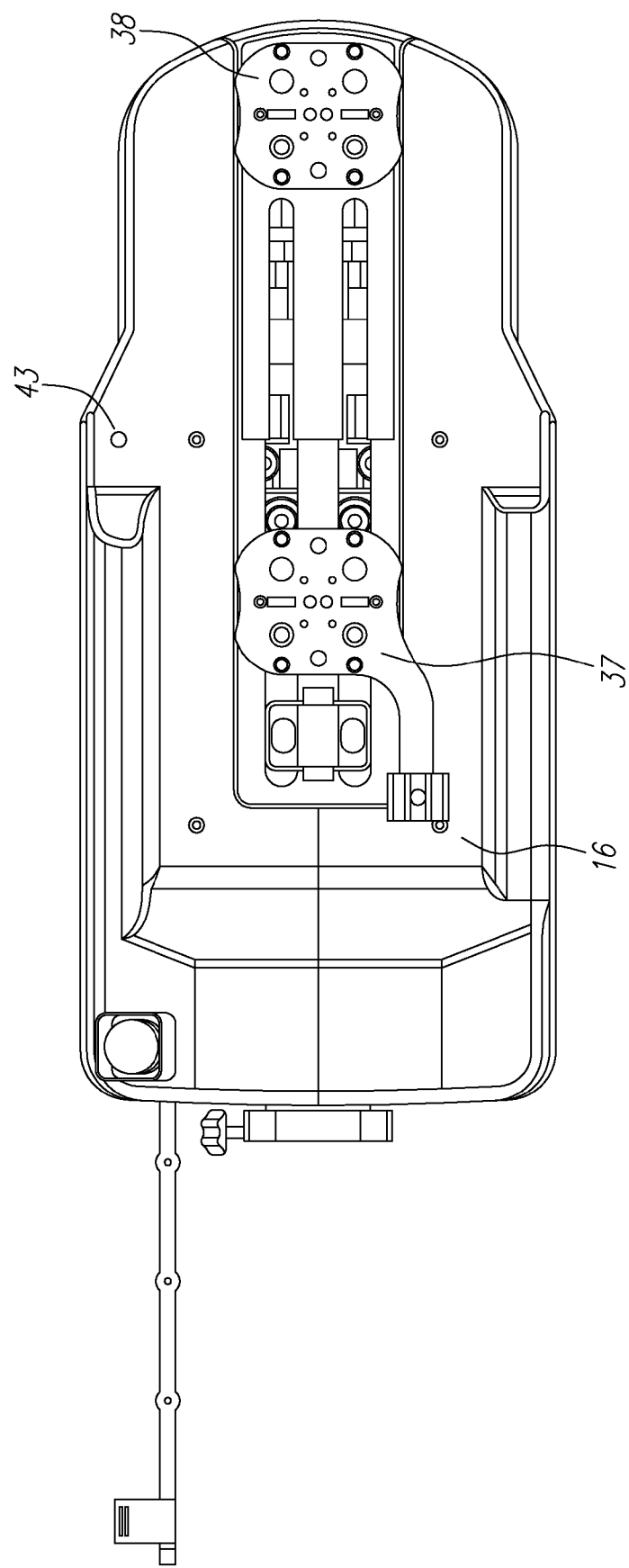
FIG. 5D is a top view of the instrument driver configured as shown in FIG. 5C.

With further reference to FIGS. 4 and 5A-5D, an instrument assembly (A) comprised of a sheath instrument (30) and an associated guide or catheter instrument (18) is mounted to associated mounting plates (37, 38) on a top portion of the instrument driver (16). FIGS. 5B-D illustrate the instrument driver (16) in further detail with and without an attached instrument assembly (A).

During use, the catheter instrument (18) is inserted within a central lumen of the sheath instrument (30) such that the instruments (18, 30) are arranged in a coaxial manner. Although the instruments (18, 30) are arranged coaxially, movement of each instrument (18, 30) can be controlled and manipulated independently. For this purpose, motors within the instrument driver (16) are controlled such that carriages coupled to the mounting plates (37, 38) are driven forwards and backwards on bearings. One or more components, such as the instrument driver (16), may also be rotated about a shaft to impart rotational motion to the catheter instrument (18) and/or sheath instrument (30). As a result, the guide catheter instrument (18) and the sheath instrument (30) can be controllably manipulated and inserted into and removed from the patient. Additional instrument driver (16) motors may be activated to control the bending of the guide catheter instrument (18) and the sheath instrument (30), the orientation of the distal tips of the instruments (18, 30), and any tools mounted at the distal tip of the catheter instrument (18).

As shown in FIGS. 5C-D, the instrument driver (16) may also include a status indicator (1051), which may be in the form of a light or LED that is located on the top face of the instrument driver (16). The indicator (1051) may be used to provide feedback to a user, e.g., via the operator workstation (2) as graphical messages on the monitor screens (4) or the touchscreen user interface (5), indicating whether the instrument driver (16) is properly mounted. For example, in certain systems in which the workstation (2) is located remotely from the operating table (22), it may be difficult for an operator installing a catheter assembly (A) onto the instrument driver (16) to receive status indicator messages without running back and forth between the workstation (2) and the instrument driver (16). Thus, the status indicator (1051) is provided on the top surface of an instrument driver (16) to provide the user feedback as to the operational status of the catheter assembly (A). For example, the indicator (1051) may be dark when no catheter assembly (A) has been mounted onto the instrument driver (16), but when a catheter assembly (A) is mounted onto the catheter interface surfaces (38, 40), the status indicator (1051) may begin to flash or blink green. This flashing or blinking green light is used to inform the operator that the catheter assembly (A) is being initialized, e.g., by reading a memory device located on the underside of a catheter splayer, pretensioning control elements such as control wires that extend through one or both of the catheter and sheath instruments (18, 30), and/or manipulating the catheter and/or instruments (18, 30) to a known state.

Once the catheter assembly (A) has been recognized and initialized, the status indicator (1051) may change to a steady green to indicate that the catheter assembly (A) is valid and ready for use. In this implementation, the steady green indicator light (1051) may remain illuminated until the catheter assembly (A) is removed or a fault occurs. The status indicator (1051) may change to a flashing or blinking amber color when a fault or error condition exists.

For example, if the catheter assembly (A) is invalid (i.e., being reused, improperly tensioned, etc.), jammed, or improperly installed, the instrument driver (16) and related controls can be configured to cause the indicator light (1051) to flash in an amber color to warn the operator that a catheter assembly (A) issue needs to be attended to and corrected. Although the status indicator (1051) is described in the context of a steady green value, a flashing green value, and a flashing amber value, other colors, and illumination sequences can be used to provide different status messages.

Figure 5E:
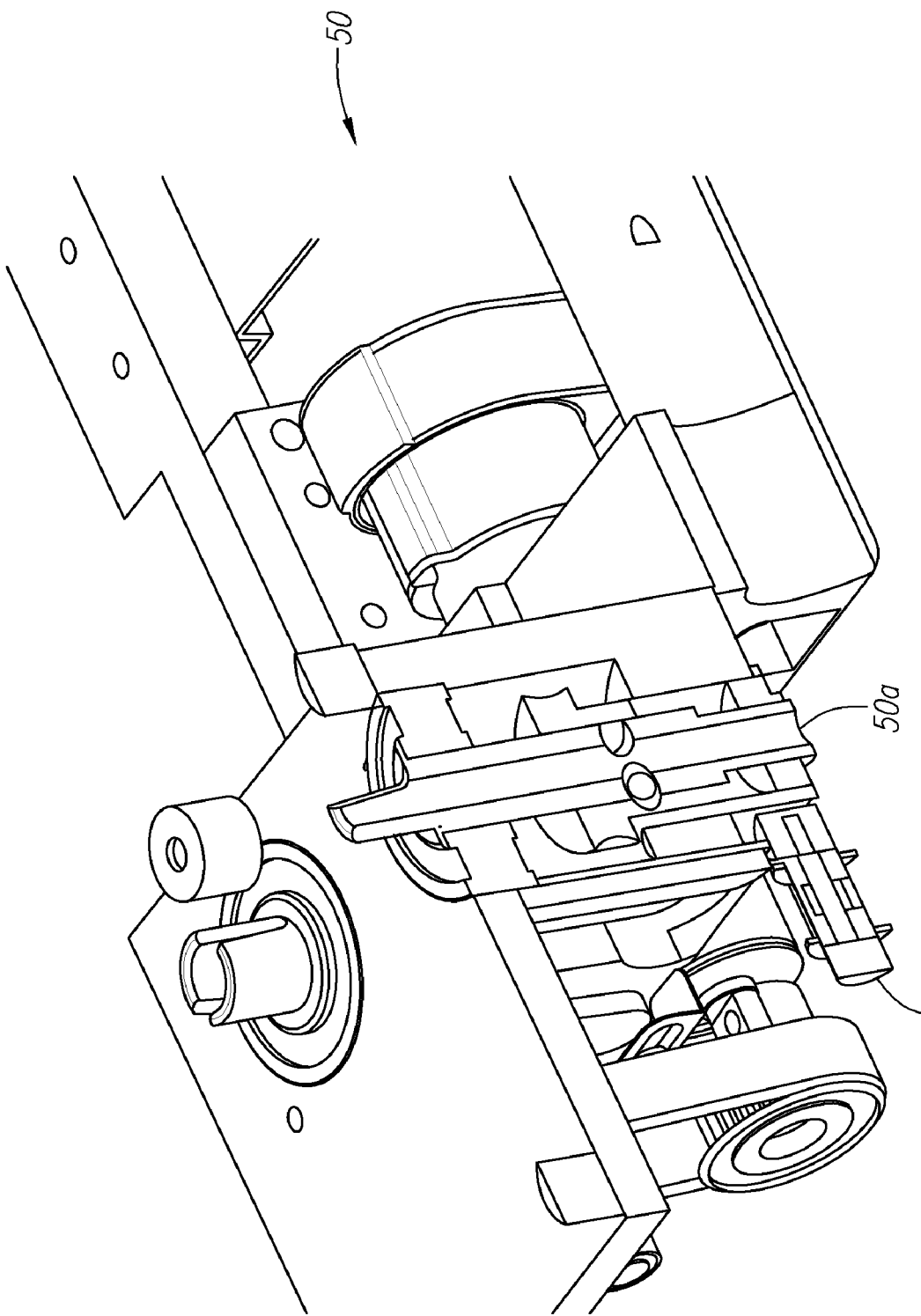
FIG. 5E is a cross-sectional view of a sheath control assembly.
Figure 5F:
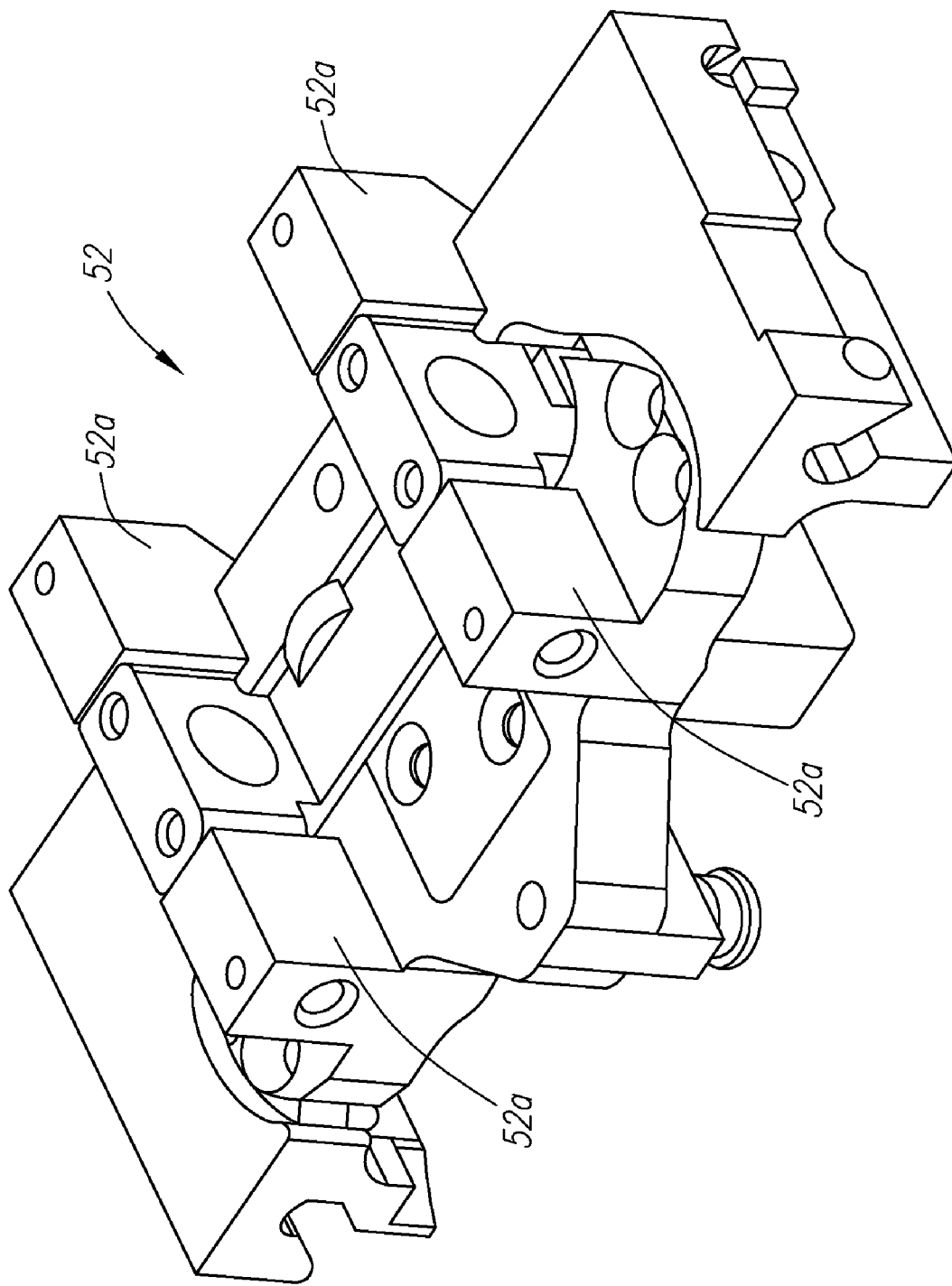
FIG. 5F illustrates one manner in which a dither assembly that may be used in the robotic surgical system shown in FIG. 1 may be constructed.
Figure 5G:
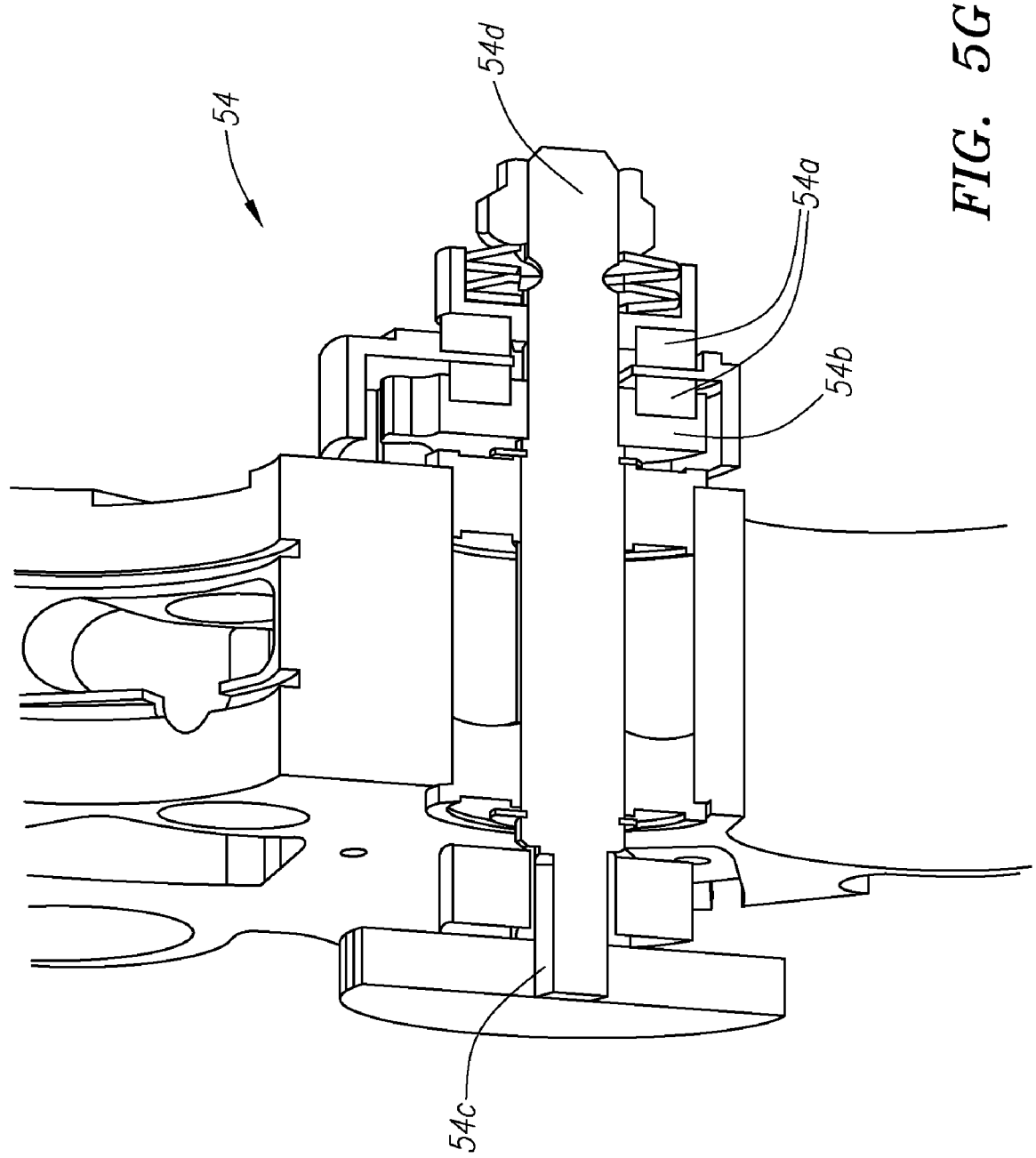
FIG. 5G illustrates a brake assembly of the instrument driver shown in FIGS. 4-5D.
Figure 5H:
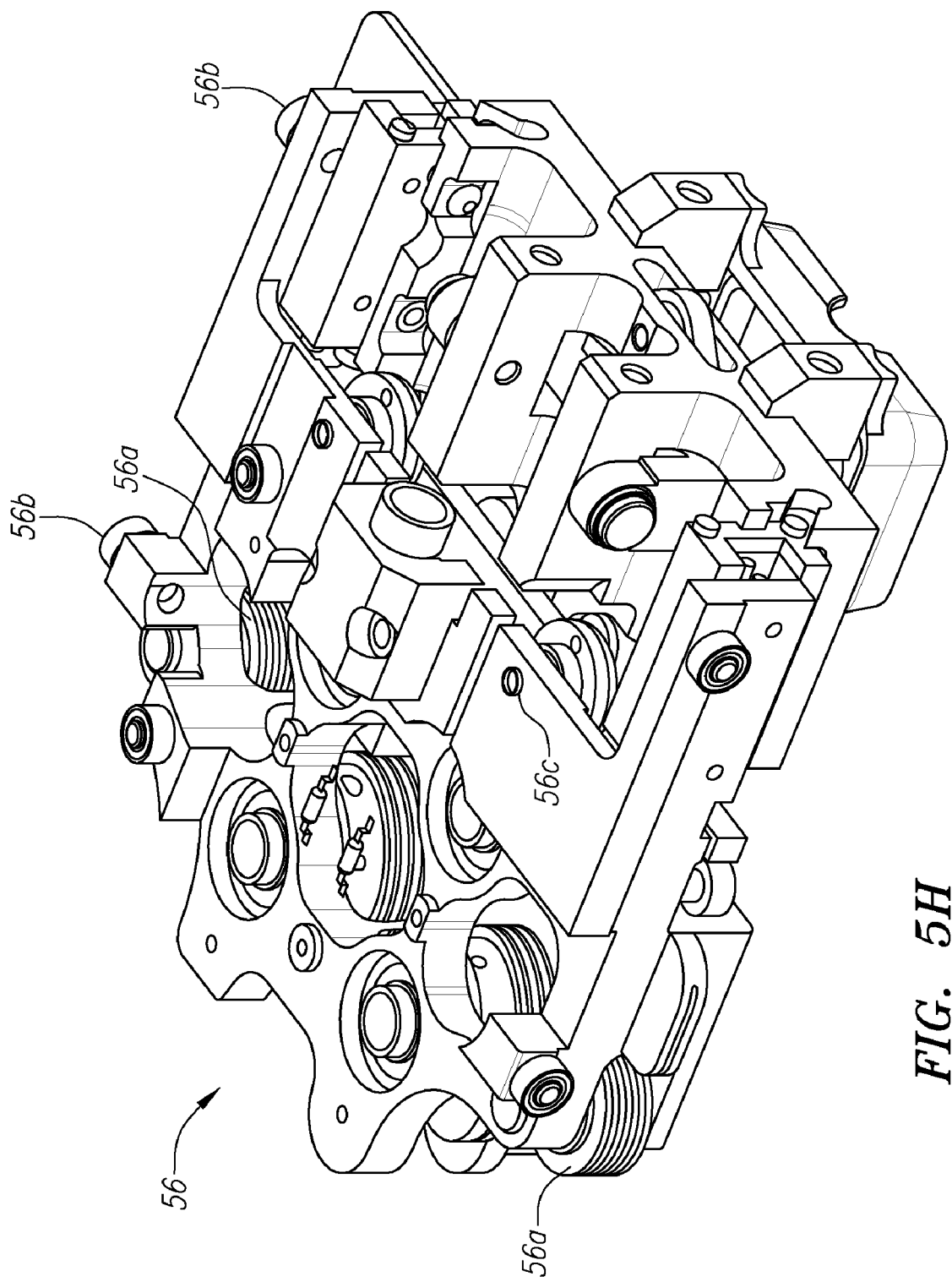
FIG. 5H illustrates a funicular assembly of the instrument driver shown in FIGS. 4-5D.
Figure 5I:
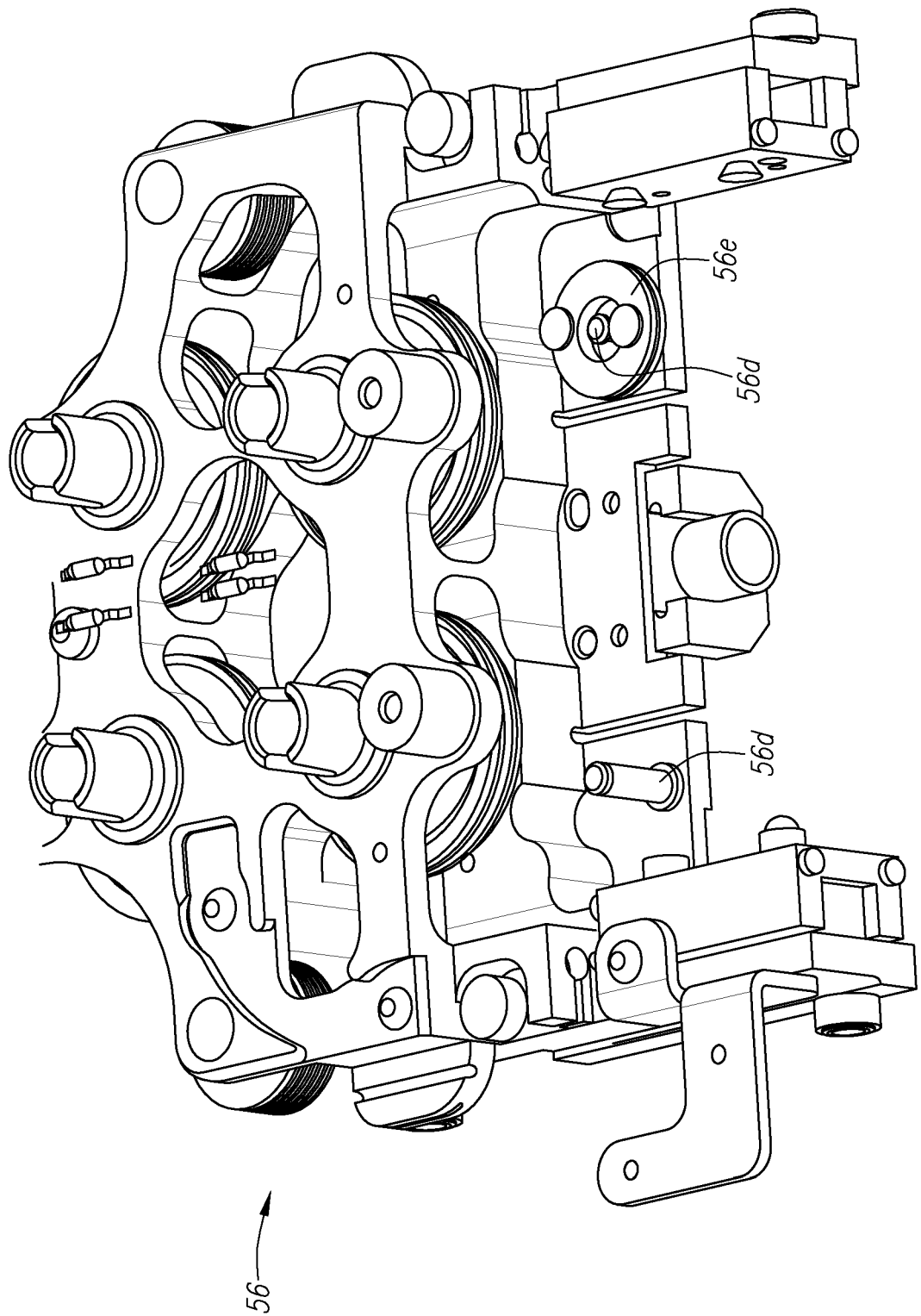
FIG. 5I is another perspective view of the funicular assembly shown in FIG. 5H.
Figure 5J:
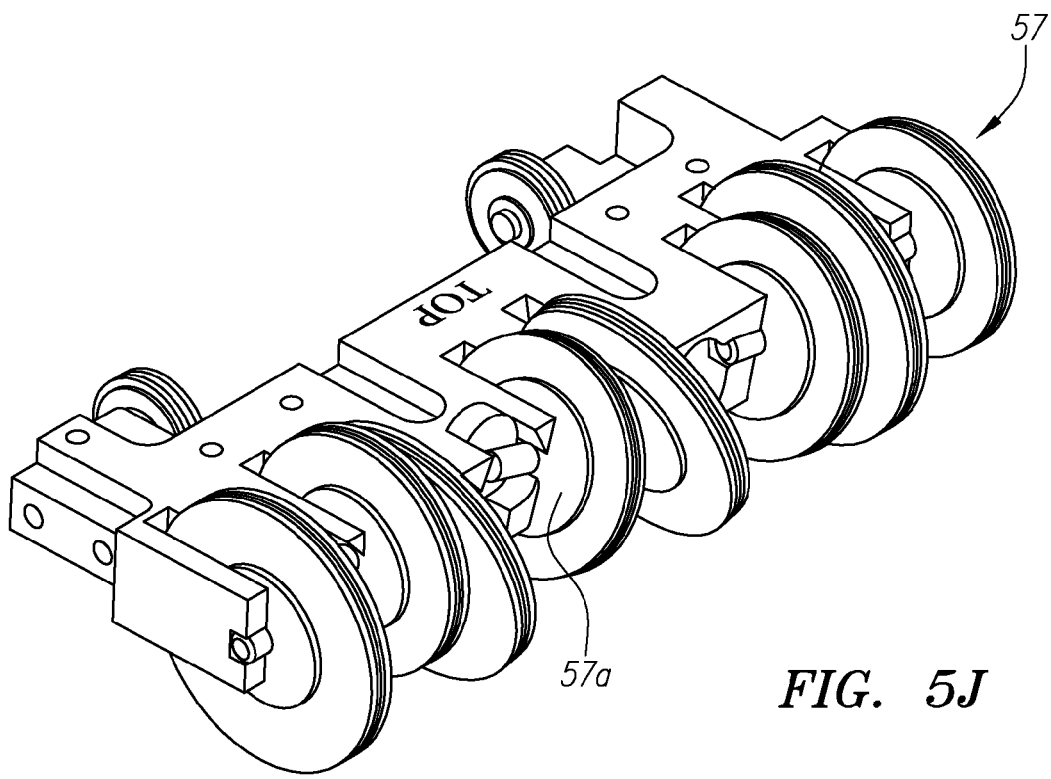
FIG. 5J illustrates a pulley assembly configured to drive a guide carriage of an instrument driver.
Figure 5K:
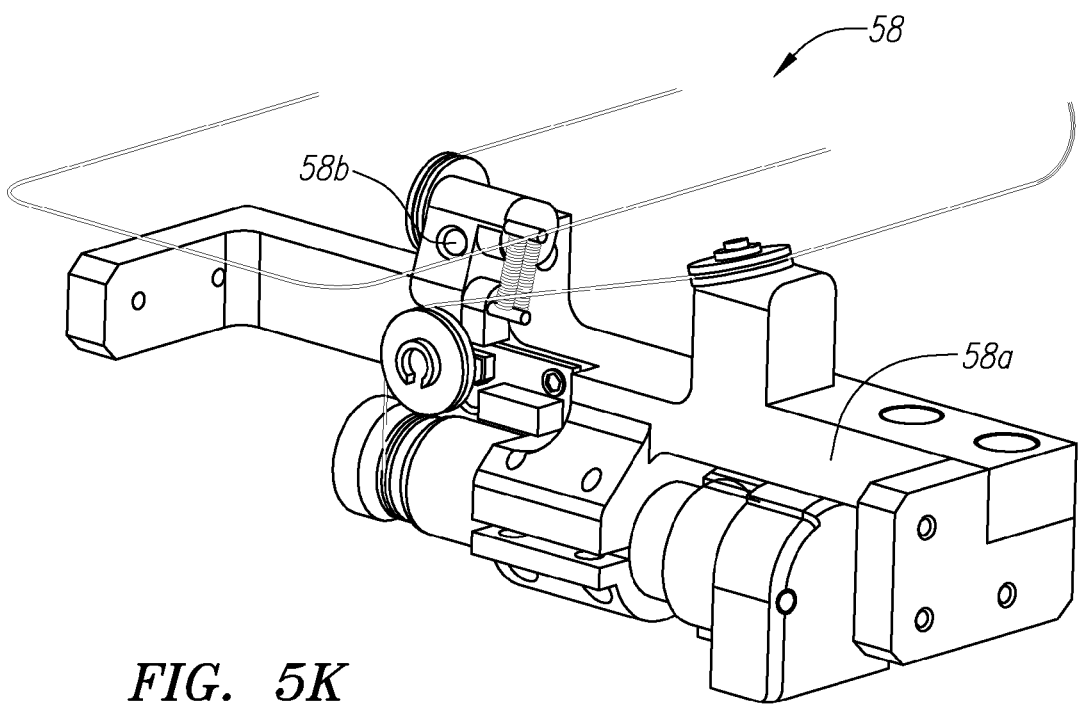
FIG. 5K illustrates a dither motor mount of an instrument driver.

FIGS. 5E-K illustrate components of another instrument driver (16) that may include components and be configured in a manner similar to the instrument driver described in U.S. patent application Ser. No. 11/481,433, the contents of which were previously incorporated herein by reference. FIG. 5E illustrates a remote control mechanism (RCM) sheath control assembly with its sheath insertion motor and sheath articulation assembly. FIG. 5F illustrates a dither assembly equipped with a plurality of load cell overload protection hard stops to protect the force sensor load cells. FIG. 5G illustrates aspects of a brake assembly for an instrument driver (16). FIGS. 5H-I illustrate a funicular assembly of an instrument driver (16). FIG. 5J illustrates a pulley assembly for driving a guide carriage of an instrument driver (16). FIG. 5K illustrates a dither motor mount (1233).

Referring to FIG. 5E, a remote control mechanism (RCM) sheath control assembly (50) includes a sheath insertion motor and sheath articulation assembly. In the illustrated embodiment, the sheath insertion motor is coupled to a drive or output shaft (50a) that is designed to move the sheath articulation assembly forwards and backwards, thus sliding a mounted sheath catheter instrument (18) forwards and backwards also. The sheath articulation assembly includes a sheath activation motor to prevent proximal bending such that the entire sheath instrument (30) may bend when the distal tip is bending, and a sheath articulation motor to cause the sheath instrument (30) to bend. In one implementation, a spacer is provided to the underside of the articulation assembly to remove any free play that may lower the retaining ring enough to contact the activation motor during operation.

The output shaft (50a) may be shorted to eliminate the need for a spacer and to avoid interference between the retaining ring and the motor. The assembly (50) may also include sheath articulation hard stop (50b), which may be in the form of a modified screw that is configured to align with a worm gear pin or a dowel pin hard stop (50b), which may be useful in the event that vertical misalignment causes two pins to wedge together occasionally to cause a fault since a dowel pin hard stop is not sensitive to vertical misalignment.

Referring to FIG. 5F, an instrument driver (16) may include a ditherer assembly or mechanism (52) that integrates ditherer mechanics with a force measurement mechanism (FMM), e.g., similar to that described in detail in U.S. Provisional Patent Application Nos. 60/776,065 and 60/801,355, the contents of which were previously incorporated herein by reference. In the illustrated example, the dither assembly (52) includes a linkage/pulley assembly, linear slides, and a guide splayer mounting plate that are mounted directly to the guide catheter carriage. Mounted to the linear slides is a FMM sliding base. The FMM is mounted to the sliding base. The working catheter instrument (18) is free to slide in the longitudinal direction on the linear bearings. The motion would be towards and away from a guide splayer mounted on the guide interface plate (38). As shown in FIG. 5F, a plurality of load cell overload protection hard stops (52a) are provided on both sides of the assembly (52) to advantageously protect force sensor load cells.

Referring to FIG. 5G, the instrument driver (16) may include a brake assembly (54) that includes twin brake pads (54a), a square shaft drive hard stop (54b) that is axially disposed about a shaft (54d), and a surface (54c). The portion of the shaft (54d) proximal to the gear has been machined with the key surface (54c) for easier alignment of the gear and other parts with the shaft (54d) during assembly.

Referring to FIGS. 5H-I, an instrument driver (16) may include a funicular assembly (56) that is coupled as part of guide carriage and ditherer assemblies. The funicular assembly (56) may include idlers (56a), e.g., anodized aluminum capstan idlers or polycarbonate capstan idlers, which may be useful for limiting cable slippage. Retaining rings may be used to capture bearings (56b) for flanges that receive pulley drive shafts (61a) from a catheter splayer (61). The spacing of the linear bearings of a guide carriage may be increased as necessary to reduce rocking motion as the carriage traverses along its rails to move a mounted guide catheter. Swaged pins (56c) are used to fasten the upper plate into place, and flanged pins (56d) are press fitted to the back portion of the funicular assembly (56). A cam (56e) with ball detents to receive the dither mechanism timing chain is coupled to a pin (56d) on the assembly.

FIG. 5J illustrates a pulley assembly (57) for driving a guide carriage of an instrument driver (16). In the illustrated example, the pulley assembly (57) includes flanged plain bearings (57a) that are included with each pulley in the assembly to support side loading and to prevent metal to metal contact, which may wear down parts and cause failures.

Referring to FIG. 5K, a dither motor mount (58) may be configured to have increased stiffness in sheet metal (58a) to prevent undesired flexing of the mount (58). In the illustrated example, a tensioner lock screw (58b) is located on an upper portion of the mount and may be used to adjust the tension of a cable that is used to drive the dither mechanism. A sensor can be soldered into to a cable in a pocket mount and may be a surface mounted PCB that includes a—connector for easy attachment.

Figure 6B:
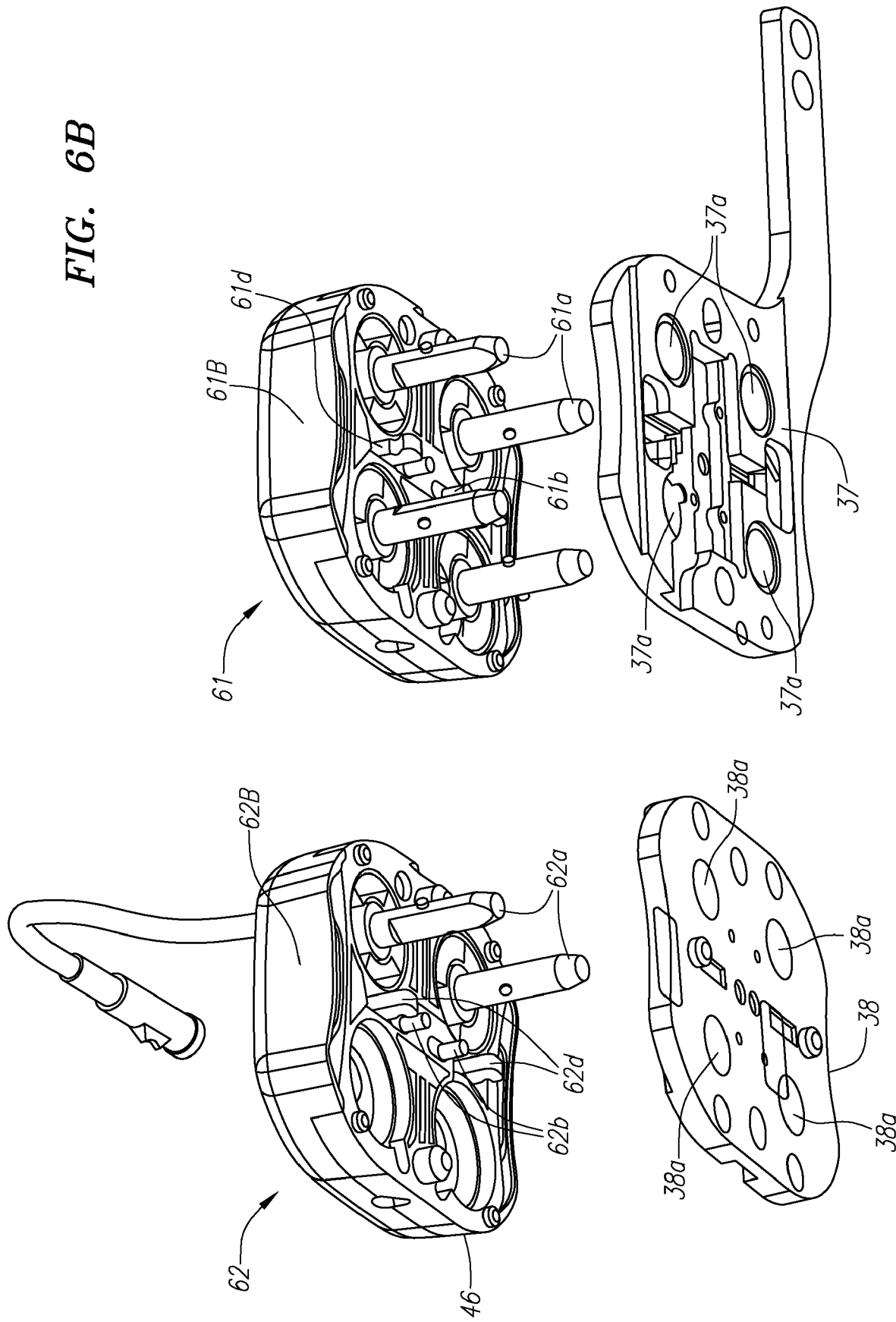
FIG. 6B further illustrates how sheath and guide splayers interface with respective mounting plates.
Figure 6C:
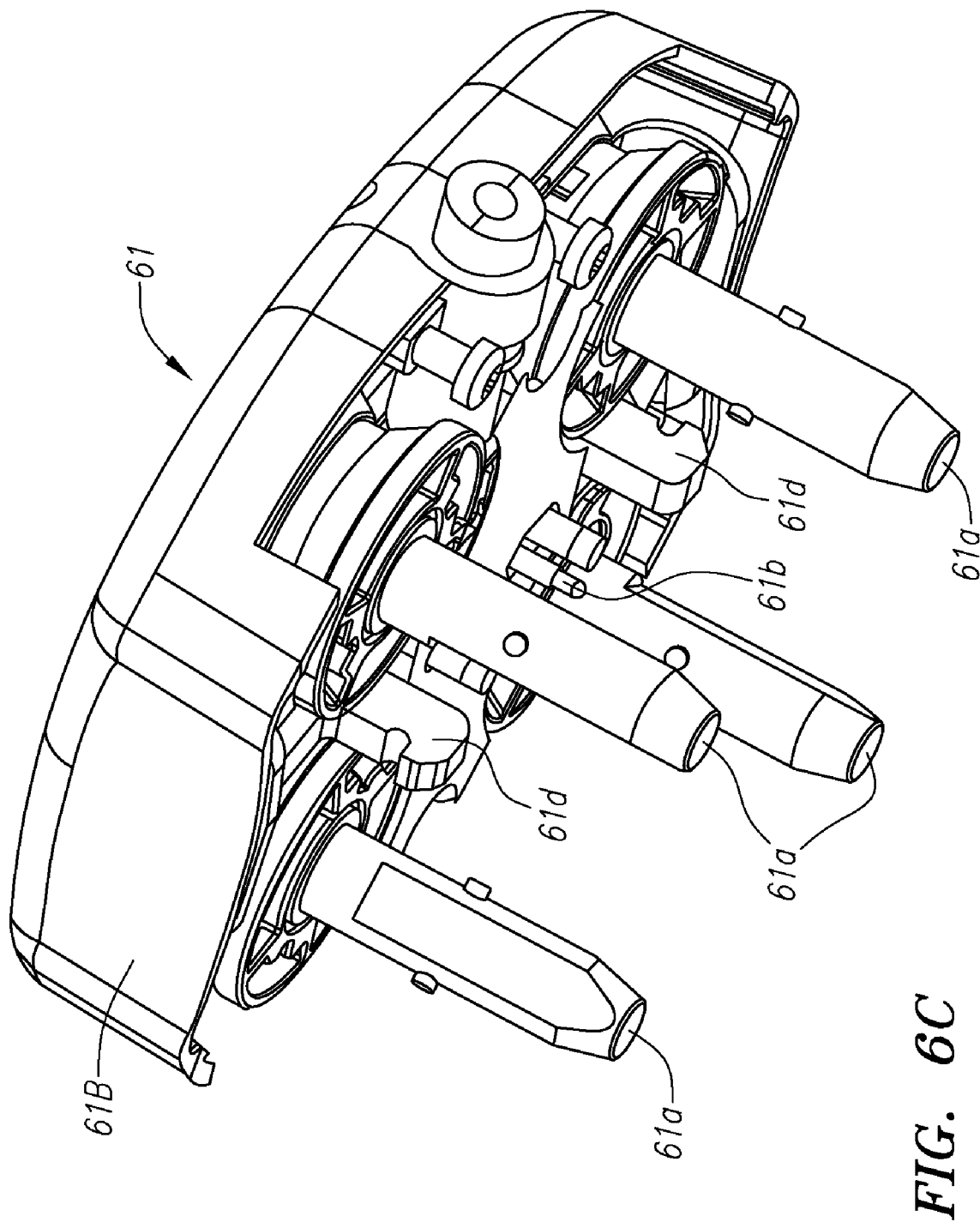
FIG. 6C is a bottom perspective view of a guide catheter splayer that may be mounted to an instrument driver of a robotic surgical system.
Figure 6D:
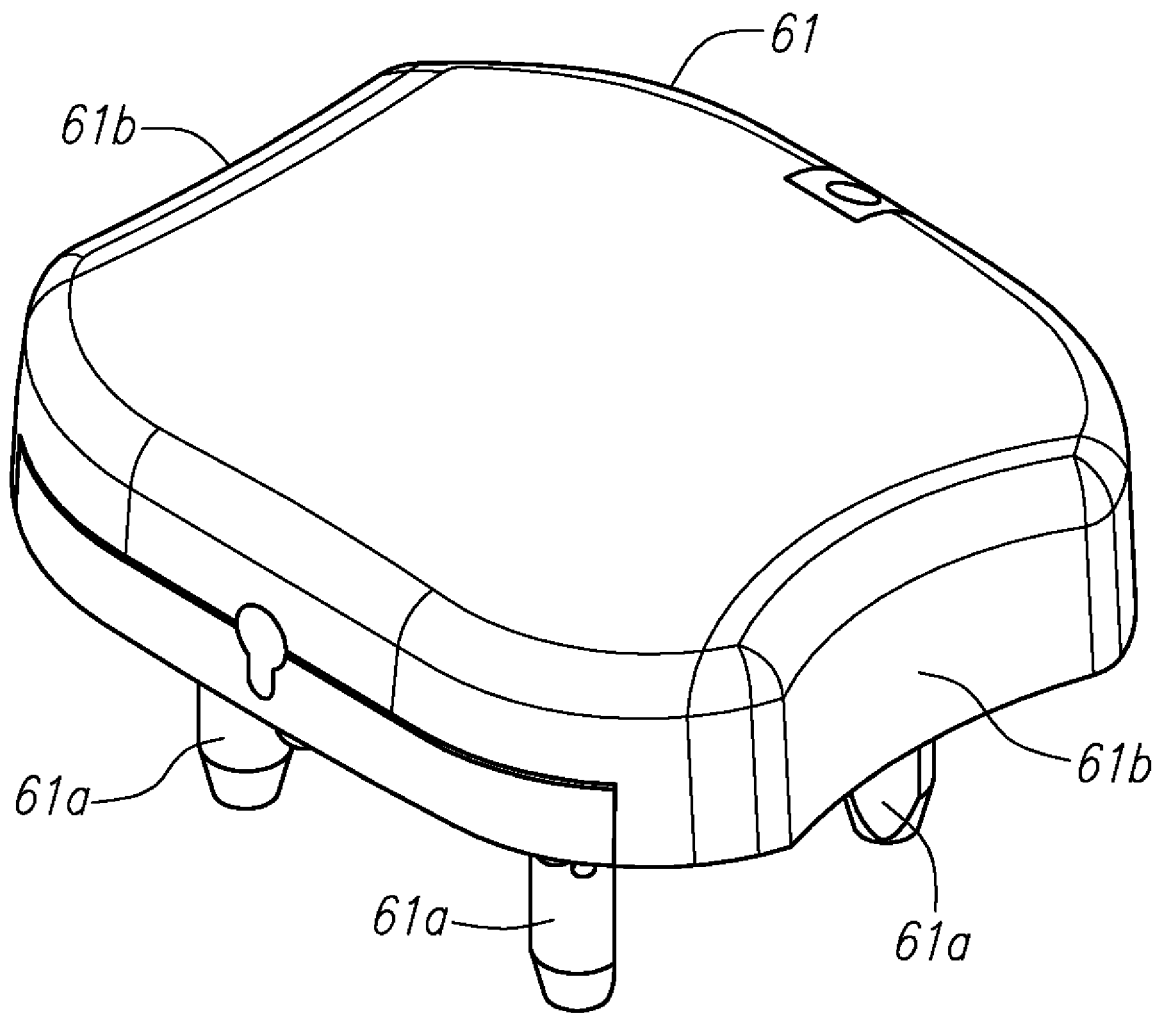
FIG. 6D is a top perspective view of the guide catheter splayer shown in FIG. 6C.

Referring to FIGS. 6A-E, an assembly (A) that includes a sheath instrument (30) and a guide or catheter instrument (18) positioned over their respective mounting plates (38, 37). In FIG. 6A, interface mounting plates (37, 38) are illustrated and other components of the instrument driver (16) are not illustrated for ease of illustration.

In the illustrated example, a guide catheter instrument member (61a) is coaxially interfaced with a sheath instrument member (62a) by inserting the guide catheter instrument member (61a) into a working lumen of the sheath catheter member (62a). As shown in FIG. 6A, the sheath instrument (30) and the guide or catheter instrument (18) are coaxially disposed for mounting onto the instrument driver (16). However, it should be understood that a sheath instrument (16) is used without a guide or catheter instrument (18), or a guide or catheter instrument (18) is used without a sheath instrument (30) may be mounted onto the instrument driver (16) individually. With the coaxial arrangement as shown in FIG. 6A, the guide catheter splayer (61) is located proximally relative to, or behind, the sheath splayer (62) such that the guide catheter member (61a) can be inserted into and removed from the sheath catheter member (61b).

Examples of how sheath and guide sprayers (1050, 1052) may be structured are shown in FIG. 6B. When a catheter is prepared for use with an instrument, its splayer is mounted onto its appropriate interface plate. In this case, the sheath splayer (62) is placed onto the sheath interface plate (38) and the guide splayer (61) is place onto the guide interface plate (37). The interface plates (37, 38) may be located on the top surface of the instrument driver (16). In the illustrated example, each interface plates (37, 38) has four openings (37a, 38a) that are designed to receive corresponding D-shaped, stainless steel insert molds or drive shafts (61a, 62a) (generally shaft 61a) attached to and extending from the pulley assemblies of the splayers (61, 62). In the example illustrated in FIGS. 6B and 6E-F, two shafts (62a) of the sheath splayer (62) are insertable within the right apertures or two openings (38a) of the sheath interface plate (38) as the splayer (62) is mounted onto the RCM. Similarly, as illustrated in FIGS. 6B and 6K-L four shafts (61a) of the guide splayer (61) are insertable within the four apertures or openings (37a) of the guide interface plate (37). A pulley lock block in each splayer (61, 62) may include a pair of pogo pins (61b, 62b) (generally 61b) that are designed to pass through a pair of openings in the splayer base. In one embodiment, the pogo pins (61b) serve as a communication interface between the instrument driver (16) and a memory device that contains catheter characteristics inside the catheter splayer. When the splayer (61, 62) is mounted with respective interface plates (37, 38), pins (61b, 62b) make contact with their associated interface plate (37, 38), and as an interface plate (37, 38) engages the pins (61b, 62b), the pins (61b, 62b) are pushed upwardly which, in turn, causes the pulley lock block to move upwardly and compress an internal foam spring.

With further reference to FIGS. 6G-H, a torsion spring (61c) that is configured for insertion within a mounting plate (e.g., as shown in FIGS. 6K-L). One suitable torsion spring (61c) defines a shape having a height of about 0.28" and a width of about 0.50". FIG. 6I illustrates the positioning of a torsion spring (61c) within a mounting plate in which spring (61c) covered by a plate (61d), and FIG. 6J is the same view as shown in FIG. 6I except with the plate (61d) removed to expose the spring (61c).

As a splayer is mounted to an instrument driver (16), the release surfaces on the opposing sides of the splayer may need to be depressed in order to have the latches to fit through the openings on the mounting surface. Thus it may be desirable to be able to insert a splayer without applying significant force on the instrument driver (16) to push a splayer down onto its mounting surface of a mounting plate (37, 38). Utilizing torsion springs (61c) in each mounting surface results in a reduction in the amount of downward force that required to insert a splayer since the foam springs located inside of the splayer keep the latches (61d, 62d) (generally 61d) in a latched position and may not have to be overcome. The torsion springs (61c) move out of the way as the latches (61d) slide through the openings while a splayer is being mounted into place. Once the latches (61d) pass, the springs (61c) move back into place, and the latches (61d) are engaged with the bottom surfaces of the interface plates (37, 38).

Figure 6E:
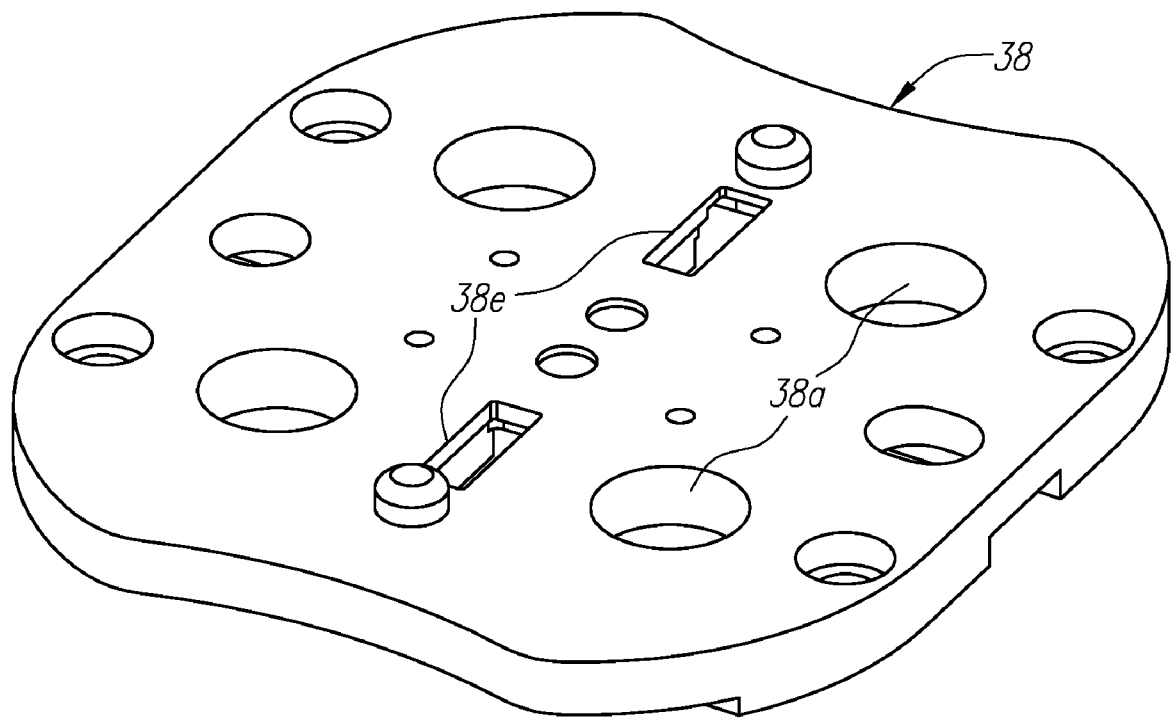
FIG. 6E is a perspective view of a sheath instrument mounting plate.
Figure 6F:
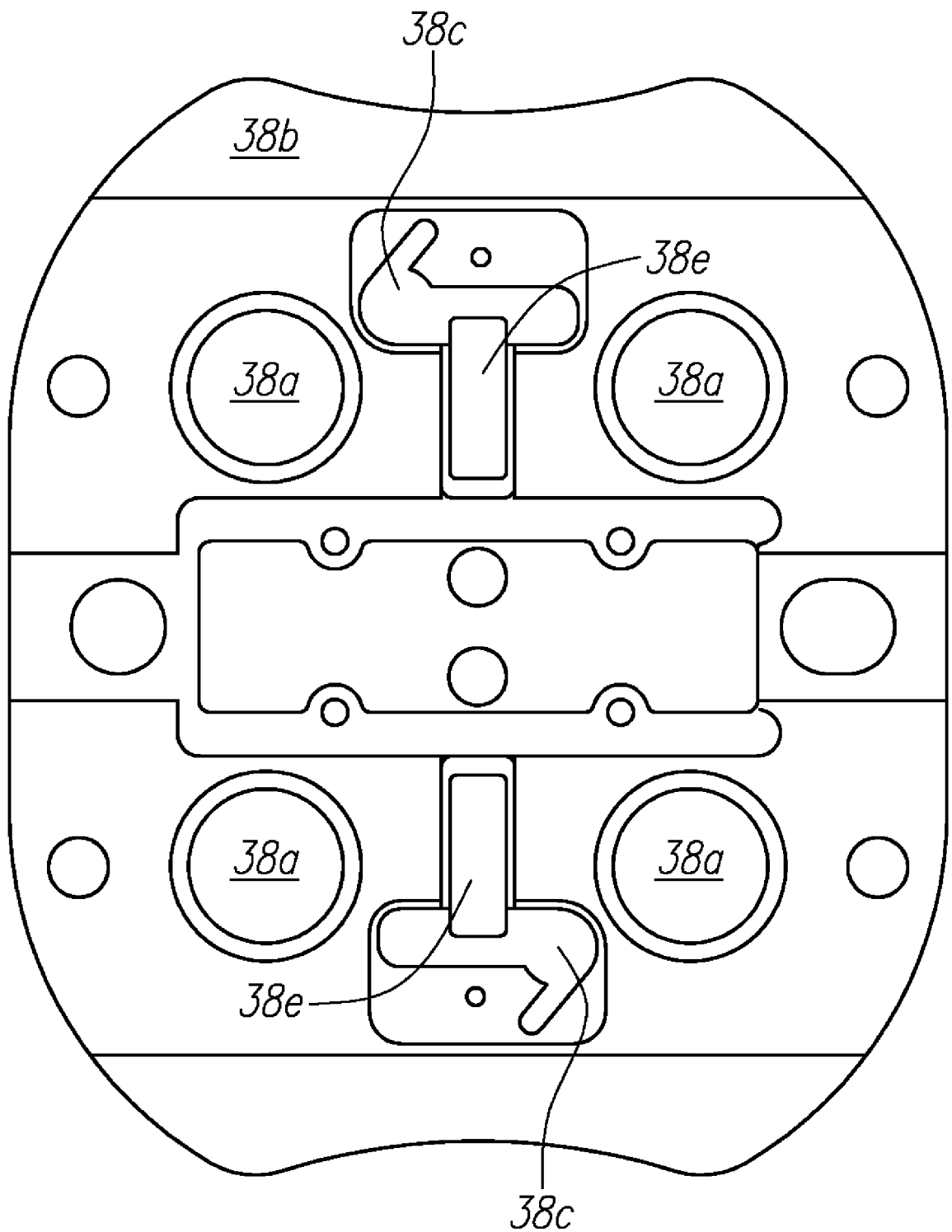
FIG. 6F is a bottom view of the mounting plate shown in FIG. 6E.

The sheath interface mounting plate (38) as illustrated in FIGS. 6E-F is similar to the guide interface mounting plate (37) as illustrated in FIGS. 6K-L and thus, similar details are not repeated. One difference between the plates (37, 38) may be the shape of the plates. For example, the guide interface plate (37) includes a narrow, elongated segment, which may be used with, for example, a dither mechanism. Both plates (37, 38) include a plurality of openings (37a, 37b) to receive drive shafts (61a, 62b) and latches (61d, 62d) from splayers (61, 62), respectively. Referring to FIGS. 6F, 6I, 6J and 6L, undersides (37b, 38b) of plates (37, 38), respectively, two pockets (37c, 38c) are located adjacent the notch openings (37e, 38e) to hold torsion springs (61c). As shown in FIG. 6J, the pocket (37c, 38c) of this example includes a pattern to help preload and position the spring (61c) in the right orientation.

During manufacturing, a torsion spring (61c) may be fitted within each cavity (37c, 38c) as illustrated in FIG. 6J. A cover plate (61e) is placed over or screwed into place with nylon screws over the cavity to maintain the spring (61c) in place. In the illustrated example, a spring cavity (37c) overlaps with openings (37e), thus allowing for the spring (61c) to guard part of the opening (37e). Although the structural configurations described above may apply to the guide player (61) and the sheath splayer (62), for ease of explanation, reference is made to the guide splayer (61) and its associated mounting plate (37).

In the illustrated example, latches (61d), e.g., a pair of latches (61d), are located on the inner surface or underside of the guide splayer (61) (as shown in FIG. 6B). These latches (61d) are designed to engage with corresponding notches or openings (38e) of the plate (37). When the splayer (61) is mounted to the interface plate (37), the latches (61d) are inserted through the notches (61e) to latch and securely couple the splayer (61) to the instrument driver (16). As the latches (61d) slide through the openings (37e), the latches (1056) engage with the torsion springs (61c). The application of downward force in mounting the splayer (61) causes the springs (61c) to yield, thus allowing the latches (1056) to pass and latch onto the bottom of the interface plate (37). The splayer (61) cover and the latches (1056) of this embodiment may, for example, be ABS molded.

A pair of urethane based compliant members located on the sides of the splayer (61) cover is over molded with the splayer (61) cover such that the splayer (61) cover us formed as a single piece. In the illustrated example, along opposing sides (61f) (FIG. 6B) on the inside of the splayer (61) cover, two pairs of foam pads are located adjacent to a latch (61d) and serve to provide its latch (61d) some spring tension to provide for better engagement between the splayer (61) cover and the interface plate (37). In one implementation, a user can remove a splayer (61) mounted to an instrument driver (16) by squeezing the compliant members at the opposing sides (61f) which, in turn, depresses and disengages the latches (61d) from the notches or openings (37e) of the interface plate (37). As the splayer (61) is pulled upwardly, the latches (61d) may make contact with the torsion springs (61c).

Figure 6M:
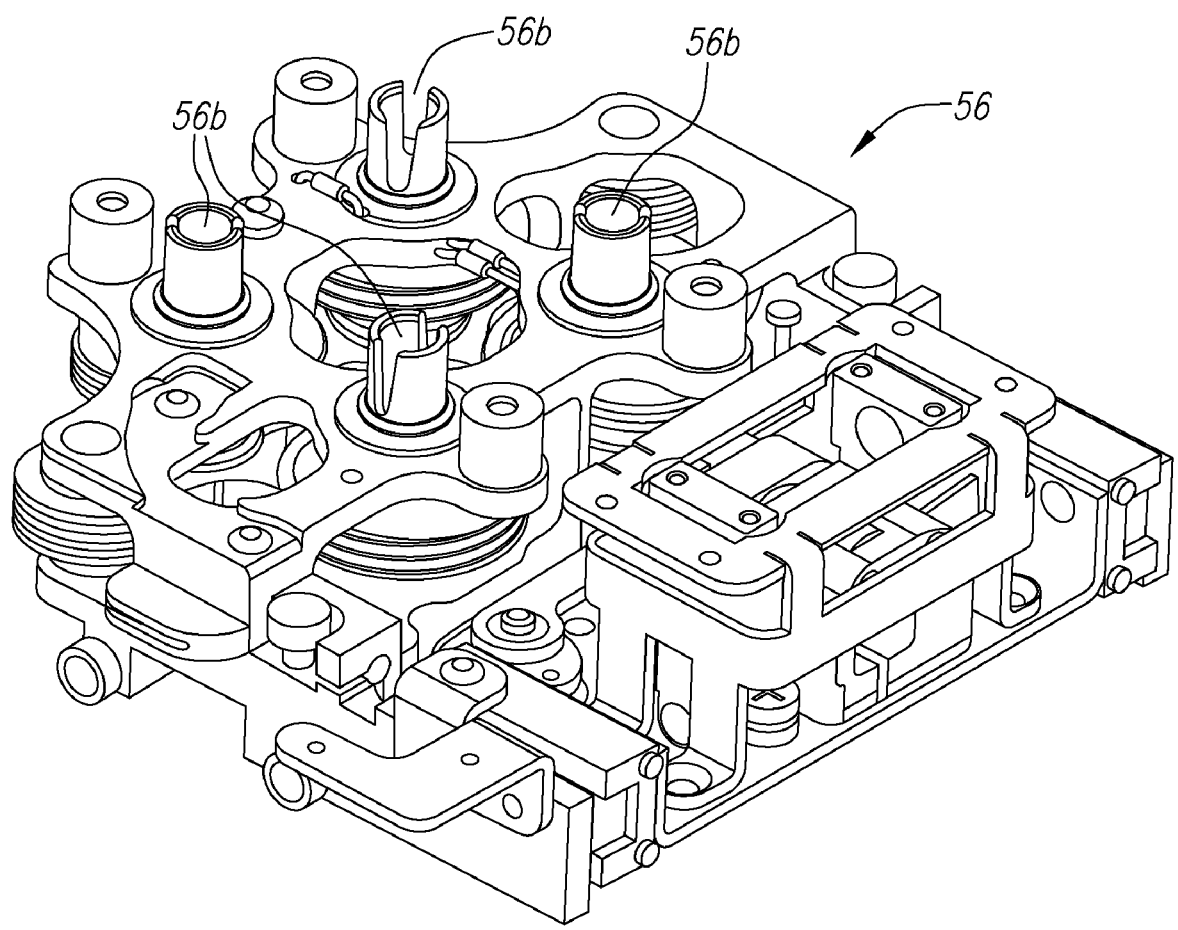
FIG. 6M is a perspective view of a slidable carriage or funicular assembly of an instrument driver and receiver slots configured to receive and engage with splayer shafts.

Referring to FIG. 6M, another slidable carriage or funicular assembly (56) that may be suitable for instrument driver (16) includes four receiver slots (56f) for receiving and engaging with drive shafts (61a) extending from a catheter splayer (61). Also illustrated in FIG. 6M is a dither mechanism.

FIGS. 6N-T illustrate shafts (61a, 62a) of splayers (61, 62) for use with instrument driver (16) in further detail. In certain situations during a surgical procedure, torque forces may act on a catheter assembly and cause the drive shafts of a splayer to become stuck or difficult to remove while the torque force is active. The drive shaft (61a) and associated receiver slots as shown in FIGS. 6N-T facilitate easier removal of splayers while the catheter is under a torsional load. For example, in some situations, especially during an emergency, it may be desirable to remove the catheter assembly (18) quickly, but if a catheter assembly (18) is articulated tightly, a strong torque or pull may be exerted on the catheter control wires and sprayers, thereby making removal more difficult. In one arrangement, the shafts (61a) of a splayer were inserted into receiving sleeves in the instrument driver. The shaft (61a) configuration shown in FIGS. 6N-T allows such removal to be accomplished more easily compared to standard drive shafts.

Figure 6O:
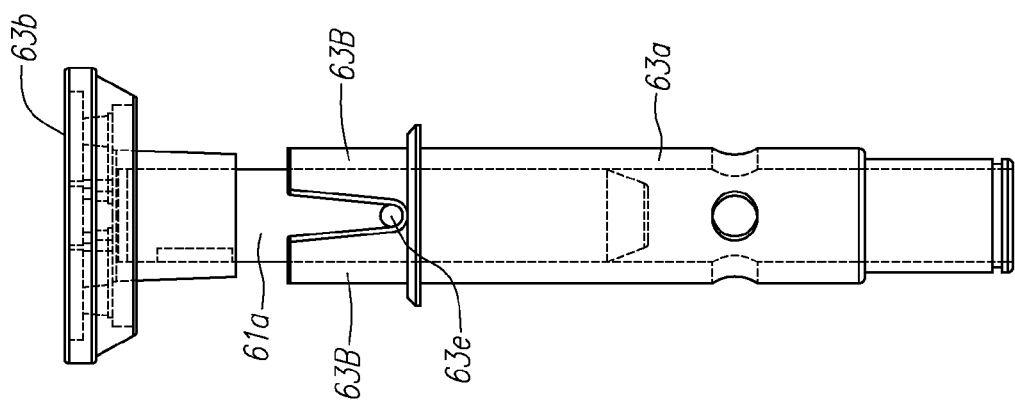
FIG. 6O of a drive shaft that is inserted into a sleeve receptacle.
Figure 6N:
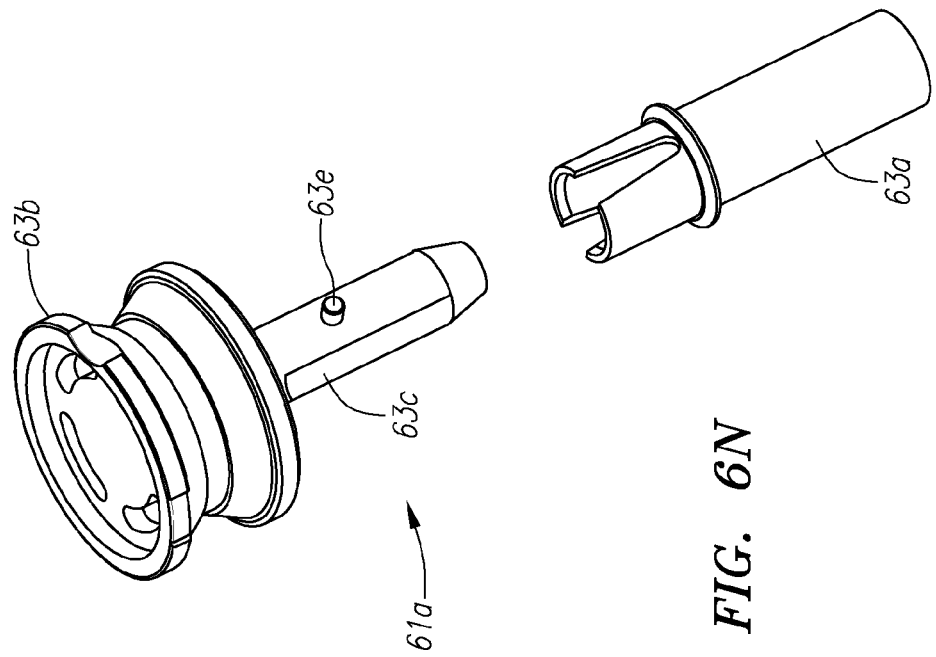
FIG. 6N is a perspective view of a drive shaft positioned for insertion into a sleeve receptacle located on an instrument driver.
Figure 6P:
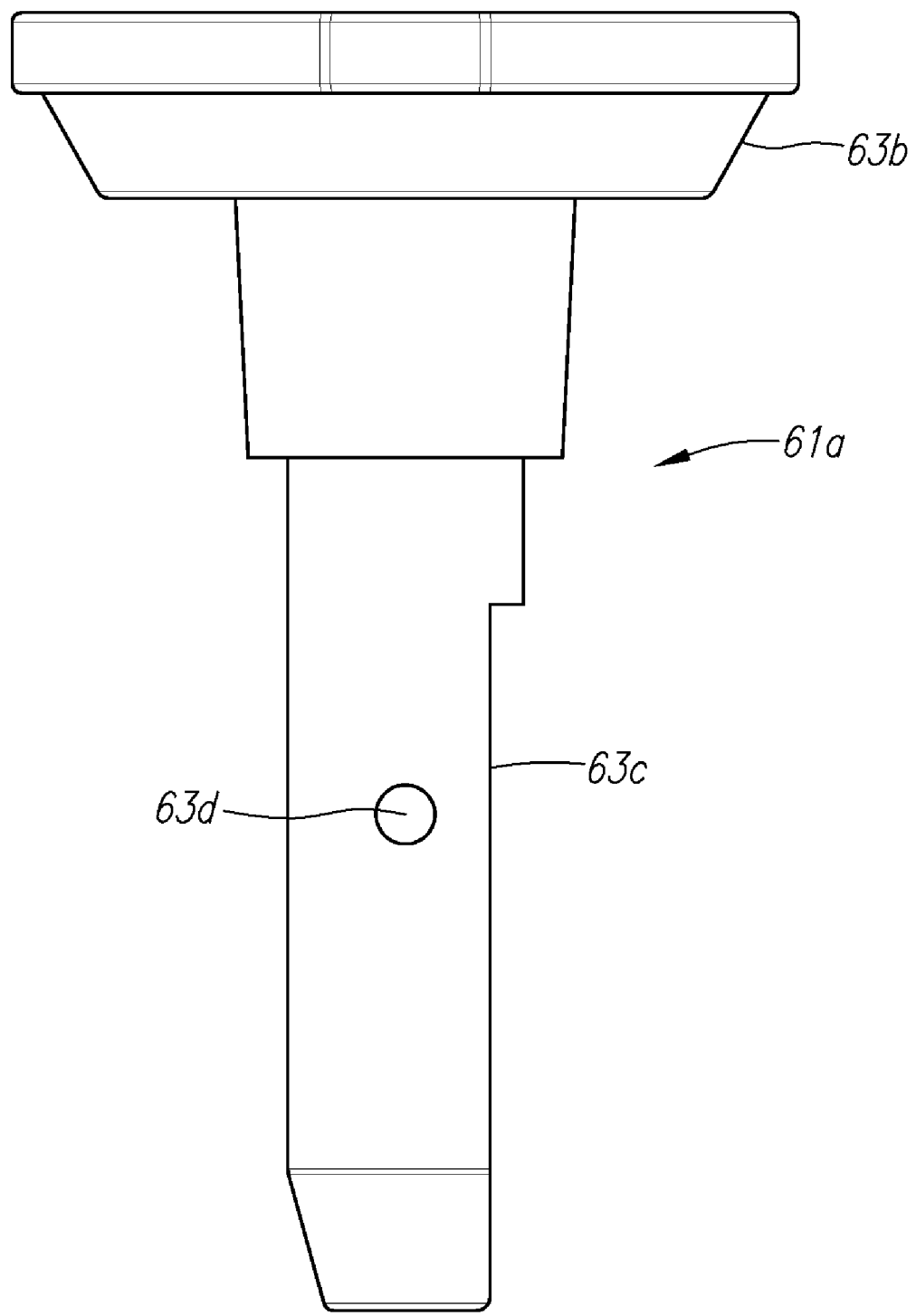
FIG. 6P is a side view of a drive shaft and associated pulley assembly and illustrating a flat edge of one side of the drive shaft.
Figure 6Q:
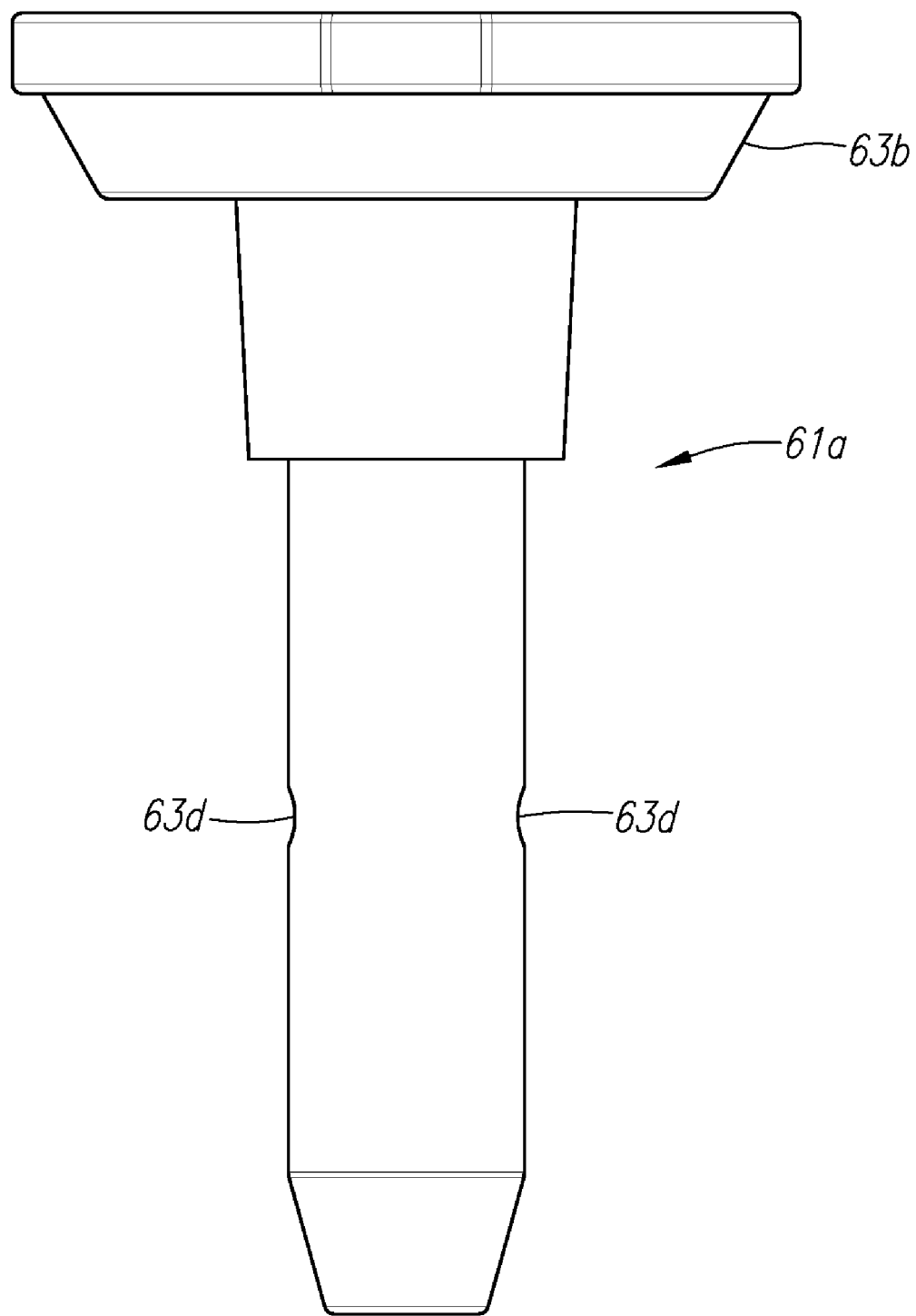
FIG. 6Q is another view of the drive shaft shown in FIG. 6P illustrating a smooth portion of the drive shaft.
Figure 6R:
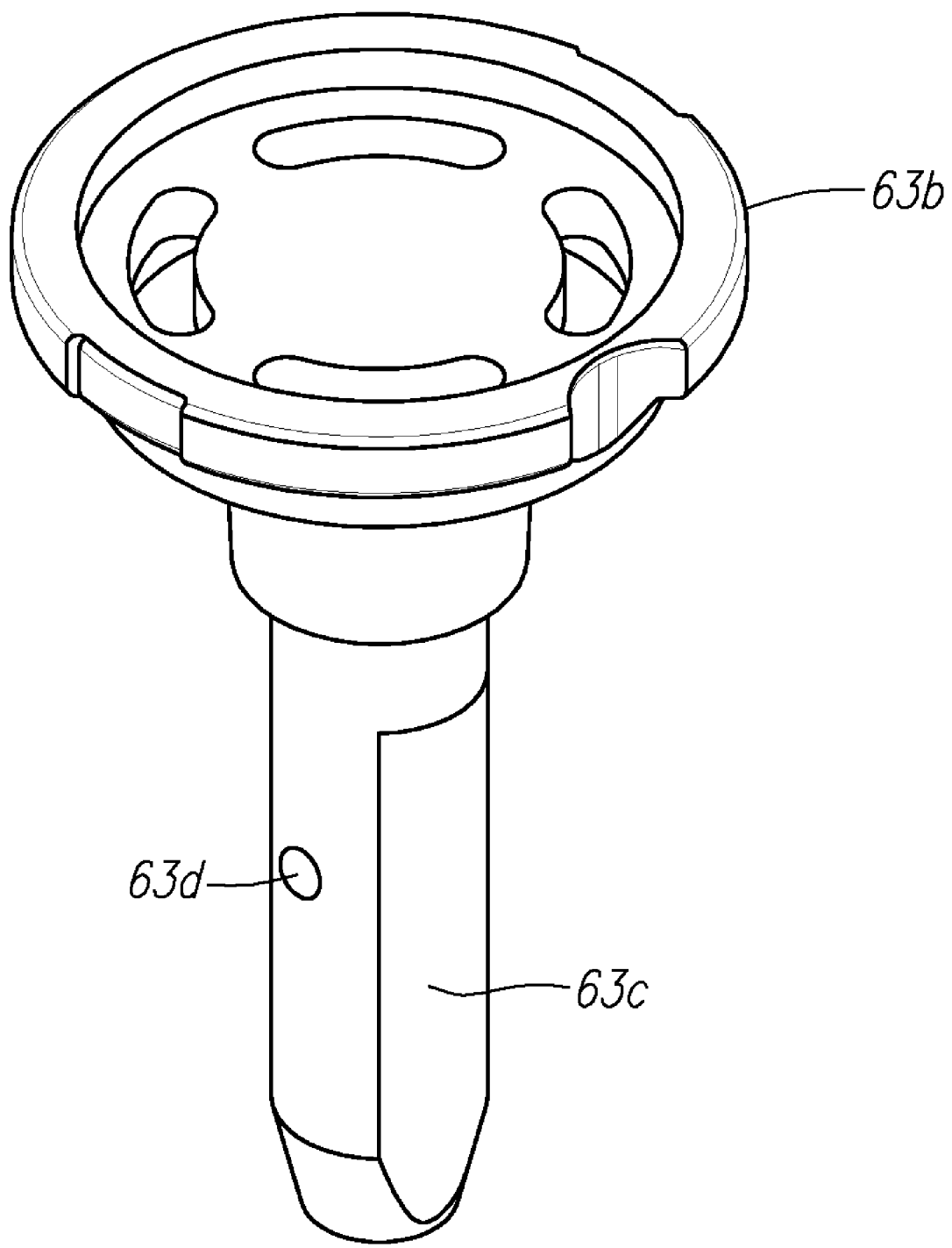
FIG. 6R is a perspective view of the drive shaft shown in FIGS. 6P-Q illustrating a flat edge of one side of the drive shaft.
Figure 6S:
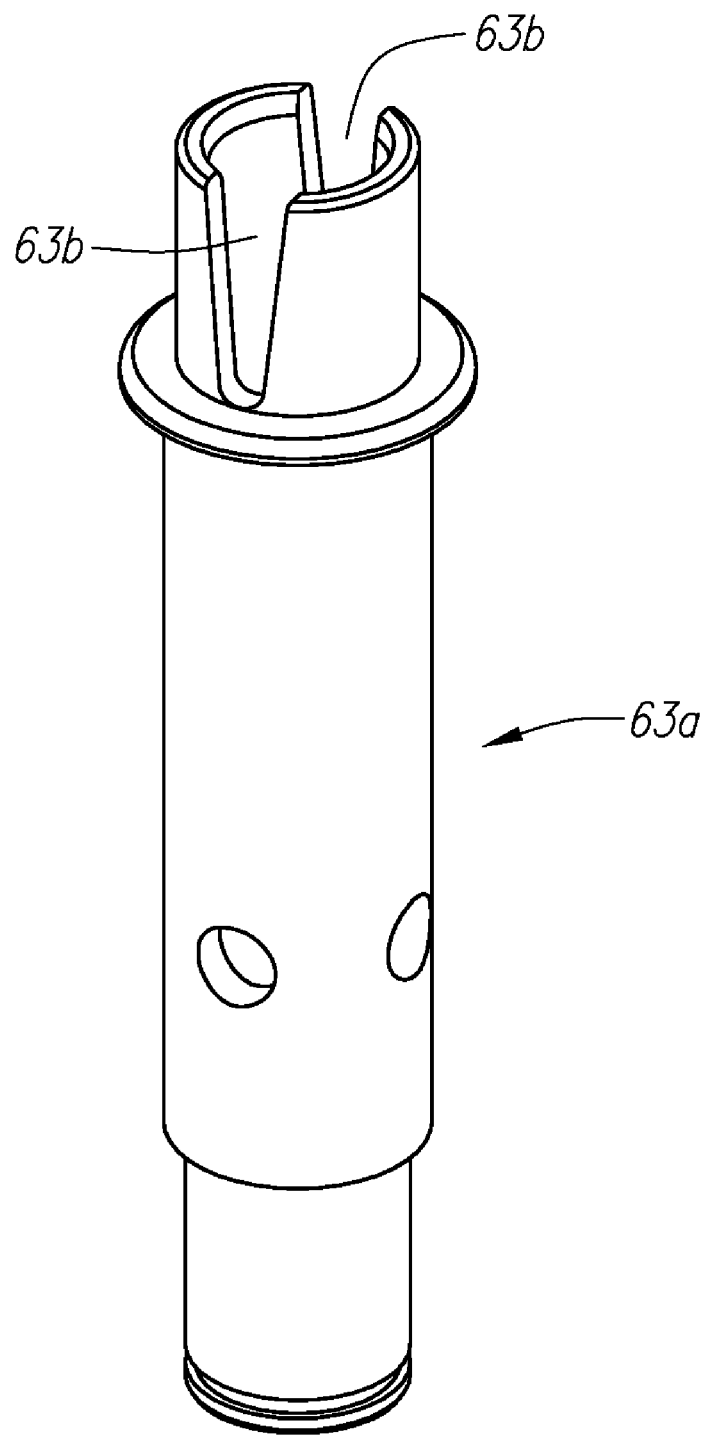
FIG. 6S is a perspective view of a sleeve receptacle or receiver slot configured to receive an end of a drive shaft.
Figure 6T:
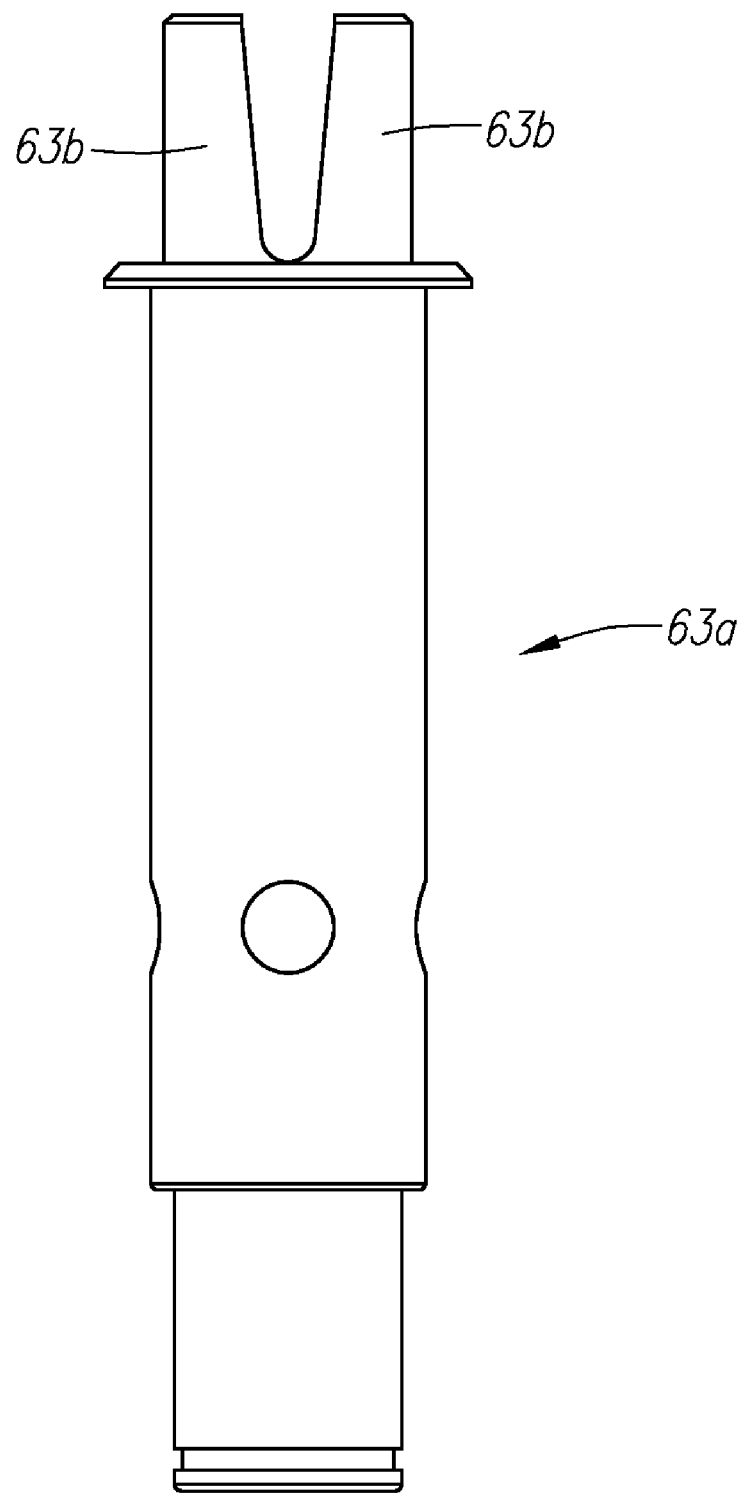
FIG. 6T is a side view of the sleeve receptacle shown in FIG. 6S.

More particularly, referring to FIGS. 6N-O, a receiver slot or sleeve receptacle (63a) extends from the instrument driver (16) and is designed to receive the drive shaft (61a) of a catheter splayer (61). FIG. 6N illustrates a drive shaft (61a) that is not inserted within the sleeve (63a), and FIG. 6O illustrates a drive shaft (1054) that is inserted within a sleeve (63a). The drive shaft (61a) may also be part of a pulley assembly. 1054) is a part of a pulley assembly (1231) (e.g., as shown in FIG. 5J).

With further reference to FIGS. 6P-T, illustrate alternate side views and a perspective of a drive shaft (61a) and its pulley assembly component (63b). In the illustrated example, the drive shaft (61a) has a flat edge (63c) on one side of its cylindrical surface such that when the drive shaft (61a) is viewed along its longitudinal axis, the shaft has the shape of a letter "D". It should be understood that other a drive shaft (61a) may include other cross-sectional shapes. The shaft (61a) has an opening (63d) through which a cross pin (63e) may be located. The drive shaft (61a) may be keyed such that a socket of the shaft (61a) is designed to fit or be received within a receiving sleeve (63a) having a certain shape. The sleeve (63a) in the illustrated example includes a pair of V-shaped or wing shaped notches (63f) to receive and hold the pin (63e) of a shaft (61a) as the shaft (61a) is inserted into the sleeve (63a). In the illustrated example, the sleeve (1082) does not employ capture pins, although such pins may be utilized.

During operation of the instrument driver (16), motors coupled to the sleeves (1082) are actuated to rotationally drive the sleeves (63a). A catheter assembly (30) with its splayer (61) mounted onto the instrument drive (16) would have its shafts (61a) positioned inside a plurality of corresponding sleeves (63a). As the sleeves (63a) are rotated, the pins (63e) of the shafts (61a) are seated in the V-shaped notches (63f) and are engaged by the rotating sleeves (61a), thus causing the shafts (61a) and associated pulley assemblies (63b) to also rotate. The pulley assemblies (63b) in turn cause the control elements (e.g., wires) coupled thereto to manipulate the distal tip of the catheter instrument (30) member in response thereto. To remove a splayer from the instrument driver in this implementation, less force is needed as the V-shaped notches (63f) allow for quick and easy disengagement of the shafts (61a) from the sleeves (63a).

Roll Correction

Embodiments directed to systems and methods for compensating or correcting for roll or rotational motion or twisting of a non-rigid or flexible catheter instrument (30) positioned within a sheath instrument (18), e.g., as a result of tension applied to control elements or pull wires, are described with reference to FIGS. 7A-G. In one embodiment, embodiments compensate for the torsional compliance of the catheter instrument (18) or portion thereof, e.g., a portion that is located distally relative to a keyed interface between an outer surface of the catheter (18) and an inner surface of the sheath (30) as a function of forces and torque applied to the catheter (18) and the position of the sheath (30). Embodiments for correcting for catheter (18) roll or torsional forces may involve compensating for forces on keyed components, or "backlash" compensation, and compensating for forces based on the angular arrangements of sheath (30) and catheter (18) components using, for example, a controller, software, hardware or a combination thereof.

More particularly, in a typical system (S), a non-rigid guide catheter instrument (18) having torsional compliance is coaxially disposed within the sheath (30). When the guide catheter instrument (18) is substantially straight and the sheath instrument (30) is bent or articulated the guide catheter (18) generally follows the bending action of the sheath (30) whether towards the anterior, posterior, medial, or later direction. However, when a sheath (30) is deployed in a bend and fixed in a location in space, and the guide catheter (18) extending outwardly from sheath (30) is articulated, the interactions between the guide catheter (18) and the sheath (30) may affect the behavior of the distal portion of the guide catheter (18) as a result of torsional forces on the catheter (18) that urge or cause the catheter (18) to twist or rotate. Embodiments advantageously compensate for these torsional forces to counter the rolling-type motion of the guide catheter (18).

Figure 7A:
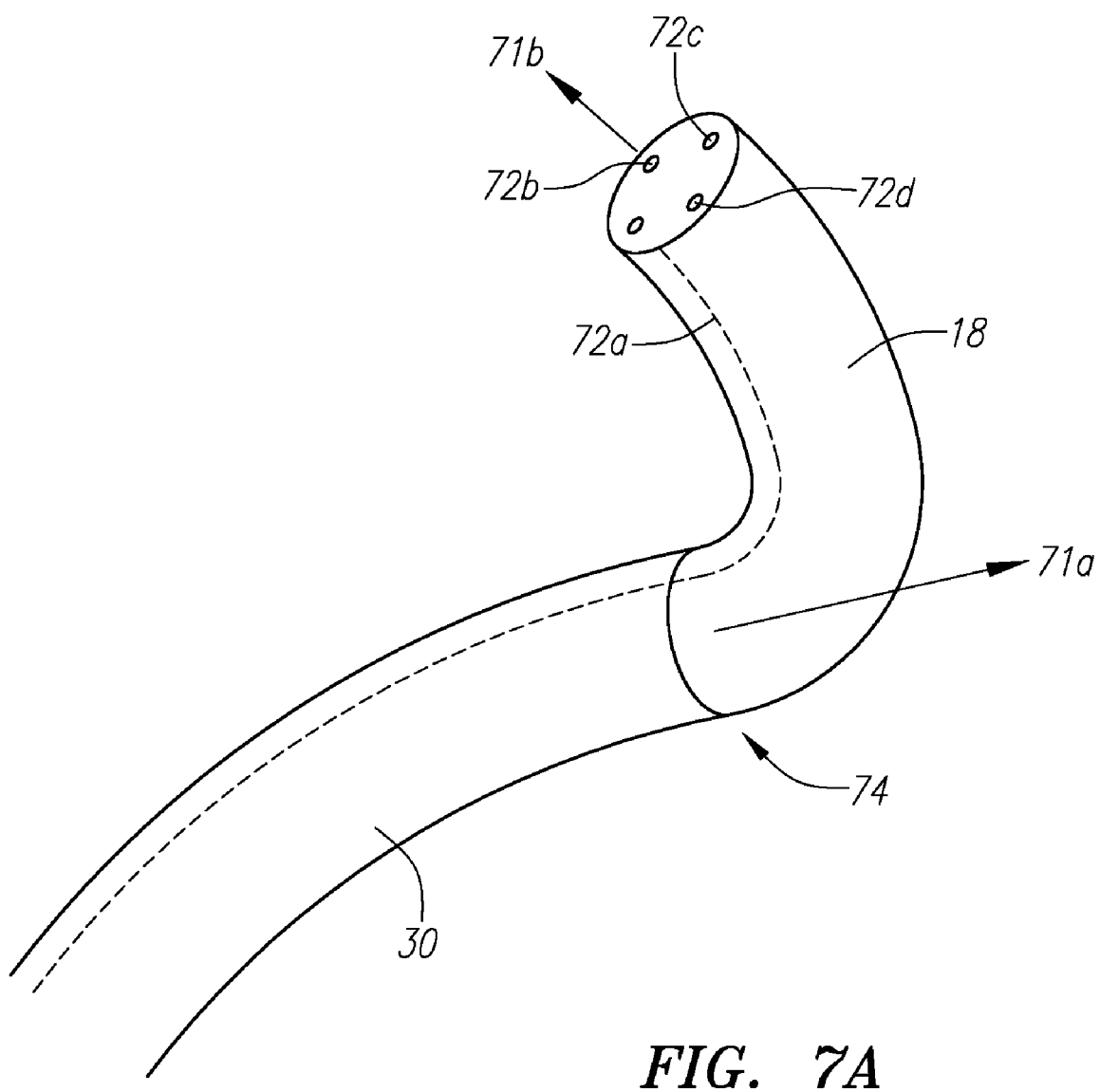
FIG. 7A illustrates a sheath and a guide catheter having four control elements bending upwardly and outwardly from the page in different directions in connection with explaining embodiments directed to compensating for rolling of the guide catheter within the sheath.

Referring to FIG. 7A, a sheath instrument (30) is shown as curving or bending upwardly and outwardly from the page towards the right (71a), and a guide catheter instrument (18) is shown as curving or bending upwardly and outwardly from the page, but towards the left (71b). In the illustrated example, the guide catheter instrument (18) includes four control elements such as pull wires 72a-d (generally 72). In order to bend the guide catheter instrument (30) as shown in FIG. 7A, the pull wire (72a) can be actuated.

By tracing back the path of pull wire (72a), it can be seen that the pull wire (72a) is bent and under a tension force, particularly at the interface (74) at the distal end of the sheath (18) as the sheath instrument (18) bends into a different plane relative to the guide catheter instrument (18) and the sheath (30) constrains the guide catheter (18). Since the pull wire (72a) is now located at the top of the guide catheter instrument (18), inside of the sheath (30), the pull wire (72a) encounters a certain contact force along that curvature. More specifically, the pull wire (72a) under tension will attempt to find a bottom of the resulting curve or bend, thereby generating a moment or twisting or torsional force on the catheter (18), which urges the catheter (18) to rotate.

As a result, the proximal section of the guide instrument (18) extends outwardly from the sheath instrument (30) and is subjected to torsional loading. In addition, a greater amount of tension force needs to be exerted at the proximal end of the pull wire (72a) to ensure that the desired bend is achieved. Thus, in such a configuration, the commanded position of the guide catheter instrument (30) may not match the actual position of the guide catheter instrument (30). In other words, when the sheath instrument (30) and the guide catheter instrument (18) are bending in different planes, the result may be an undesired torque moment. In some instances, when the guide catheter and sheath instruments (18, 30) are bending in different planes, the torsional forces applied to the guide catheter instrument (18) may urge or cause the guide catheter (18) to displace, for example by flopping over undesirably into one of the posterior or anterior half planes, or to rotationally displace, or roll, inside the sheath instrument (30), the results of which is a catheter (18) assuming an actual position that is not the desired or commanded position.

Figure 7B:
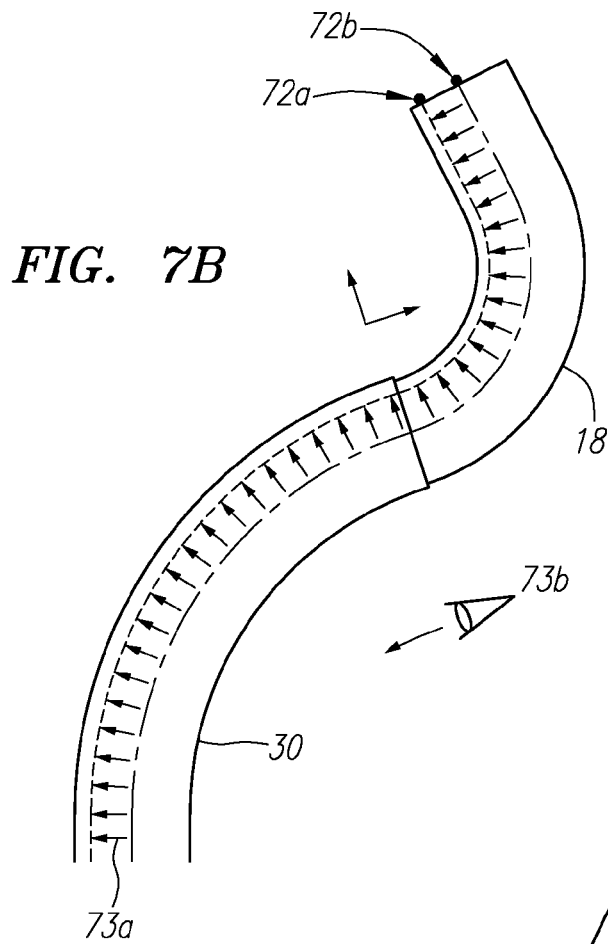
FIG. 7B illustrates a sheath bending within the plane defined by the page and a guide catheter caused to bend in a different direction than the sheath but within the same plane by tensioning a pull wire.
Figure 7C:
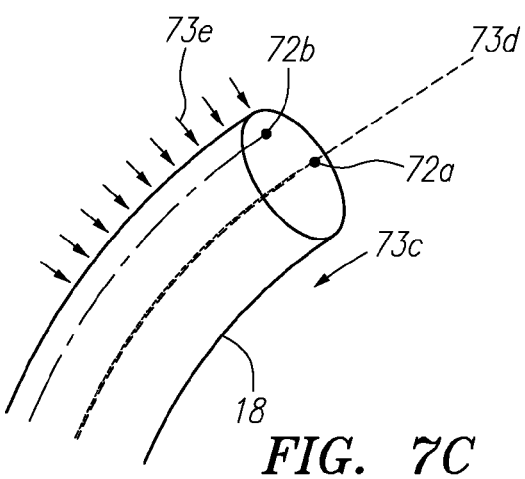
FIG. 7C is a cross sectional view into the guide and sheath instruments illustrated in FIG. 7B as viewed from a point of reference in FIG. 7B.
Figure 7D:
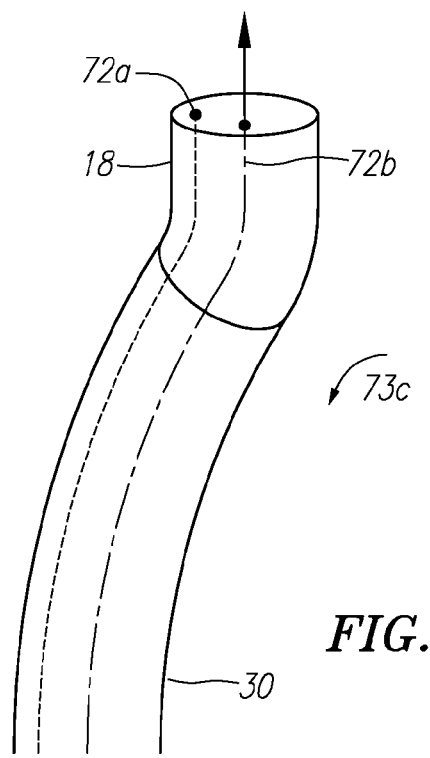
FIG. 7D illustrates the assembly of 7B. in which the guide catheter is bent upwardly and outwardly from the page in a direction indicated by a curved arrow to illustrate possible flopping of the guide catheter over into the anterior or posterior half plane.

FIGS. 7B-D further illustrate the bending of sheath (30) and guide catheter (18) shown in FIG. 7A. In FIG. 7B, the sheath instrument (30) is shown as bending within the plane defined by the page. The guide catheter instrument (18) is caused to bend in a different direction than the sheath instrument (30) within the same plane by tensioning pull wire (72A). Contact forces (73a) created along the guide catheter instrument (18) on the pull wire (72A) may attempt to shift the sheath instrument (30), especially at proximal portions of the guide catheter instrument (18) located within the sheath instrument (30).

FIG. 7C is a cross sectional view into the guide and sheath instruments (18, 30) as viewed from the point of reference (73b) of FIG. 7B. As shown in FIG. 7C, the pull wire (72b) is illustrated as positioned on the right hand side of the cross section, and the bend plane is defined as perpendicular into the page. By tensioning pull wire (72b), the guide catheter instrument (18) may be caused to bend outwardly from the page plane as defined in FIG. 7B. The direction of bend (73c) in FIG. 7B is upward and towards the left. In the illustrated example, the pull wire (72a) that is used to bend the guide catheter instrument (18) within the page plane is located along the line of action (73d) that extends longitudinally through the center of the guide catheter instrument (18). The second pull wire (72a), however, is located above the line of action (73d) in FIG. 7B and results in contact forces (73e) that push the pull wire (72b) towards the line of action (73d) to decrease the offset from center. As a result, the guide catheter instrument (18) may begin to twist and/or roll due to the torsional forces applied to the catheter instrument (18). FIG. 7D illustrates the assembly shown in FIG. 7B in which the guide catheter instrument (18) is bent upwardly and outwardly from the page in the direction indicated by curved (73c). Because the sheath and guide catheter instruments (18, 30) bend in different planes in this instance, the guide catheter instrument (18) may flop over into the anterior or posterior half plane by a certain degree.

Figure 7E:
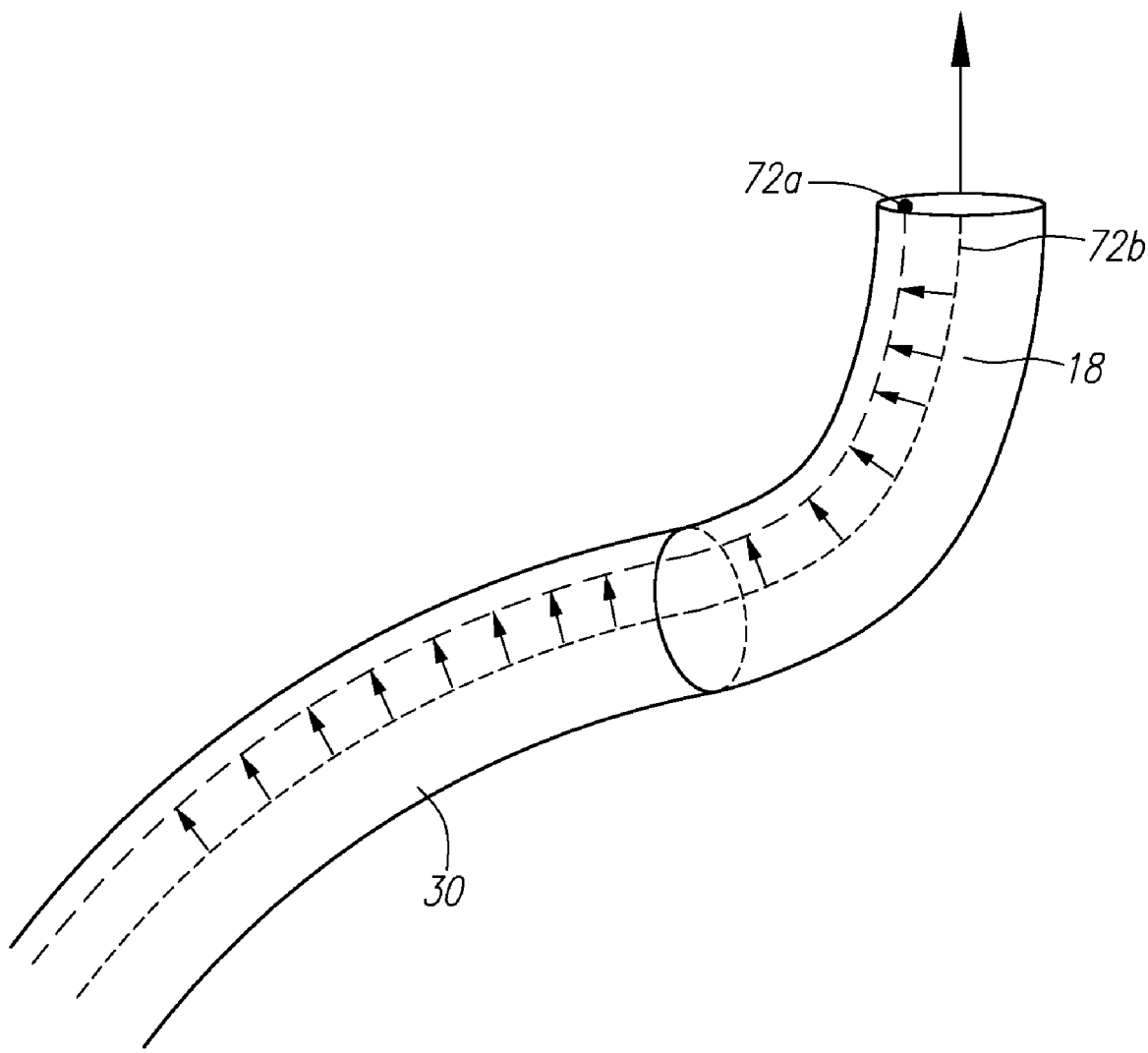
FIG. 7E a sheath and guide catheter bending within the same plane as defined by the page and a pull wire that is actuated to bend the guide catheter.

However, referring to FIG. 7E, if the sheath and guide catheter instruments (18, 30) bend in the same plane, then this discrepancy does not occur and the guide catheter and sheath instruments (18, 30) bend within the same plane as defined by the page. In the illustrated example, the pull wire (72A) is actuated to bend the guide catheter instrument (18). Tracing along the length of the pull wire (72A), arrows indicate the contact forces that exist along the pull wire (72A). In this instance, the contact forces along segment of the guide catheter instrument (18) within the sheath instrument (30) encourage the sheath (30) to bend in that direction.

However, if the guide catheter instrument (18) is actuated to bend outwardly from the plane, then the line of action is no longer along the center line of the guide catheter instrument (18), and the guide catheter (18) begins to twist and roll as the pull wire (72B) is torqued. Thus, whenever a guide catheter instrument (18) is constrained by a sheath instrument (18) and its curvature inside the sheath (18) is above the center, pulling on one of the pull wires (72) of the guide catheter (18) will cause the guide catheter (18) to twist. This torsion bias condition occurs in the anterior half plane and the posterior half plane whenever the guide catheter (18) is bending in a different plane than the sheath instrument (30).

Figure 7F:
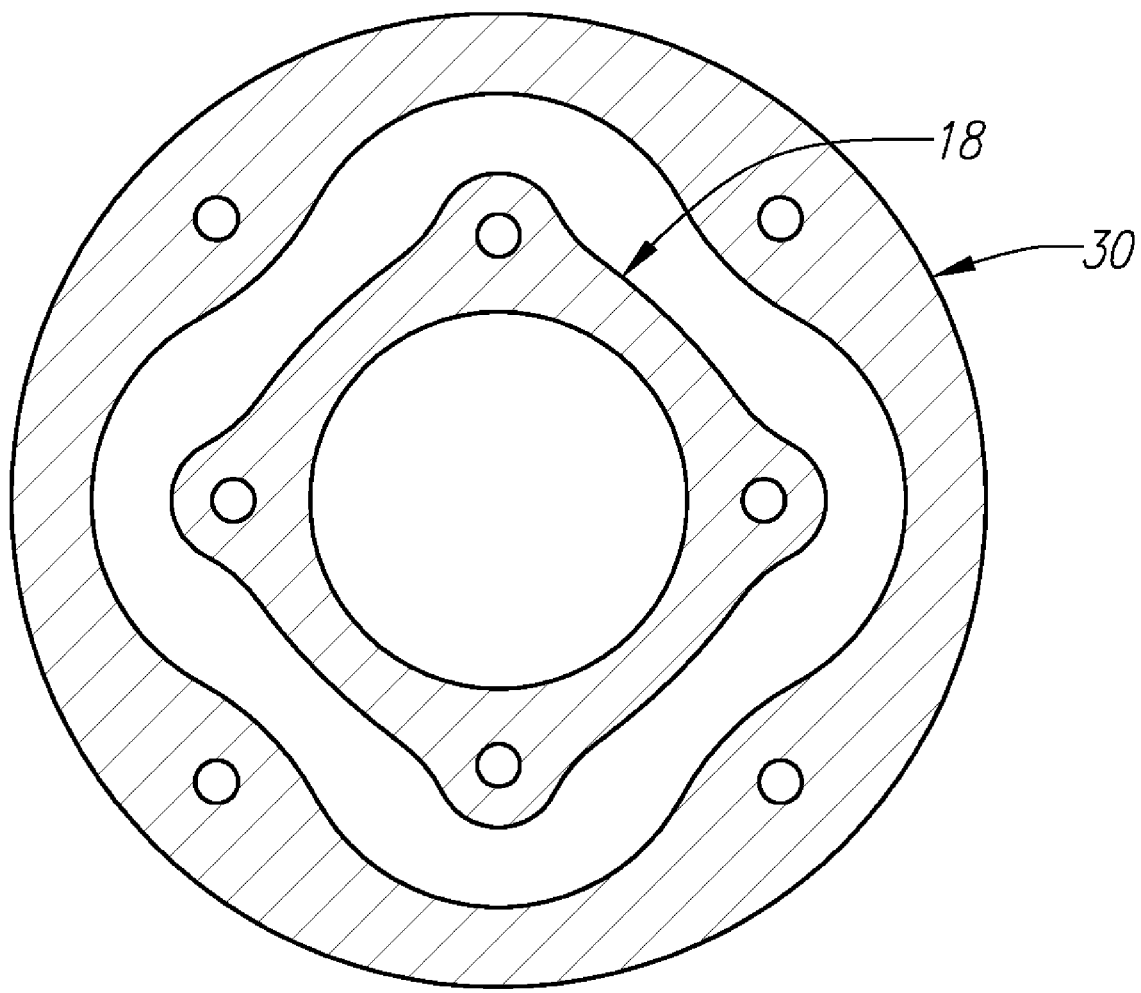
FIG. 7F is a cross-sectional view of sheath having an outer surface that is keyed with an inner surface of a guide catheter instrument.

One solution for countering or compensating for these torsion forces or bias and urging of the guide catheter instrument (18) to twist is to key the sheath and guide catheter instruments (18, 30), e.g., as shown in FIG. 7F and described in further detail in U.S. patent application Ser. No. 11/481, 433, the contents of which are incorporated by reference above. As shown in FIG. 7F, the outer surface of the guide catheter instrument (18) and the inner surface of a sheath instrument (30) have non-circular shapes that form a key or shaped interface that is intended to prevent or reduce rotation of the guide catheter instrument (18) within the sheath (30).

In the example shown in FIG. 7F, the interior of the sheath instrument (30) defines grooves that make contact with keyed portions of the guide instrument (18). In one implementation, the guide catheter instrument (18) can initially have a circular profile, then become more square as the control lumens and outer coating are applied during manufacturing. In this implementation, as the guide catheter instrument (18) begins to roll or twist, the keyed interface between the guide catheter instrument (18) exterior and sheath instrument (30) interior will stop the twisting motion, thereby compensating for any movement or "slop" between these components. Slop caused by the twisting action may also be actively compensated by rolling the guide catheter instrument (18) back to the desired position in some instances.

However, keying between the sheath (30) and the catheter (18) may not be perfect, and issues may arise due to keying misalignments. Similarly, issues may also arise even when the sheath and guide catheter instruments (18, 30) are correctly aligned and centered, but there is too much play between the instruments (18, 30). As a result, the guide catheter instrument (18) may still rotate relative to the sheath instrument (30) due to torsional forces applied to the catheter instrument (18).

In one embodiment, the sheath instrument (30) may be designed with sufficient rigidity to maintain its shape and resist these torional forces. As a result, the sheath (30) will maintain its position and reduce, minimize or eliminate rolling of the catheter instrument (18) within the sheath (30).

In another embodiment, one or more control elements or pull wires of the sheath (30) may be actuated or placed in tension to compensate for these contact forces (73a) such that the distal tip of the catheter instrument (18) is at or closer to the expected or commanded position. Thus, the undesired slop or motion resulting from torsional compliance of the guide catheter instrument (18) can be compensated by actively rolling back the guide catheter instrument (18) by manipulating sheath control elements or pull wires. Thus, active compensation can reduce and/or equalize forces on keyed components of the guide catheter instrument (18) and the sheath instrument (30) such that the guide catheter (18) does not roll inside of the sheath (18) and will not flop over the posterior and anterior half planes.

Figure 7G:
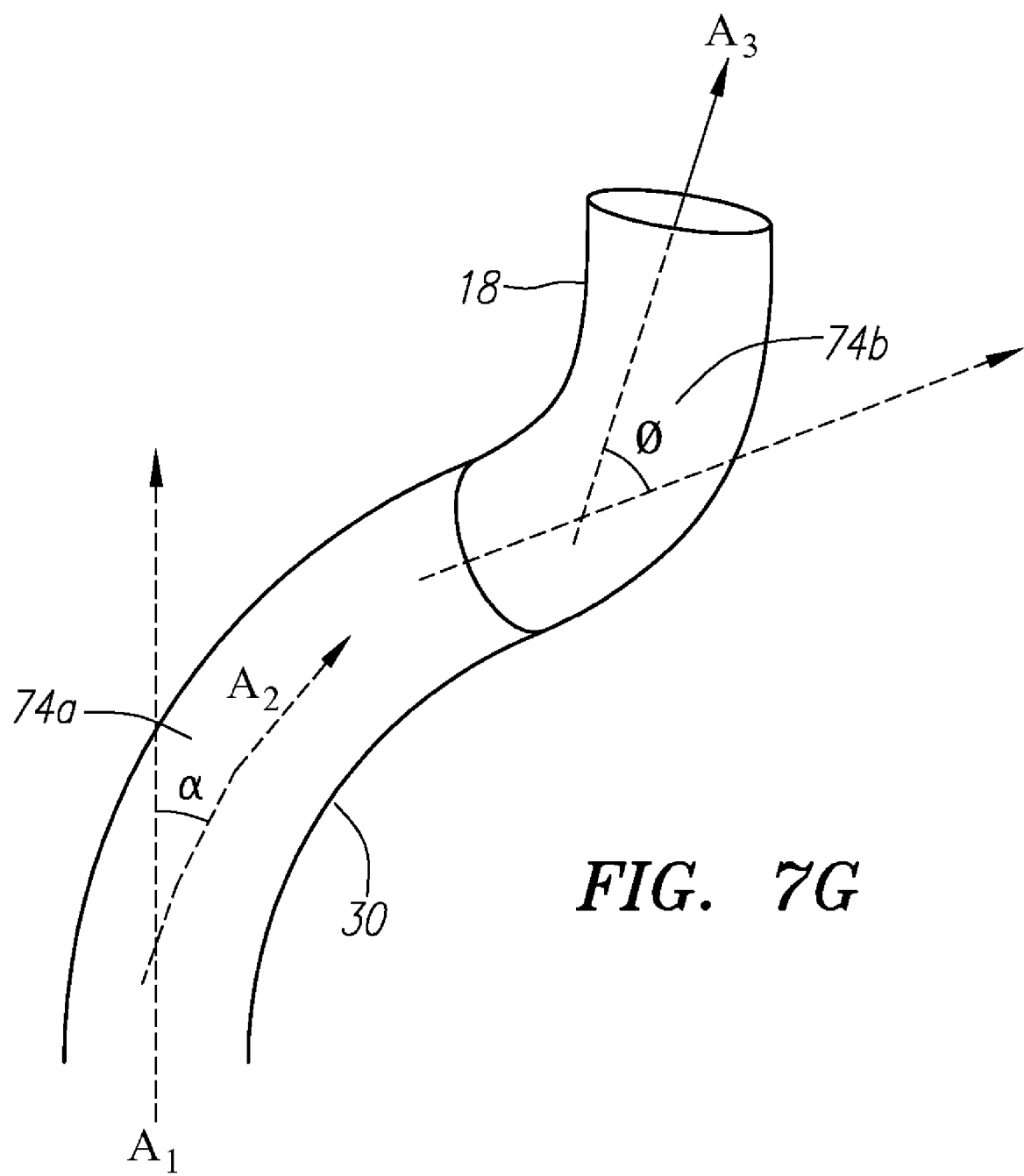
FIG. 7G illustrates angular relationships between sheath and guide catheter instruments for use in compensating or correcting for roll of the inner guide catheter instrument without the outer sheath instrument.

Referring to FIG. 7G, another embodiment of compensating for torsional compliance of the guide instrument (18) involves adjusting the guide instrument (18) articulation by generating a compensation output based on inputs of angular arrangements of the sheath (18) and catheter (30) components, e.g., using controller, hardware, software, or a combination thereof. As shown in FIG. 7G, the sheath instrument (30) bends towards the right hand side within the page plane, and the catheter instrument (18) bends upwardly and outwardly from the page plane. By analyzing factors such as the desired bend curvature, the bend plane, the desired position of the tip of the catheter instrument (18), torsional stiffness of the catheter instrument (18), and other instrument attributes, the amount of flop or motion that may occur and the amount of roll correction that is necessary can be determined.

As discussed above, when the sheath and catheter instruments (18, 30) bend within the same plane, roll correction may not be needed because the lines of action are right on center. However, as the guide catheter instrument (18) bends further and outwardly from the plane such that it approaches 90° vertically out of the page plane, a maximum amount of correction may be needed. Thus, in one embodiment, the amount of roll correction to be applied is a minimum at zero articulation, and a maximum at +/−90° articulation. The amount of compensation may also depend on the amount of sheath (18) articulation. More particularly, in one embodiment, if the sheath instrument (18) is straight, then the curvature of the pull wires of the catheter instrument (30) within the sheath instrument (18) can be zero, and the pull wires are straight. Thus, no contact load is present to cause rolling or twisting of the guide catheter (30).

As shown in FIG. 7G, a first center line or axis (A1) is defined along the longitudinal axis of the sheath instrument (30). The sheath (30) is bent to define a second center line or axis (A2). The degree to which the sheath (30) is bent is shown as an angle α (74a) defined between the first and second axes (A1, A2). A third center line or axis (A3) is defined along the longitudinal axis of the guide catheter instrument (18). An angle θ (74b) is defined between the second and third center lines or axes. According to one embodiment, the amount of roll correction β of the rotational position of the catheter instrument (18) that is required given the angles α (74a) and angle θ (74b) as shown in FIG. 7G is expressed as:

$$\beta = K \sin(\theta) \sin(\alpha)$$

wherein K is a tuning gain factor, θ (74b) is the angle at which the guide catheter (18) is bent, and α (74a) is the angle at which the sheath instrument (18) is bent. In one embodiment, the tuning gain factor K is programmed into a memory device associated with the guide splayer (61). Other sheath/guide instrument (18, 30) characteristics may also be stored to memory, e.g., at the time of manufacture.

Thus, in this embodiment, if the sheath (18) is straight, then the angle α (74a) is 0° and, and sin(0°) is also zero, resulting in no roll correction. However, if the sheath (18) bends at an angle α (74a) of 90°, then sin(90°) is one, and the amount the roll correction depends on the degree of bending of the guide catheter instrument (30).

With regard to the degree of bending of the guide catheter instrument (30), as long as the guide catheter (30) is within the same bend plane as the sheath (18), then the angle θ (74b) remains zero, and sin(0°) is zero, resulting in no correction even though the sheath (18) is fully articulated. However, as the guide catheter (30) begins to bend outwardly from the bend plane of the sheath (18), the angle θ (74b) increases until it is a maximum 90°. When the sheath (18) is articulated to 90° and the guide catheter (30) is articulated to 90° out of the sheath (18) bend plane, the roll correction factor β is a maximum value.

Thus, embodiments directed to roll correction advantageously allow the rotational position and direction of the guide instrument (30) to be controllably adjusted, whereas conventional systems and methods lack such controls, possibly leading to the guide catheter instrument flopping over as it bends. Embodiments of heuristic roll correction can be implemented in system software so that the compensation is automatically calculated by the system during system operation and can be used to supplement guide catheter (30) control. In one embodiment, the angle of sheath (18) articulation, the angle of guide (30) articulation, and the relevant bend planes are monitored.

In another embodiment, roll correction can be implemented by directly calculating the exact control forces present at the distal portion of the guide catheter (30) based on the bend curvature and the amount of force that is necessary to compensate for those control forces. One manner in which this embodiment may be implemented is by numerically solving differential equations. While this alternative approach may not be ideal as a real time solution, it may be useful for offline activities such as planning of the surgical procedure beforehand and building a map of accessible areas of the anatomy.

Further, while embodiments are described with reference to roll correction or compensation for sheath and guide catheter instruments (18, 30) having a keyed interface, embodiments can also be applied to non-keyed instruments (18, 30), e.g., when using a catheter instrument (18) having greater torsional stiffness.

Catheter Tip Hotness Compensation

Figure 8A:
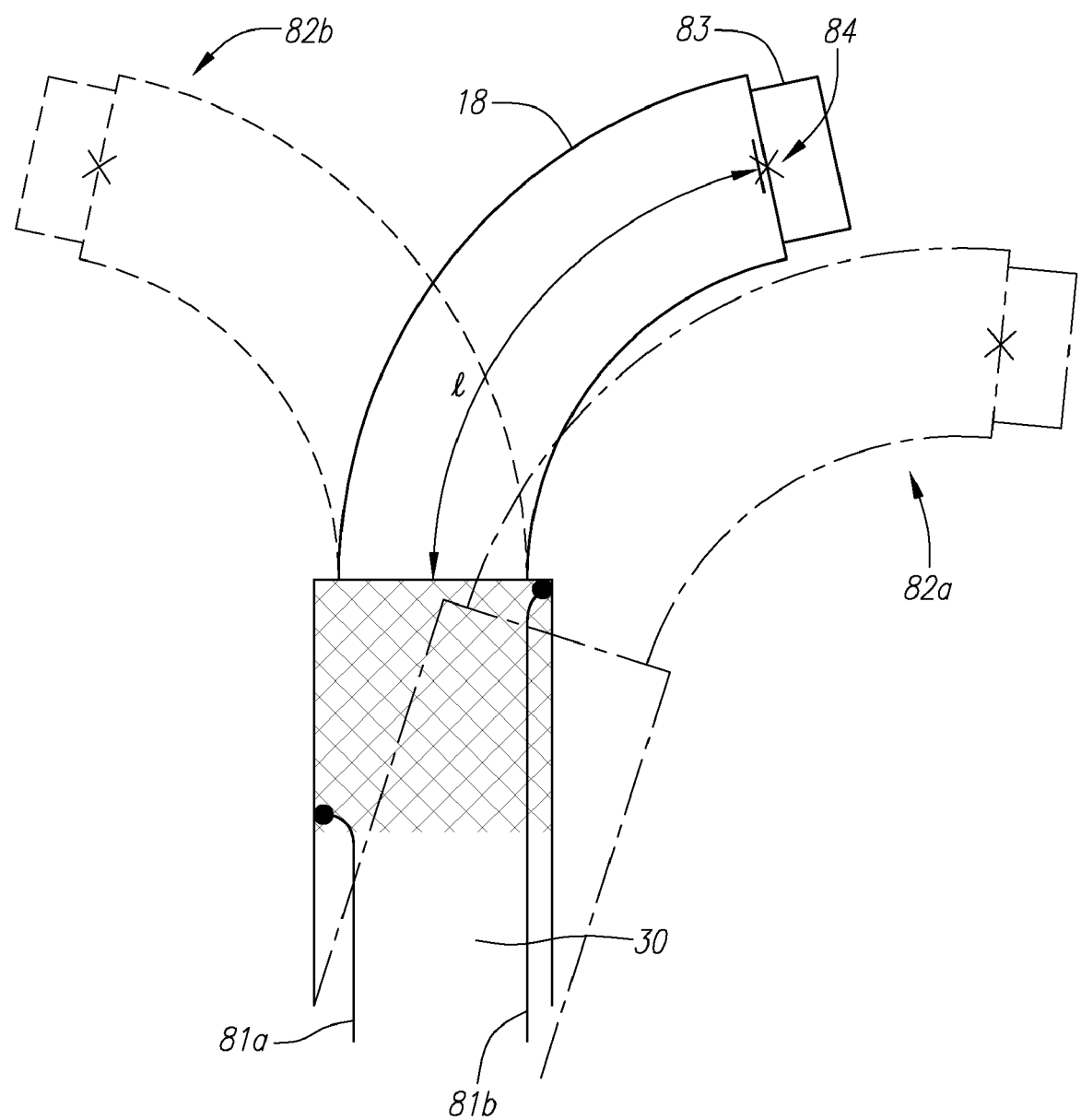
FIG. 8A is a side view of a sheath instrument deployed with zero articulation and different angular configurations of a guide catheter instrument and the resulting impact on the position of the sheath instrument in connection with explaining an embodiment directed to compensating for catheter tip hotness depending on how far the distal tip is extended from the distal end of the sheath instrument.

Referring to FIG. 8A, another embodiment is generally directed to systems and methods for compensating for catheter (18) tip hotness, or the degree to which the actual curvature or position of the distal portion or tip of the flexible catheter (18) deviates from an expected or commanded curvature or position as a result the coupling or forces between the catheter (18) and a flexible guide catheter (18), which vary depending on the length of the distal portion of the catheter (18) that extends beyond the distal end of the sheath instrument (30). Embodiments advantageously address these inconsistencies by compensating the amount of articulation depending on the extension of the distal end of the guide catheter (18) beyond the distal end of the sheath instrument (30). In one embodiment, the compensation (reduction in articulation) is greater when the coupling between the sheath instrument (30) and the catheter instrument (18) is the greatest, e.g., when the catheter instrument (18) is retracted into the sheath instrument (30) or extends from the sheath instrument (30) by a small amount. Compensation (reduction in articulation) is less or at a minimum (if any) in instances involving the least coupling between the sheath instrument (30) and the catheter instrument (18), e.g., when the catheter instrument (18) is fully extended from the sheath instrument (30).

FIG. 8A illustrates a sheath instrument (30) deployed with zero articulation and a guide catheter instrument (18) that is located coaxially within the sheath (30). A distal portion of the guide catheter instrument (18) extends and articulates outwardly from the distal tip of the sheath instrument (30). The sheath instrument (18) can be considered to be a rigid structure that constrains the proximal portion of the guide catheter instrument (30). However, during actual use, this model or assumption may not accurately reflect the manner in which the guide catheter (30) bends or is manipulated due to forces imparted on the sheath (18) by the guide catheter (30) which, in turn, cause the sheath (18) to bend undesirably, thereby changing the curvature or position of the catheter instrument (18). The degree to which the catheter instrument (30) causes this unintentional bending of the sheath instrument (18) is referred to as the "hotness" of the distal tip of the catheter instrument (30). The distal tip is "hotter" when it causes more deviation or bending of the sheath (18).

This "hotness" effect may be more pronounced when the guide (18) is almost fully retracted into the sheath (30), and less pronounced when the guide catheter (18) is substantially or fully extended from the sheath (30), in which case the degree of coupling between the guide catheter (18) and the sheath (30) is less than when the guide catheter (18) does not extend from the sheath (30), or does so by a small amount. In other words, when the catheter instrument (18) is retracted into the sheath (30), for example, forces upon and motion of the catheter (18) have a larger impact on and coupling with the sheath (30) and sheath (30) position, resulting in a "hotter" distal tip of the catheter (18) since it has more of an impact on the distal end of the sheath (30).

Thus, when the guide catheter (18) is fully retracted or is almost fully retracted, relatively small motions of the master input device (MID) (12) used to control the catheter instrument (18) may result in large swings of curvature at the distal tip of the sheath (30) because curvature is related to the amount of force seen at the distal tip. The distal tip of the sheath (18) may swing back and forth in response to these large forces. This effect may be more pronounced if a tip extension (83) is added to the distal tip of the guide catheter (18) or when a working catheter is deployed out the guide (18) distal tip.

With embodiments, the "hotness" of the distal tip of the catheter (18) can be compensated using a mechanics model, manipulation of sheath pull wires, scaling, and using more rigid sheath materials. In one embodiment, a mechanics model of the sheath (30) is used to determine how forces on the sheath (30) should be adjusted, e.g., by manipulating a pull wire of the sheath (30). In another embodiment, a hybrid mechanics model of the sheath (30) and guide catheter (18) may be used to determine how forces on the sheath (30) and/or guide catheter (18) should be adjusted. An example of a suitable mechanics model for use in embodiments is described in U.S. Utility patent application Ser. No. 12/022,987, filed Jan. 30, 2008, which is incorporated by reference in its entirety herein. In another embodiment, one or more control elements or pull wires of a sheath instrument (30) can be manipulated to counter the forces that are coupled to the sheath (30) by the catheter (18) when the distal tip of the catheter (18) does not extend beyond the distal end of the sheath (30) or extends beyond the distal end of the sheath (30) by a small amount, e.g., by less than about one to about two inches. Thus, if a sheath (30) is pulled to the left, a pull wire of the right side of the sheath (30) can be placed in tension to urge or move the sheath (30) back to the right to assume its original or intended position.

However, with this embodiment, full actuation of the sheath instrument (18) may not be possible due to, for example, the sheath (18) having limitations related to the pullwire configuration in a particular scenario. For example, the sheath (18) shown in FIG. 8A is illustrated as including a first pull wire (81a) that terminates at a first location within the sheath (18) and a second pull wire (81b) that terminates at a second, distal point, e.g., at the distal tip of the sheath (18) as illustrated. In the illustrated example, if the guide catheter instrument (18) articulates to the right (82a), the distal tip of sheath (30) is caused to follow the guide catheter (30) and also flexes to the right. With the arrangement of sheath pull wires (81a-b) in this example, the control wires (81a-b) may not be able to correct this flexing action. However, if the guide catheter (18) articulates to the left (82b), the distal tip of the sheath (30) is caused to flex to the left. In this instance, the distal pull wire (81b) may be actuated to straighten the sheath (18) distal tip and to compensate for this flexing motion. In both cases, the undesired flexing action of the sheath (30) is increased as the guide catheter (30) is articulated to a greater degree. Thus, the movement of the distal tip of the sheath (30) may also be more pronounced when a working catheter is deployed out the guide catheter (18).

Figure 8B:
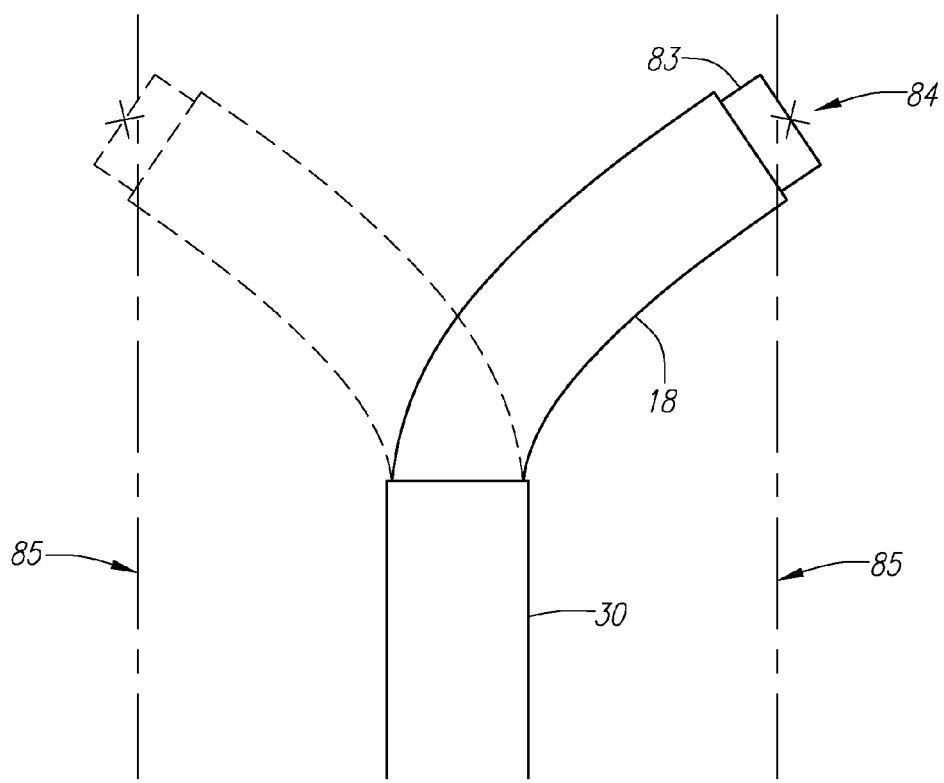
FIG. 8B illustrates a range of swinging motion of a distal portion of a guide catheter instrument where the point of control is at the very distal tip of the combined guide catheter structure.

As shown in FIG. 8A, the point of control (84) for the guide catheter (30) is defined at the distal tip of the guide catheter (30), as opposed to at the distal tip of the extension (83). As shown in FIG. 8B, the point of control (84) is at the distal tip of the combined structure of the guide catheter (18) and the extension (83), i.e., at the distal tip of the extension (83). FIG. 8B illustrates the range of swinging motion of a guide catheter (18) when the point of control (84) is at the distal tip of the combined guide catheter (18) structure. In this example, if the MID (12) is moved slightly back and forth, the distal tip of the combined structure including the guide catheter (30) and the extension (83) may swing back and forth in between a region of space defined by lines (85).

Figure 8C:
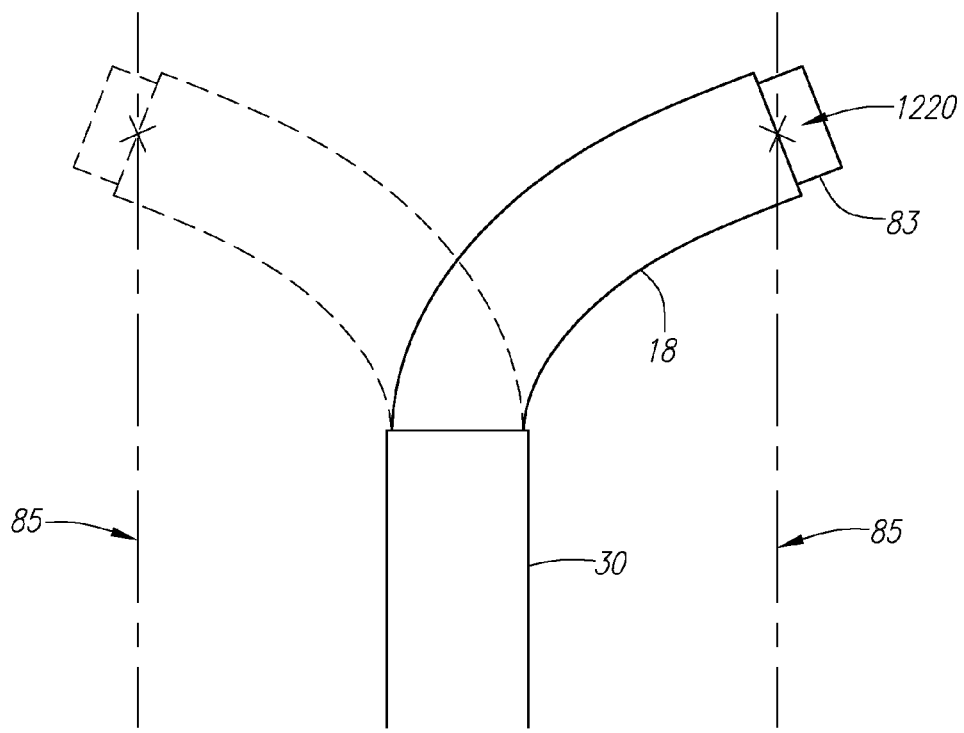
FIG. 8C illustrates the range of swinging action of a distal portion of a guide catheter instrument where the point of control is at the guide distal tip rather than at the end of the combined guide structure as shown in FIG. 8B.

FIG. 8C illustrates the range of swinging action for a guide catheter (18) where the point of control (84) is at the distal tip of the guide catheter (30) (e.g., as shown in FIG. 8A), rather than at the distal tip of the combined structure (as shown in FIG. 8B). When the MID (12) is moved for this configuration, the point of control (84) still swings back and forth to the limits defined by lines (85) like the embodiment shown in FIG. 8B, except that because the stiff tip extension (1220) extends beyond the distal tip of the guide catheter (30), that length is not accounted for and may undesirably protrude beyond the expected range of motion, thereby resulting in an unintended, wider swing. As a result, the operator may observe a larger amount of swinging motion than expected depending on what extends distally beyond the point of control and by what length. One embodiment compensates for these effects by utilizing a sheath (30) that includes control wires for compensating for flexing and swinging actions.

In another embodiment, the guide catheter (30) controls may be adjusted such that the point of control (84) is at the distal tip of the combined catheter assembly structure (including 30, 83) as described with reference to FIG. 8B. This embodiment may involve an understanding of the inverse kinematics and solving the mathematics relating to a stiff tip extension or working catheter. In one embodiment, a model is created to simulate the dynamics of the guide catheter (30) and to allow for the modular addition of tip portions of varying lengths.

A further embodiment is directed to a method for compensating for the hotness of the distal tip of the guide catheter (18) by scaling down the amount of commanded catheter (18) movement based on how far the guide catheter (18) is retracted into the sheath (30). In one embodiment, the scaling factor is applied primarily when the guide catheter (18) is fully or substantially retracted within the sheath (30), i.e., it extends from the sheath (30) by a small amount. According to one embodiment, the filtered or compensated curvature $K_F$ for the guide catheter (18) instrument can be defined as:

$$K_F = a * K_C$$

where $K_C$ is the commanded, filtered or adjusted curvature and "a" is a scaling factor. According to one embodiment, the scaling factor "a" is a non-linear function that is based on the insert length "l", i.e., the length of the guide catheter (18) that extends beyond the distal tip of the sheath (30) as illustrated in FIG. 8A. In one embodiment, the scaling function a(l) is expressed as:

$$a(l) = 1 - \frac{1-b}{1 + \frac{l^c}{d}}$$

wherein "b", "c", and "d" are tuning factors for shaping the curve of the non-linear function. In one embodiment, b=0 to represent a zero scale for zero insert, exponent c=3 to represent how fast to ramp up the scaling as the insert length increases, and gain or application factor d=2000 to represent a ratio of scaled growth.

Figure 8D:
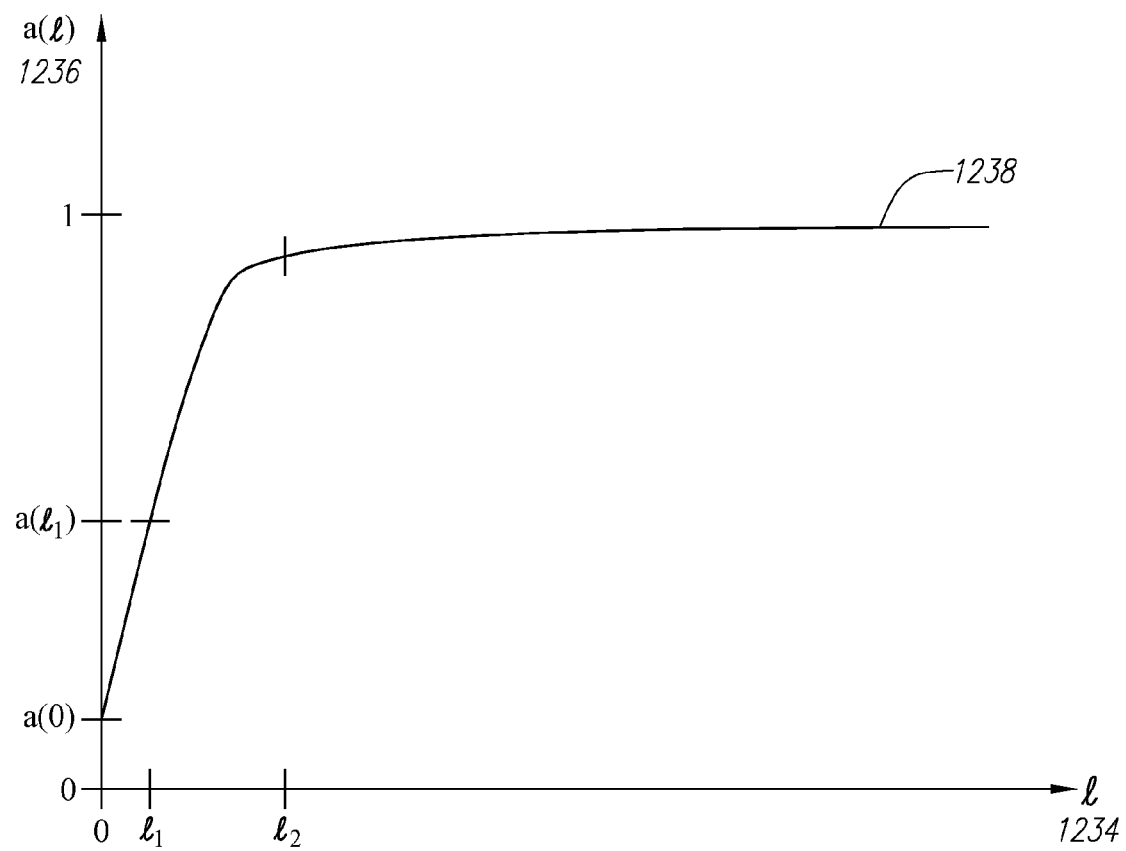
FIG. 8D is a graph illustrating variables of a method for compensating for catheter tip hotness based on scaling, wherein a scaling factor a varies as a function of a length l of a distal portion of the catheter that extends outwardly beyond a distal end of the sheath instrument.

FIG. 8D illustrates a graph (1238) of the scaling factor a (1236) (y axis) varying as a function of length l (1234) (x axis) of the distal part of the guide catheter (30) that extends beyond the distal tip of the sheath (18) in one embodiment. In the illustrated example, when the insert length l (1234) is zero, the scaling factor (1236) a(0) is a small non-zero amount. Thus, when the length l (1234) is small, the commanded articulation $K_C$ is reduced to $K_F$, but as the length l (1234) increases, i.e., the guide catheter (18) is extended further beyond the distal end of the sheath (30), then the ratio or scaling factor (1236) approaches one, indicating that the commanded curvature $K_C$ is fully driven or articulated (i.e., compensated to a lesser degree). This example also illustrates that the scaling factor a (1236) increases rapidly as the guide catheter (30) is extended from the sheath (18) until a predetermined length, at which point the commanded articulation does not need to be scaled down or compensated.

In yet another embodiment, the stiffness of the sheath (30) can be actively adjusted such that the stiffness of the sheath (30) changes depending on the extension of the distal tip of the guide catheter instrument (18) beyond the distal tip of the sheath (30). Thus, the sheath (30) is actively controlled to be stiffer when the distal tip of the catheter (18) does not extend beyond the distal end of the sheath (30) or extends beyond the distal end of the sheath (30) by a small amount, e.g., by less than about one to about two inches, and less stiff when the catheter (18) is extended by a larger degree, e.g., more than about two inches, or fully extended.

Insertion Force Indicator

Referring to FIGS. 9A-G, a further embodiment is directed systems and methods for indicating catheter (30) insertion forces. When the guide catheter (30) extends from the sheath (18) and makes contact with tissue, a certain force F is imparted onto the guide catheter (30). Depending on how far the distal tip (92) of the guide catheter (30) is extended from the sheath (18), the force F may result in different interactions between the guide catheter (18) and tissue.

Figure 9A:
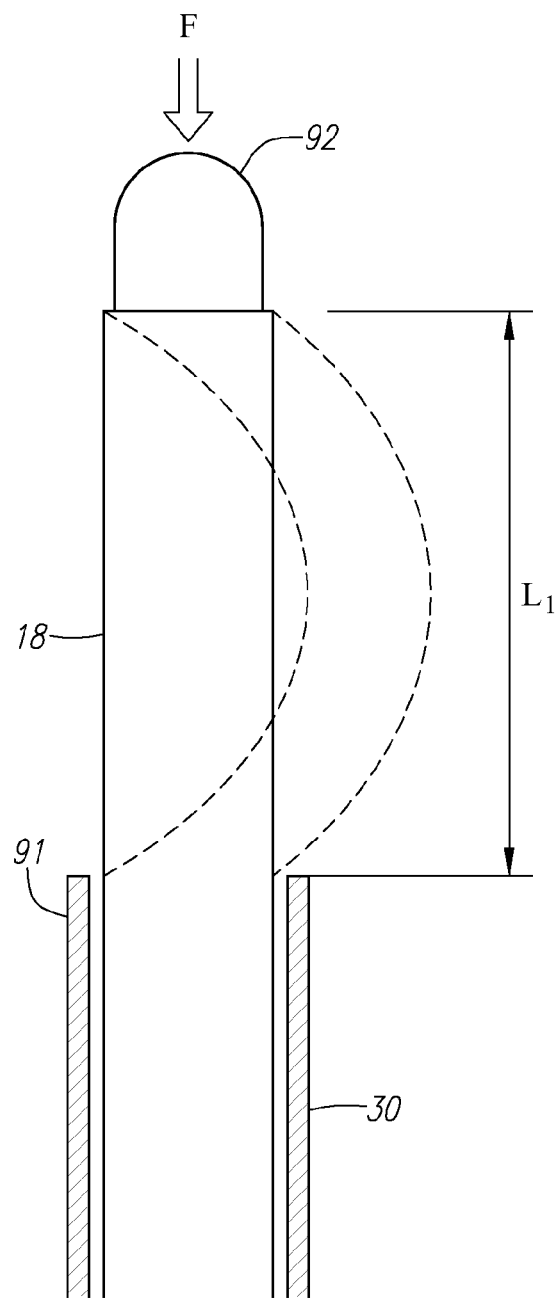
FIG. 9A illustrates a distal portion of a guide catheter extending beyond a distal end of a sheath instrument by a distance or length $L_1$ and a force F imparted on the distal tip of the guide catheter that may cause the distal portion of the guide catheter to bend or flex.

More particularly, FIG. 9A shows a length $L_1$ of the guide catheter instrument (18) that extends beyond the distal tip (91) of the sheath (18). As the distal tip (92) of the guide catheter (18) makes contact with tissue with a force F, an equal and opposite force F is imparted to the guide catheter instrument (18) (represented by arrow F). Depending upon the magnitude of the force F, a portion of the guide catheter (18), e.g., adjacent to the distal tip (92), may be caused to bend, flex or buckle under the force F, thereby reducing the force exerted on the tissue.

Figure 9B:
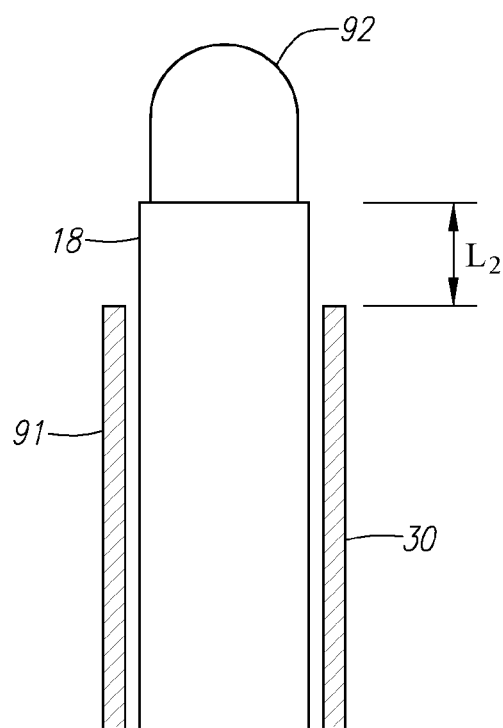
FIG. 9B illustrates a distal portion of a guide catheter extending beyond a distal end of a sheath instrument by a distance or length $L_2$ that is less than the length $L_1$ shown in FIG. 9A.

FIG. 9B illustrates a guide catheter (18) that extends a shorter length $L_2$ beyond the distal tip (91) of the sheath (30). In this example, when the distal tip (92) of the guide catheter (18) makes contact with tissue with the same force F, the shorter length L2 reduces or eliminates flexing since the distal portion of the guide catheter (18) is reinforced by the distal end of the stiffer sheath (30), resulting in a larger force F that is applied to the tissue due to less flexing.

In one system (S), motors of the instrument driver (16) are controlled to robotically control and manipulate catheter instruments (18). The amount of current supplied to the motor is proportionally related to the amount of torque generated by the motors and catheter (18) insertion force is proportional to the motor torque. Thus, the motor current is proportional to the insertion force. If the motors are driven by the same amount of current regardless of how far the guide catheter (18) extends out from the sheath (30), the force imparted on the tissue at the contact point may differ based on length L. For example, if a high motor current causes a high insertion force for a guide catheter (30) extending length $L_1$, the catheter (30) may dissipate a portion of that force due to flexing or bending. However, when the guide catheter (30) extends a much smaller length $L_2$, it may not yield, and the insertion force is not attenuated. In one embodiment, a kinematic model of the instrument configuration may be utilized, in concert with sensed motor torques at driveshafts within the instrument driver, to calculate, or "back out", the loads and vectors thereof that are theoretically applied to the distal end of the instrument, or other portion of the instrument in contact with an external load-applying structure.

In one embodiment, a system (S) may be configured to generate a visual or audible warning message to a user, control element or processor indicating that corrective action is required and/or to indicate a possibility of high insertion forces exerted to tissue at the distal tip (92). In one embodiment, a warning message is displayed when length L is less than a minimum length $L_{min}$ and/or the motor current I is greater than $I_{max}$. For example, the minimum length $L_{min}$ may be about 30 mm or less, and the maximum motor current $I_{max}$ may be about 250 mA or higher current levels. In cases in which the length or motor current exceeds these pre-determined values, the operator may adjust the motor current accordingly or proceed carefully to avoid causing injury. This type of force indication message may be useful for instrument driver (16) that do not have force sensing capabilities.

Figure 9C:
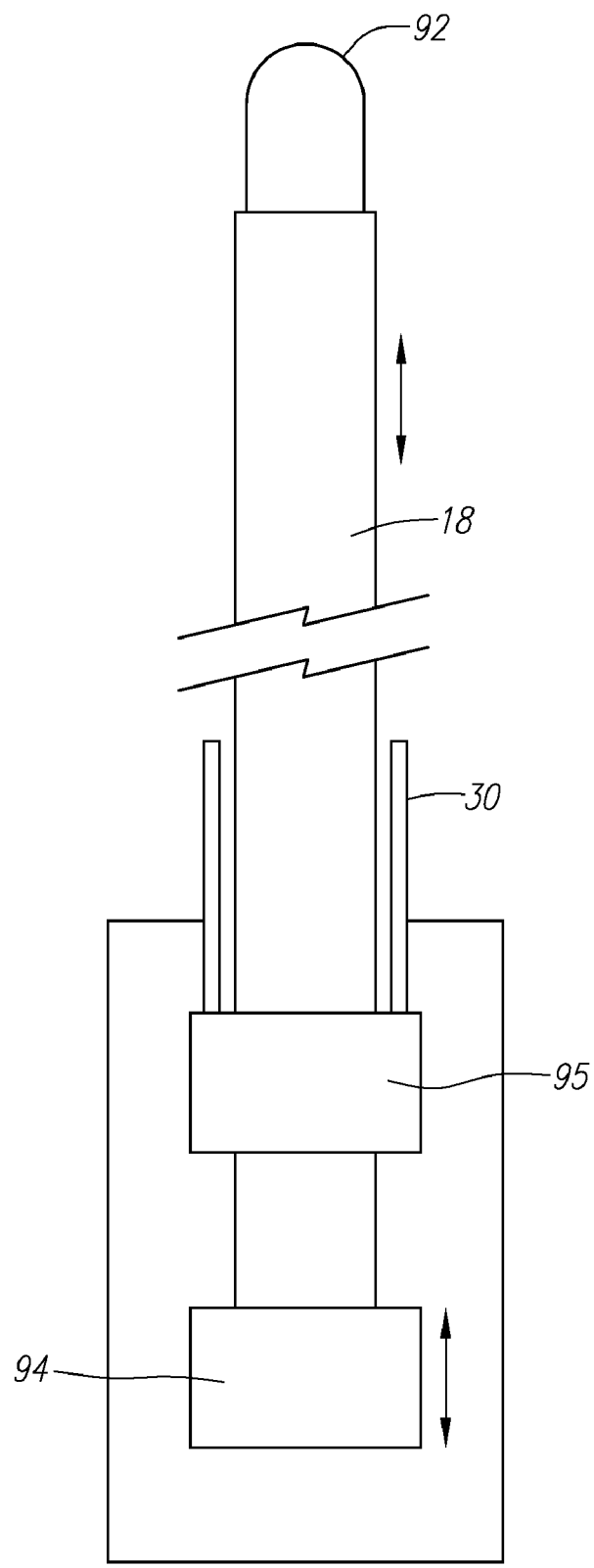
FIG. 9C illustrates sheath and catheter components shown in FIGS. 9A-B and a guide catheter control assembly for dithering the guide catheter.

One manner in which insertion or contact forces may be determined is by dithering the guide catheter (18). The guide catheter (18) may be dithered independently from the sheath (30). As illustrated in FIG. 9C, one manner in which dithering may be implemented is by use of a dithering system that includes a control subassembly (94) that is associated with the guide catheter (18). The subassembly (94) or components thereof are cycled or oscillated forwards and backwards to impart a dithering motion to the guide catheter (18).

Figure 9D:
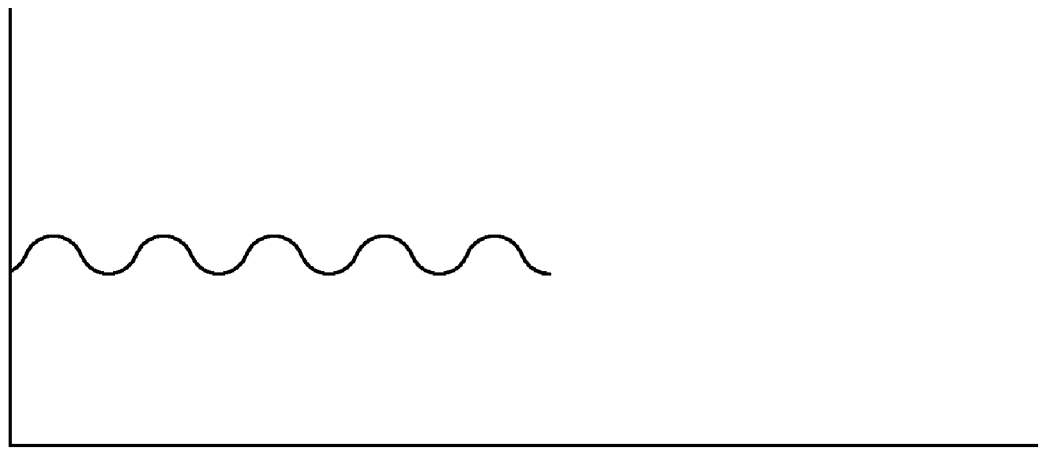
FIG. 9D is a graph illustrating ambient resistive forces as the guide catheter is dithered in an open space without contacting tissue.
Figure 9E:
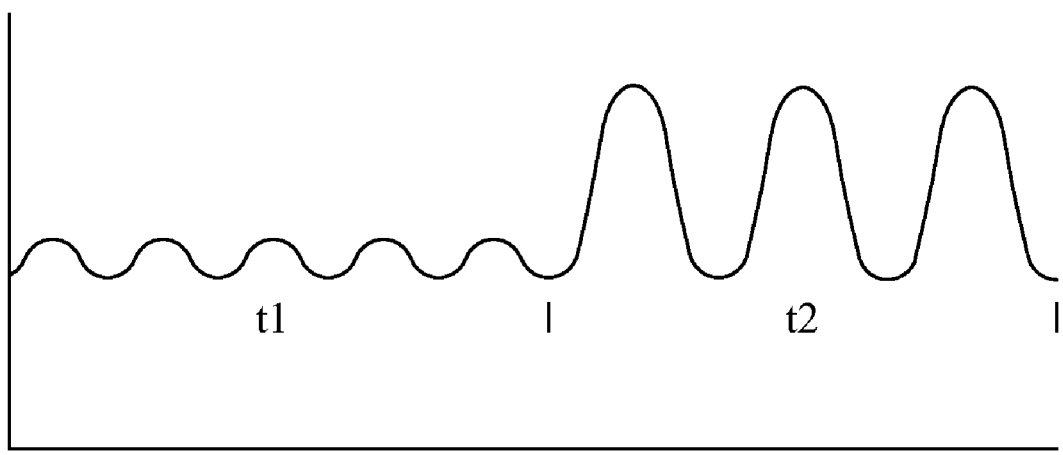
FIG. 9E is a graph illustrating force readings after a time period t1 when the guide catheter and the distal tip register only ambient resistive forces and a time period t2 when the distal tip of the guide catheter contacts tissue.

FIG. 9D is a graph that illustrates ambient resistive forces as the guide catheter (18) is dithered in an open space without contacting tissue. These ambient resistive forces may be due to friction between the guide catheter (18) and the sheath (30). Ambient resistive forces may also be due to friction between the guide catheter (18) and fluid (e.g., blood, etc.) in the cavity where the guide catheter (18) is applied. FIG. 9E is a graph that illustrates force readings after a time period t1 when the guide catheter (18) and the distal tip (92) registered only ambient resistive forces, and after a time period t2 when the distal tip (92) contacts tissue. As shown in FIG. 9E, peak force readings at t2 are higher than peak force readings at t1.

Figure 9F:
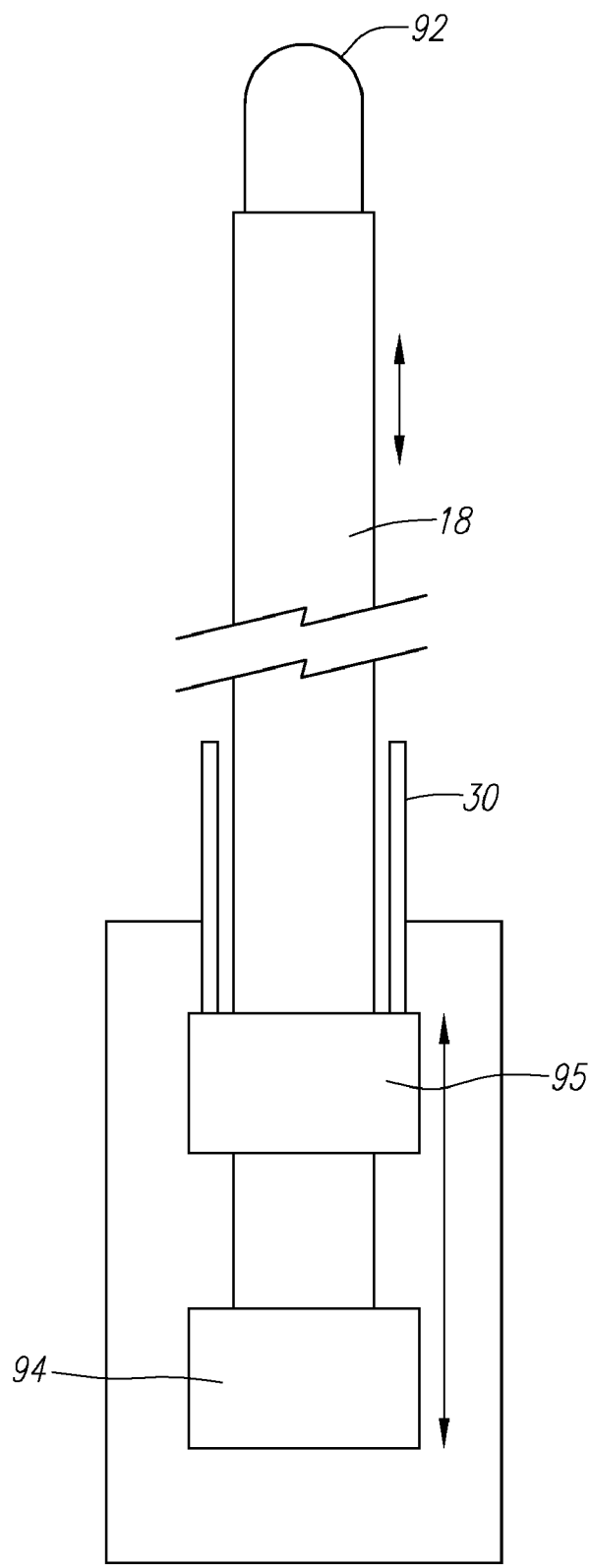
FIG. 9F illustrates system constructed according to one embodiment that includes catheter and sheath control subassemblies for dithering the guide catheter, the distal tip of the guide catheter, and the sheath in unison.

In this example, the actual tissue contact force may be determined by subtracting the force readings acquired at t2 from the force readings acquired at t1. In another embodiment, as illustrated in FIG. 9F, the guide catheter (18), sheath (30), and distal tip (92) may be controlled to dither in unison by cycling or oscillating the catheter control subassembly (94) and a sheath control subassembly (95) together.

Figure 9G:
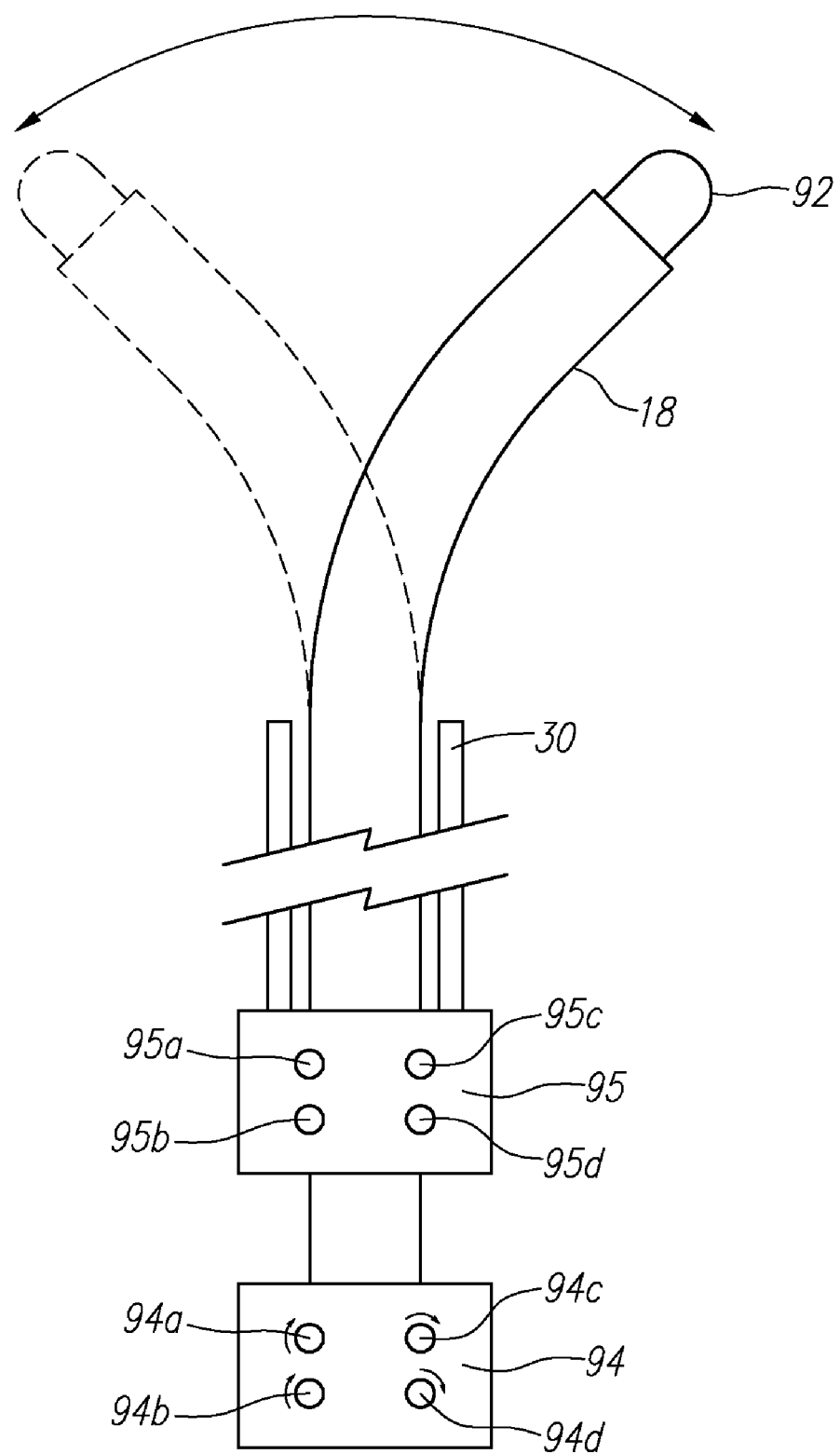
FIG. 9G illustrates a system constructed according to one embodiment that includes subassembly controllers for dithering or oscillating the distal tip of a guide catheter laterally.

Referring to FIG. 9G, in another embodiment, the distal tip (92) may be controlled to dither or oscillate laterally, and lateral contact forces may be determined in a manner similar to that described above. In this embodiment, the distal tip (92) may be oscillated laterally by oscillating the guide catheter (18) by tensioning various combinations of guide catheter control elements or pull wires (72a-d) at the guide control subassembly (94) and associated controllers (94a-d). Similarly, the distal tip (92) may be oscillated laterally by oscillating the sheath (30) by tensioning various combinations of sheath catheter control elements or pull wires (e.g., one or more of four pull wires 81a-d) at the sheath control subassembly (95) and associated controllers (95a-d).

Mouse Instinctive Driving

As described above, a primary three-dimensional (3D) input device for the robotic catheter systems (S) is the master input device (MID) (12). According to another embodiment, a two-dimensional (2D) input device is manipulated by an operator within a 2D plane for instinctive driving of a catheter instrument (18) or other working instrument within a limited range of motion within a two dimensional plane which, e.g., may be selected by a camera, or within a 3D space. In one embodiment, the two dimensional input device is manipulated to control the position of the catheter instrument (18). In a further embodiment, the two dimensional input device is manipulated to control an orientation of a catheter instrument (18). According to another embodiment, the two dimensional input device is manipulated to control the position and the orientation of a catheter instrument (18).

In one embodiment, the two dimensional input device is a mouse that is operably coupled to one or more controllers or processors of the system (S) shown in FIG. 1. Mouse components are well known and are not described in further detail. In one embodiment, an operator can manipulate the mouse such that movement of the mouse in a two dimensional plane results in movement of a catheter instrument (18) in a three dimensional space using appropriate software, hardware and/or control elements. While a mouse may not provide for the same degree of motion that can be achieved using a MID (12), use of a mouse advantageously allows for minute adjustments if it is desirable to maintain the position of the catheter instrument (18) within a particular plane in space, e.g., in embodiments in which 2D mouse motion is translated into 2D catheter instrument (18) motion.

In one embodiment the mouse can be used to select a tool or instrument to be driven. The selection mechanism of one embodiment comprises creating a ray trace between a selected point and the current mouse position. An object intersecting the ray trace in a two dimensional region bound by the camera viewport is determined to be the selected object to be manipulated.

Figure 10A:
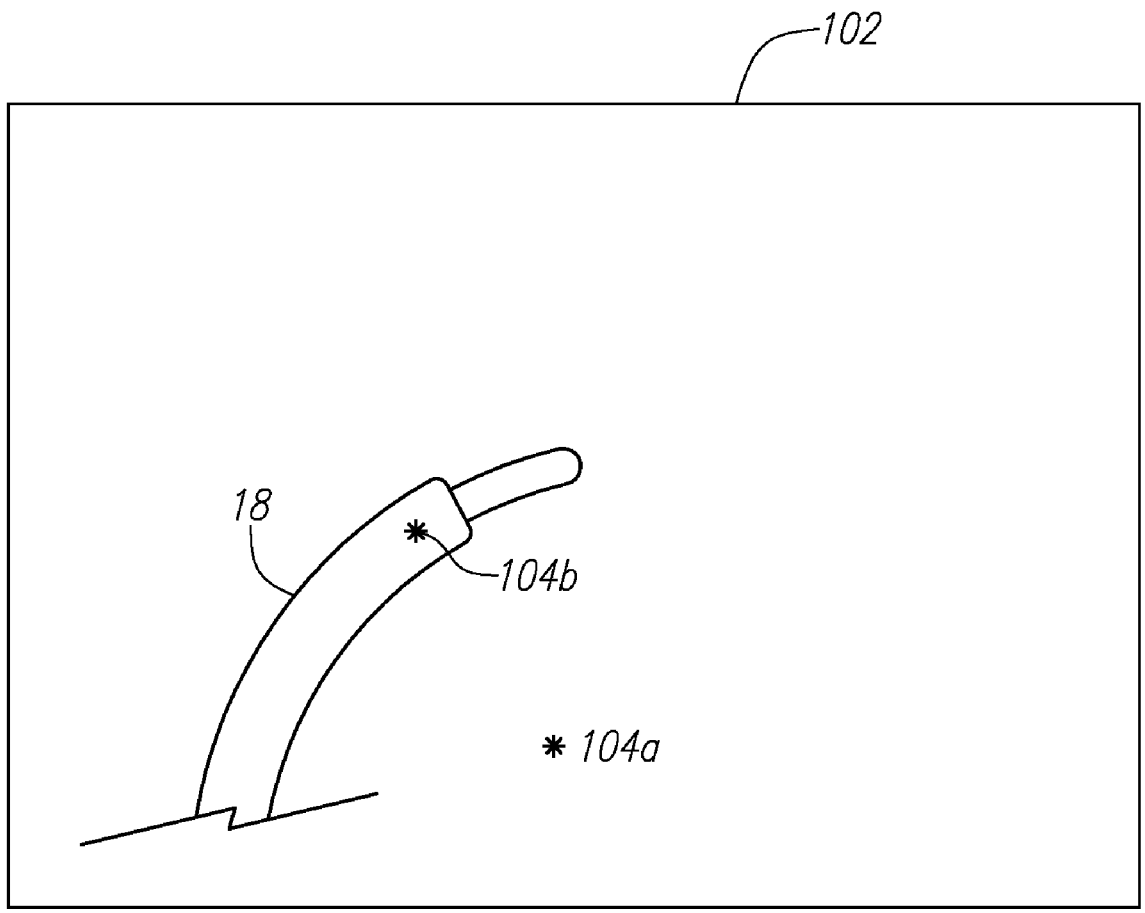
FIG. 10A illustrates a system for driving a catheter or other instrument with a mouse and how a mouse is used to select and move the instrument.
Figure 10B:
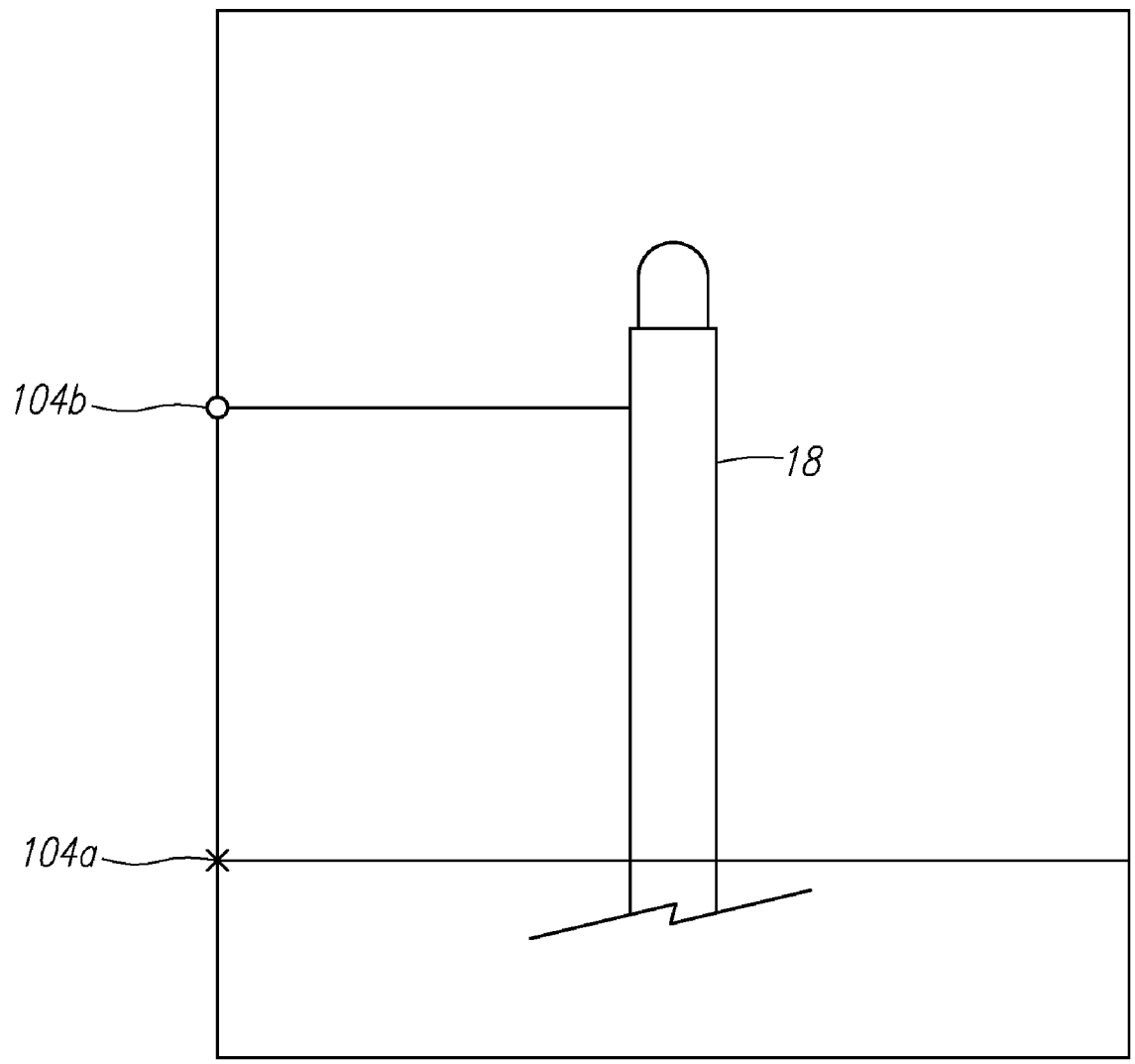
FIG. 10B is a side view representation further illustrating points selected by a mouse and trace lines that miss and intersect with the catheter.

More particularly, referring to FIG. 10A, a display (102), such as a computer monitor, display a three dimensional object, such as a catheter (18). The catheter (18) may be displayed within or relative to a three dimensional space, such as a body cavity or organ, e.g., a chamber of a patient's heart. An operator uses the mouse to move a control point around the display (102) and clicks the mouse at a point (or clicks a point or position) on the display (102) as indicated by point (104a). Utilizing appropriate software and/or hardware, a trace line is projected into the three dimensional space of the body cavity. In the illustrated example, the trace line of point (104a) fails to interact or intersect with the catheter (18).

As shown in FIG. 10A, the operator selects or clicks another point on the display (102), such as point (104b). In this example, the project or trace line of point (104b) interacts or intersects the catheter (18) at a point near the distal portion of catheter (18). FIG. 110B illustrates a side view representation illustrating point (104a) and where the trace line of point (104a) "misses" the catheter (18). Further illustrated in FIG. 10B, the trace line projected from point (104b) interacts or intersects with the catheter (18) near the distal portion of the catheter (18). Once the computer software recognizes that the trace line intersects with the catheter (18), e.g., based on laser reflections, ultrasound reflections, etc.), movement of the catheter (18) can now be made by a mouse or other 2D input control device that is operably coupled to the system (S), such as a trackball, light pen, etc. In embodiments in which movement is within a two dimensional plane, the plane of motion may be selected using a camera.

The mouse may now control the x-y movements of the catheter (18) at the interaction or intersection point of the catheter (18) by simple translation movements of the mouse. In addition, the operator may use a keyboard and the mouse to define rotational movements of the catheter (18) at the interaction or intersection point of the catheter (18). Thus, three dimensional movement of an object is advantageously achieved by substantially two dimensional movements or commands from a mouse or another known two dimensional input device. Although embodiments are described with reference to a mouse, in other embodiments, the two dimensional input devices may be a trackball and a light pen or other suitable two dimensional input device.

Reachability/Viewability

Another alternative embodiment is directed to methods and systems for assessing reachability and viewability at a particular location. More particularly, embodiments advantageously assess locations within the body that can be reached by a catheter instrument (18) of the system (S), as well as assessing the viewability or field of view at a particular location that can be reached by the catheter instrument (18). This ability is particularly significant since the field of view at a particular location may not be desirable even if it is reachable. Thus, embodiments advantageously assess field of view at reachable locations in order to provide more meaningful surgical planning and results.

For example, in the context of cardiac surgery utilizing an intracardiac (ICE) catheter. During the planning stage, an operator can determine offline before a procedure where a catheter should be driven to provide for a desired field of view that allows a region of interest to be scanned. Alternatively, a previously acquired CT model may be registered and fused with real time ultrasound data during a surgical procedure. During use, embodiments allow the ICE catheter to be driven to a position within the heart with a desired or optimum field of view for scanning of, e.g., the left atrium, or another internal tissue or segment thereof that is of interest.

Figure 11:
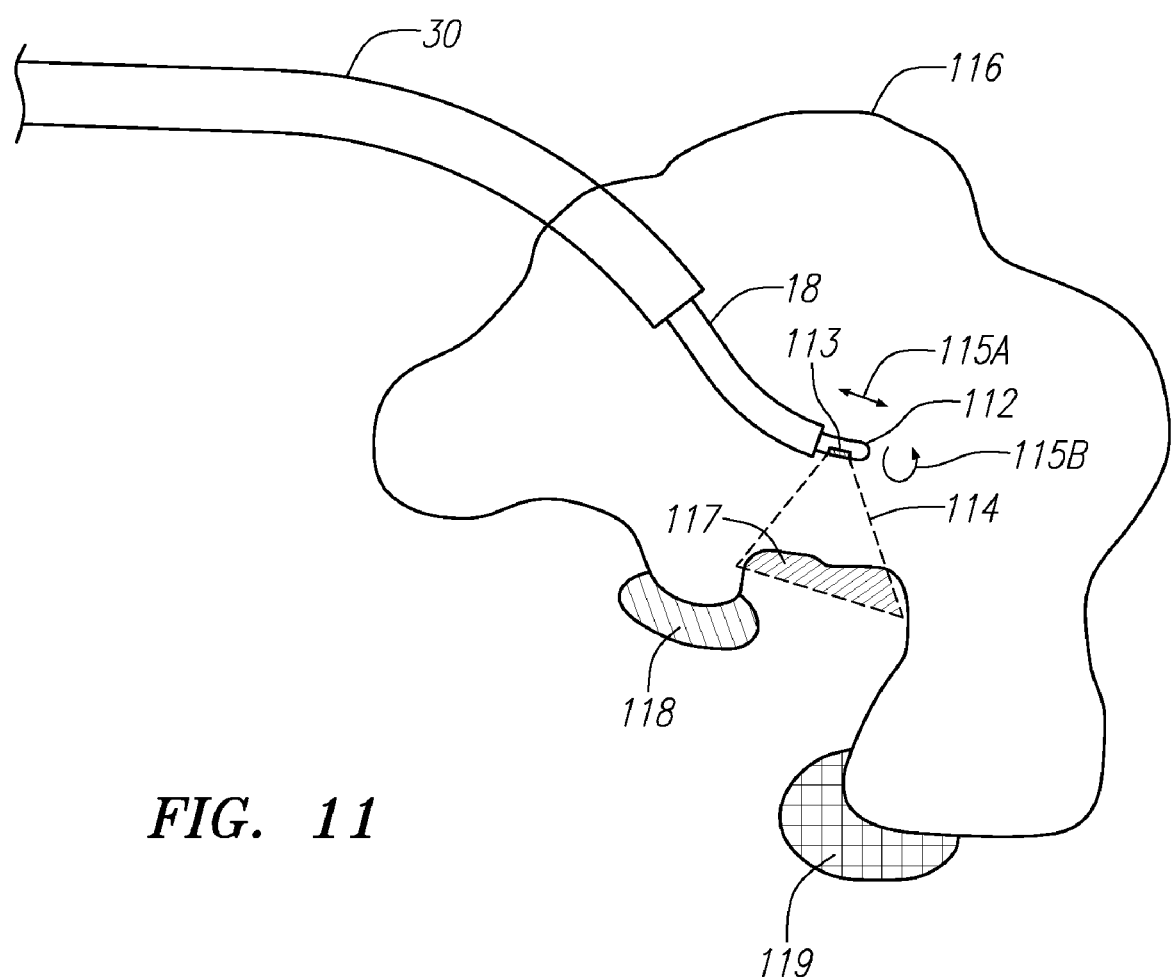
FIG. 11 illustrates assessing reachability and viewability or field of view according to one embodiment.

Referring to FIG. 11, in one embodiment, a robotic medical system includes an outer sheath 100 with a working lumen, and an inner guide catheter 111 extending through the sheath lumen, with a distal end portion of the guide catheter 111 extending out a distal end opening of the sheath 110 in an anatomic workspace 116 in a body. An intracardiac (ICE) ultrasound imaging catheter 112 is positioned in a working lumen of the guide catheter 111, with a distal end portion of the ICE catheter 112 extending out a distal end opening of the guide catheter 111. The ICE catheter 112 may be extended out of, and retracted into, respectively, the distal end opening in the guide catheter 111, as indicated by arrow 115A, and may be rotated about its longitudinal axis, as indicated by arrow 115B, such that a transducer array 113 on the ICE catheter 113 is positionable within the anatomic workspace 116 to capture ultrasound images within a field of view 114 of the array 113. The depicted ICE catheter 112 comprises a substantially linear array 113 defining a field of view 114 having a substantially trapezoidal shape; ICE catheters with such configurations are available from suppliers such as the Ultrasound division of Siemens AG under the tradename AcuNav™. In other embodiments, substantially circular/disc shaped fields of view may be created utilizing an ultrasound transducer configuration which may be rotated along with a portion of the ICE catheter with a drive shaft, as in the ICE catheters available from Boston Scientific, or utilizing multiple ultrasound transducers placed circumferentially around a catheter body, as in the ultrasound imaging catheters available from Volcano Corporation. For illustrative purposes, FIG. 11 depicts a linear array, AcuNav™ type configuration—but each of the aforementioned other configurations may be similarly employed.

Depending on factors such as the anatomical boundaries and tissue structures in the anatomical workspace 116, and the relative positions and prior trajectories of the sheath 110, guide catheter 111, and ICE catheter 112 within the workspace 116, the system controller (not shown in FIG. 11) can model the potential relative movement the respective sheath 110, guide 111 and ICE catheter 112, and thus the potential movement of the field of view 114 of the transducer array 113 within the work space 116. In particular, certain tissue walls and/or structures within the anatomic workspace 116 can be readily imaged (or "viewable") by the ICE transducer 113 without requiring anything more than a relatively simple repositioning of the respective sheath 110, guide 111 and ICE catheter 112, respectively, such as tissue structure 117 in FIG. 11. Other tissue wall locations and/or structures may be viewable, but only by more complicated maneuvering techniques, including iterative movements of one or more of the sheath 110, guide 111 and/or ICE catheter 112, respectively, in order to position the transducer 113 and field of view 114, such as tissue structure 118 in FIG. 11. Still further tissue wall locations and/or structures may be difficult or impossible to capture within the field of view 114 of the ICE transducer 113 without a major repositioning of the collective instruments (sheath 110, guide 111, ICE catheter 112), if at all.

This "ICE viewability" analysis may be useful for both pre-operative planning, and during a procedure, wherein the robotic system controller is configured to determine a respective reach of the distal end portion of the ICE catheter 112, and thus the potential fields of view 114 that may be captured by the transducer array 113 within the anatomical workspace 116, based at least in part upon a planned or a present relative position of the respective sheath, guide and ICE catheter 112 instruments. By way of non-limiting examples, the controller may determine the viewability of the various anatomic wall surfaces and/or tissue structures based at least in part on a kinematic model of one or both of the sheath and guide catheter instruments 110 and 111. Further, the controller may display the possible field of views, viewable tissue walls and/or structures, or both, overlaying an image of the anatomic workspace on a display associated with the robotic system, wherein the image of the anatomic workspace is obtained from a model of the workspace, from an imaging system, or both.

By way of further non-limiting example, the viewability of the tissue walls and structures may be displayed in a manner that indicates which areas of the workspace may be viewed by the transducer array 113 of the ICE catheter 112 from its present position (e.g., by rotating the ICE catheter 113 about its longitudinal axis, as indicated by arrow 115B in FIG. 11), and which areas cannot be viewed by the transducer array 113 from the present position of the ICE catheter 112. Further, the viewability of the various tissue walls and structures within the workspace 116, and/or the fields of view of the transducer 114, may be displayed as a scaled gradation, e.g., including a first location zone highlighted on the display to indicate that it can be viewed by the transducer 113 from the present position of the ICE catheter 112, or by simple maneuvering, a second location zone highlighted on the display to indicate it may possibly be captured within the field of view 114 of the transducer 113 by using additional or special maneuvering of the ICE catheter 112, and a third location zone may be highlighted on the display to indicate that it cannot be viewed/imaged by the transducer array 113 from its present position without more fundamental or complicated repositioning of the respective sheath/guide and or ICE catheter instruments.

In some embodiments, in determining the viewability of the various tissue wall regions and/or structures the controller determines and causes to be displayed a relative ease or difficulty in viewing/imaging respective locations and structures in the workspace 116. The controller may also may take account a likelihood that some portion of the respective instruments 110/111/112 may get hung up into tissue or some other structure in the workspace 116 an attempted move from their respective present positions to other potential locations and positions in the anatomical workspace. By way of example, if a collision is required for the distal end portion of the ICE catheter 112 to reach a particular position or range of positions within the anatomical workspace 116 in order to provide a particular field of view 114 for the transducer array 113 when moved from its present position, the location of each such position may be highlighted or otherwise designated on the display. In one embodiment, in determining the reach of the transducer array on the distal end of the ICE catheter 112, the controller takes into account one or more of locations of sensitive tissue structures in the workspace to be avoided, locations of target tissue structures in the workspace to be reached, planned trajectories of the respective sheath, guide and ICE catheter instrument distal ends, and planned end positioned of the respective instruments.

The system of claim 32, wherein the reach of the instrument distal end portion is displayed as a scaled gradation, including at least a first location zone highlighted on the display to indicate that a collision is not required for the instrument distal end portion to reach a particular position therein when moved from its present position, a second location zone highlighted on the display to indicate that at least a portion of the instrument would collide with or deflect an adjacent tissue structure in order for the instrument distal end portion to reach a particular position therein when moved from its present position, and a third location zone highlighted on the display to indicate that it cannot be reached by the instrument distal end portion from its present position.

In one embodiment, the viewability of the tissue wall regions and/or structures in the workspace 116 are displayed as a "yes" (viewable/imagable) or "no" (not viewable/imagable), or as a numeric or other scaled gradation. In another embodiment, the controller determines and causes to be displayed a relative imaging quality of images obtained from the respective fields of view for capturing the respective tissue wall surface and/or tissue structures in the workspace 116.

Depth Indicator

A further embodiment is directed to methods and systems that utilize an optical light source, such as a laser, an infrared or light source, that projects outwardly from a distal tip of a catheter (18) or other tool to determine the distance between the light source and an object of interest or tissue wall. Embodiments are particularly useful in applications in which it is desirable to have a camera, but the limited space that is provided limits the number and sizes of cameras that may be utilized. For example, the space that is available for camera device is quite limited in endo-urological surgeries and diagnoses involving the bladder, kidneys, and lungs. In these instances, all that may be available is a monocular vision device since the limited space does not allow for a stereo camera system. As a result, it can be difficult to determine the scale of an object. Embodiments, however, advantageously enable a surgeon to determine the size of objects utilizing a small, optical device that is operable without significant movement.

For example, in one embodiment, a light beam is projected perpendicularly out the distal tip of a catheter (18) or a tool onto an area of interest. By determining the takeoff point of that and direction of that first beam, in combination with the shining of additional beams to the same area of interest, one may be able to triangulate on the depth field and to calculate the distance to the area based on how apart the shone light beams appear on the surface.

Figure 12A:
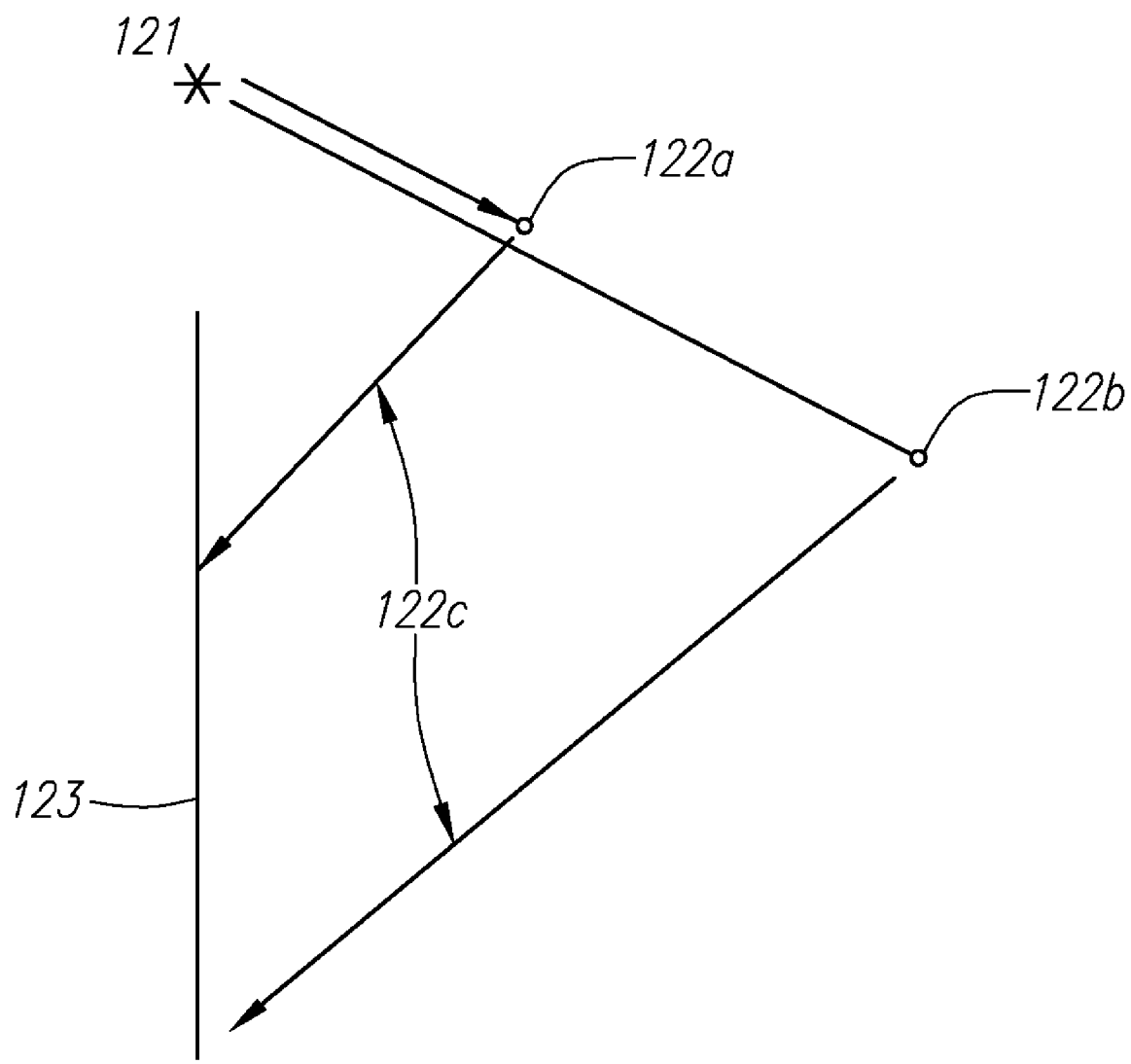
FIG. 12A illustrates a depth indication system constructed according to one embodiment that utilizes light or optical energy reflected from objects of interest.

More particularly, referring to FIG. 12A, a depth indicator system constructed according to one embodiment includes an optical or light source (121) that directs optical energy or light towards a first object of interest (122a) and a second object of interest (122b). Light emitted by the light source (121) is reflected from the objects of interest (122a, 122b) and the reflected light (122c) is captured or detected by a sensor (123). Based on the geometry of the light path from the light source (121) to the objects of interest (122a, 122b), the reflected light (122c) paths from the first and second objects (122a, 122b) to the sensor (123), the distance between the light source (121) and the first object of interest (122a), and the distance between the light source (121) and the second object of interest (122b) may be determined based on the known positions of the light source (121) and the sensor (123). According to one embodiment, the optical or light source (121) is a laser. In a further embodiment, the source (121) is an infrared source that emits infrared energy, and the sensor is configured to detect reflected infrared energy.

Figure 12B:
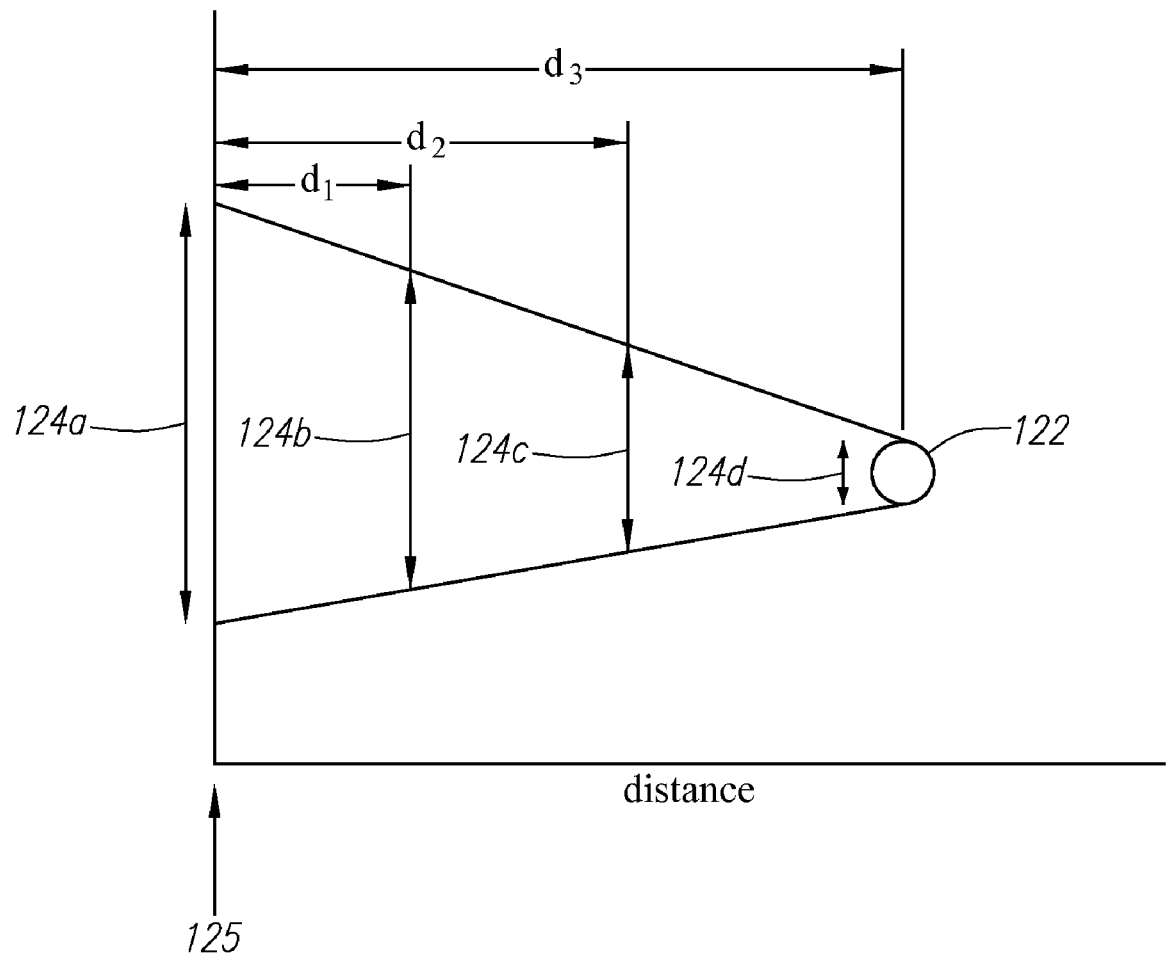
FIG. 12B illustrates a depth indication system constructed according to another embodiment that is based on the size of an image of the object relative to a reference or image capturing device and the number of pixels required to define the object.

Referring to FIG. 12B, in a system constructed according to another embodiment, actual sizes of objects of interest may be determined based on the number of pixels that define the object of interest and the distance or depth of the object from a reference point (125) (e.g., an image capturing device). For example, an object of known size may be calibrated at various depths or distances. As illustrated in FIG. 12B, an object (122) that is positioned directly in front of the image capturing device (125) will appear very large, as indicated by the height of the image (124a). However, if the object (122) is positioned farther away, e.g., at a distance d1 relative to the image capturing device (125), then the resulting image (124b) is smaller. Similarly, as the object (122) is positioned even farther away, e.g., at a distance d2 from the image capturing device (125), then the resulting image (124c) is even smaller. Moreover, if the object (122) is positioned even farther away from the image capturing device (125), then the resulting image (125d) is even smaller.

Accordingly, as the image (124) becomes smaller, the number of pixels required to define the object (122) is also smaller. Therefore, by determining the depth or distance of an object (122) relative to a reference point (125), and measuring the number of pixels required to define the image (124) of the object (122), the actual size of the object (122) can be determined based on the calibrated information. As such, although an object (122) may appear to be the same size on a display as provided by an image capturing device (125), the actual size of the object (122) may differ due to the depths or distances of the object (122) from the image capturing device (125). Embodiments advantageously utilize this structural configuration and optical relationships to enable use of small cameras in limited spaces to assess distances and sizes of objects or tissue of interest, e.g. as part of a diagnosis or treatment of kidney stones, the bladder, the lungs and other organs and tissues in which limited space may be available.

Stereovision

According to a further alternative embodiment, systems and methods are directed to implementing stereovision utilizing two cameras in a geometrically-efficient configuration particularly useful in situations in which the physical space for cameras and instruments in general is limited.

Figure 13A:
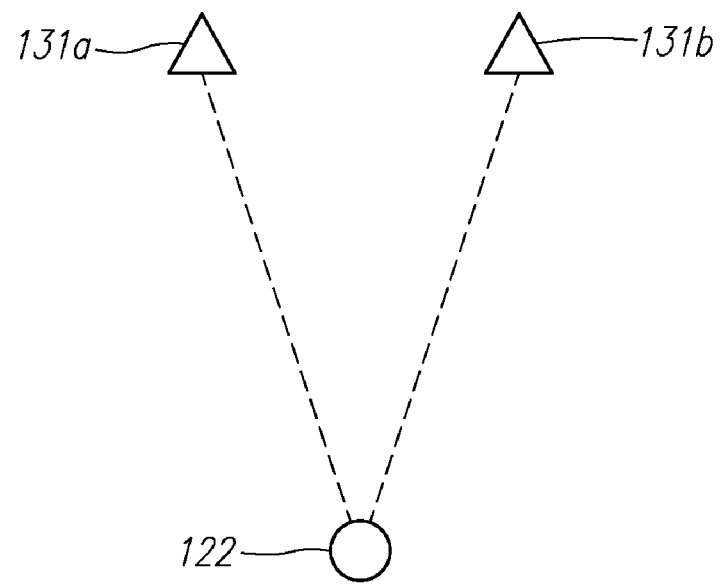
FIG. 13A illustrates a stereovision apparatus constructed according to one embodiment that includes a high resolution camera or imaging device and a low resolution camera or imaging device.

Referring to FIG. 13A, in one embodiment, a stereovision apparatus constructed according to one embodiment includes two cameras (131a, 131b). The first camera 131a may a relatively high quality camera, e.g. having a resolution of about 64×480 pixels, and the second camera 131b is advantageously a lower quality camera having a lower resolution, e.g. about 16×120 pixels, which may be configured to consume less space than camera configured to capture higher-resolution images. According to one embodiment, the cameras (131a, 131b) are attached to or components of respective endoscopes or other elongate instruments. Thus, embodiments are structured in contrast to known devices that use two high quality cameras or two cameras having substantially similar and high resolutions.

With the embodiment shown in FIG. 13A, the first and second cameras (131a, 131b) are used to acquire a stereoscopic image of the object 122. However, embodiments that utilize a first, higher resolution camera in concert with a second, lower resolution camera are still able to provide benefits of stereoscopy while reducing the size or profile of the overall apparatus and reducing the costs of the stereoscopic imaging instrument configuration.

One manner in which the system shown in FIG. 13A may be utilized is to acquire images with both cameras (131a, 131b), and then merge or fuse the acquired images together to form a stereoscopic image, which is lower quality compared to a typical stereoscopic image acquired with two high quality cameras. For this purpose, according to one embodiment, images acquired by the lower quality camera (131b) may be intentionally undersampled, and images acquired by the higher quality camera (131a) may be acquired at a normal rate. Thus, embodiments provide a stereoscopic image and depth information in applications which, for example, would otherwise be suitable for only a single camera and provide a monocular image that does not provide depth information since embodiments are able to generate a stereoscopic image (albeit a lower quality stereoscopic image) while reducing the size of components of the system used for this purpose.

Figure 13B:
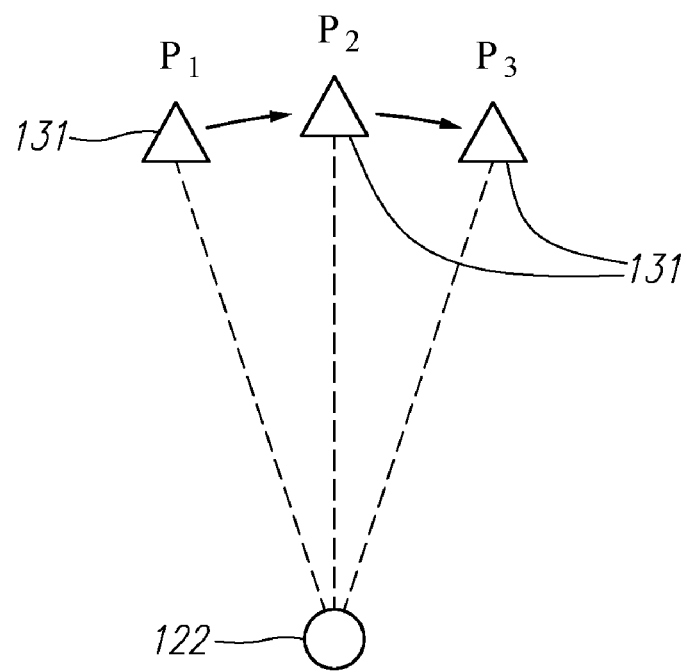
FIG. 13B illustrates a method of acquiring images from a single camera to form a stereoscopic image according to another embodiment.

Referring to FIG. 13B, in another embodiment, stereoscopic images may be acquired by using a single camera (131) to capture images from more than one position, and time multiplexing the resulting images to gain benefits of stereoscopy for an image set captured over a window of time. That is, as illustrated in FIG. 13B, one camera (131) is multiplexed in a short period of time over different locations or positions (P1, P2, P3) over time, thereby capturing images of the object 1202 from different positions. The images acquired at different times at different locations may then be fused or merged together to form a stereoscopic image of the object (122).

Figure 13C:
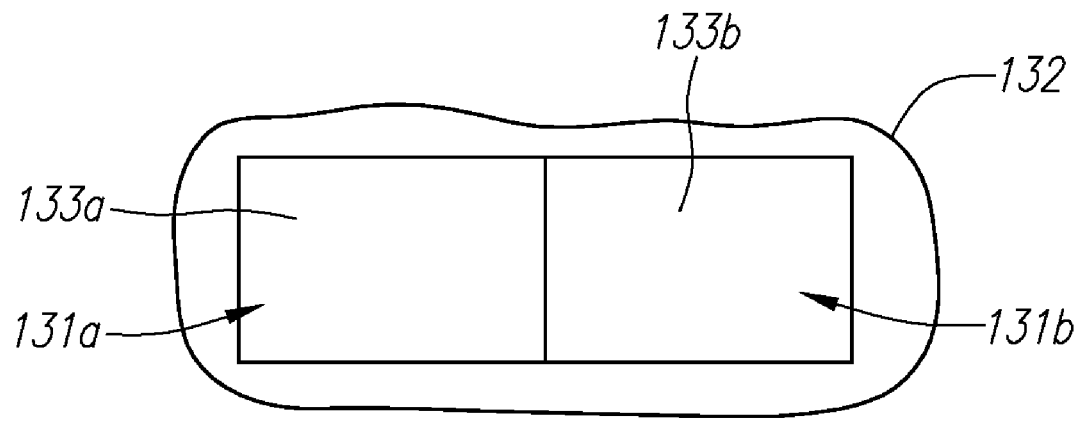
FIG. 13C illustrates a stereoscopic camera system constructed according to another embodiment that includes endoscopes having high and low resolution cameras and a lens.
Figure 13D:
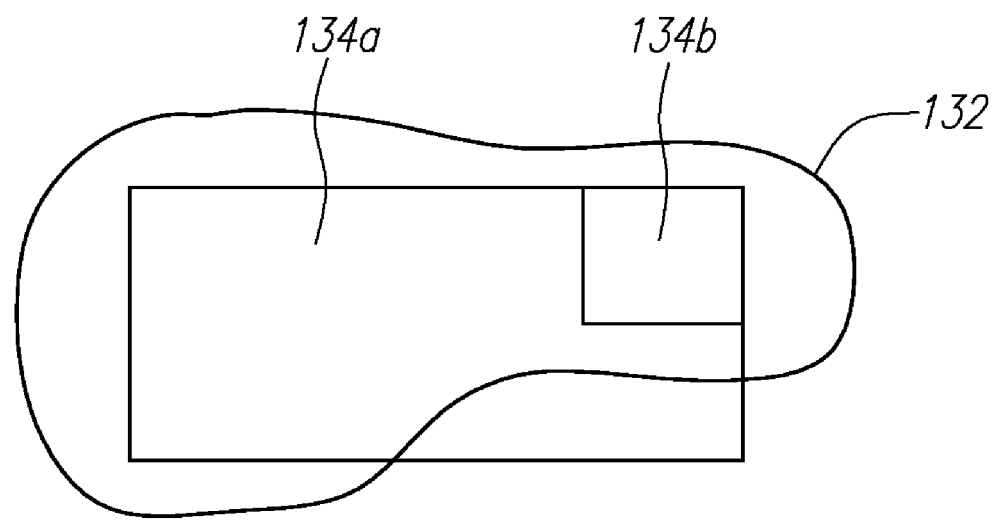
FIG. 13D illustrates a stereoscopic camera system constructed according to another embodiment includes high and low resolution endoscopes and a lens.

In another embodiment, a two-camera stereoscopic system may include components that are combined together. As illustrated in FIG. 13C, a stereoscopic camera system may include endoscopes (133a, 133b) that include respective high resolution and low resolution cameras (131a, 131b), and an image capturing objective or lens (132). Referring to FIG. 13D, a stereoscopic camera system constructed according to another embodiment includes a high resolution scope (134a), a low resolution scope (134b), and an objective or lens (132). In other words, in one embodiment, to achieve the aforementioned functional benefits of having one high-resolution image capture device and one low-resolution image capture device, and also to utilize the geometric and cost efficiencies of having a single image capture device, such as a charge coupled device ("CCD") chip, a majority of the pixels of a CCD chip may be directed and lensed for capturing images from one perspective, while a minority of the pixels of the same CCD chip may be directed and lensed for capturing images from another perspective; the lenses may comprises a single construct overlaid upon the CCD chip; thus a single CCD chip may be utilized to provide benefits of stereoscopy in a very cost and geometry efficient package.

While various embodiments haven been described herein, such disclosure is provided for purposes explanation and illustration. Further, various embodiments may be used in combination with other embodiments. Additionally, although certain embodiments are described with reference to particular dimensions or parameters, it should be understood that these dimensions and parameters are provided for purposes of explanation, and that other dimensions and parameters may also be utilized.

Embodiments and instruments of robotic systems (S) may be used in various minimally invasive surgical procedures that involve different types of tissue including heart, bladder and lung tissue, for example. Depending on the procedure, distal portions of various instruments may not be easily visible to the naked eye. Various imaging modalities including magnetic resonance (MR), ultrasound, computer tomography (CT), X-ray, fluoroscopy, etc. may used for this purpose to visualize the surgical procedure and location of instruments. Further, it may be desirable to know the precise location of a given catheter instrument and/or working tool at any given moment to avoid undesirable contacts or movements. For this purpose, one or more localization techniques that are presently available may be applied to any of the apparatuses and methods disclosed above. For example, one or more localization coils may be built into a flexible catheter instrument. In other implementations, a localization technique using radio-opaque markers may be used with embodiments of the present invention. Similarly, a fiber optic Bragg sensing fiber may be built into the sidewall of a catheter instrument to sense position and temperature. Embodiments may also be implemented in systems that include a plurality of sensors, including those for sensing patient vitals, temperature, pressure, fluid flow, force, etc., may be combined with the various embodiments of flexible catheters and distal orientation platforms disclosed herein.

Embodiments of flexible catheters and other related instruments used in a robotic surgical system may be made of various materials, including materials and associated techniques that are the same as or similar to those described in U.S. patent application Ser. No. 11/176,598, the contents of which were previously incorporated by reference. For example, suitable materials may include stainless steel, copper, aluminum, nickel-titanium alloy (Nitinol), Flexinol® (available from Toki of Japan), titanium, platinum, iridium, tungsten, nickel-chromium, silver, gold, and combinations thereof, may be used to manufacture parts such as control elements, control cables, spine elements, gears, plates, ball units, wires, springs, electrodes, thermocouples, etc. Similarly, non-metallic materials including, but not limited to, polypropylene, polyurethane (Pebax®), nylon, polyethylene, polycarbonate, Delrin®, polyester, Kevlar®, carbon, ceramic, silicone, Kapton® polyimide, Teflon® coating, polytetrafluoroethylene (PTFE), plastic (non-porous or porous), latex, polymer, etc. may be used to make the various parts of a catheter and other system components.

Further, although embodiments are describe with reference to a catheter in the form of a guide catheter and working instruments, it is also contemplated that one or more lumens of catheters may be used to deliver fluids such as saline, water, carbon dioxide, nitrogen, helium, for example, in a gaseous or liquid state, to the distal tip. Furthermore, it is contemplated that some embodiments may be implemented with a open loop or closed loop cooling system wherein a fluid is passed through one or more lumens in the sidewall of the catheter instrument to cool the catheter or a tool at the distal tip.

Further, although various embodiments are described with reference to a sheath and/or a guide catheter having four control elements or pull wires, it may be desirable to have a guide instrument with different numbers of control elements, e.g., less than four control elements. Further, although certain embodiments are described with reference to a guide catheter in combination with a steerable sheath, other embodiments may be implemented in systems that include a guide catheter (or other catheter) in combination with a prebent, unsteerable sheath, or perhaps with no sheath at all. Further, embodiments described above may be utilized with manually or robotically steerable instruments, such as those described in U.S. patent application Ser. No. 11/481,433, previously incorporated herein by reference. The instrument driver can be configured and adapted to meet the needs of different system and instrument configurations, e.g., using different numbers of motors and gearboxes for driving control elements, or variation in the configuration for actuating a given control element interface assembly, and associated variation in the tensioning mechanism and number of control element pulleys associated with the pertinent control element interface assembly (one pulley and one cable per control element interface assembly, two pulleys and two cables per control element interface assembly, slotted, split carriage, and winged split carriage embodiments, various tensioning embodiments, etc).

Accordingly, embodiments are intended to cover alternatives, modifications, and equivalents that fall within the scope of the claims.

What is claimed is:

1. A robotic instrument system, comprising:
an elongate flexible instrument;
a controller configured to selectively actuate one or more motors operably coupled to the instrument to thereby selectively move a distal end portion of the instrument within an anatomical workspace in which the instrument is located; and
an imaging device coupled to the distal end portion of the instrument and configured to acquire images of tissue regions and structures located within in a field of view,
wherein the controller is further configured to determine which tissue regions and structures within the anatomical workspace are locatable within the field of view of the imaging device based, at least in part, upon a present relative position of the instrument distal end portion.

2. The system of claim 1, wherein the controller determines a reach of the instrument distal end portion and of the field of view of the imaging device based, at least in part, on a kinematic model of the instrument.

3. The system of claim 1, further comprising a display in communication with the controller, wherein the controller displays the determined reach of the field of view of the imaging device on the display.

4. The system of claim 1, further comprising a display in communication with the controller, wherein the controller displays the tissue regions and structures in the anatomical workspace determined to be within reach of the field of view of the imaging device on the display.

5. The system of claim 4, wherein the controller displays the tissue regions and structures in the anatomical workspace determined to be within reach of the field of view of the imaging device overlaying an image of the anatomic workspace.

6. The system of claim 5, wherein the image of the anatomic workspace is obtained from a model of the workspace, from an imaging system, or both.

7. The system of claim 1, wherein the imaging device comprises an intracardiac echocardiography catheter positioned in a working lumen of the instrument.

8. The system of claim 1, wherein the tissue regions and structures in the anatomical workspace determined to be within reach of the field of view of the imaging device reach of the instrument distal end portion is displayed in a manner that indicates which tissue regions and structures of the workspace may be captured within the field of view of the imaging device from its present position, and which tissue regions and structures of the workspace may not be captured within the field of view of the imaging device from its present position.

9. The system of claim 1, wherein the tissue regions and structures in the anatomical workspace determined to be within reach of the field of view of the imaging device are displayed as a scaled gradation, including at least
- a first location zone highlighted on the display to indicate the tissue regions and structures that can be captured within the field of view of the imaging device from its present position by normal maneuvering of the instrument,
- a second location zone highlighted on the display to indicate the tissue regions and structures that can be captured within the field of view of the imaging device from its present position by using with additional or special maneuvering of the instrument, and
- a third location zone highlighted on the display to indicate the tissue regions and structures that cannot be captured within the field of view of the imaging device from its present position regardless of maneuvering of the instrument.

10. The system of claim 1, wherein the reach of the imaging device field of view is displayed as a "yes" or "no", or as a numeric or other scaled gradation.

11. The system of claim 1, wherein in determining the reach of the imaging device field of view, the controller determines and causes to be displayed a relative ease or difficulty in reaching respective locations and positions in the workspace.

12. The system of claim 1, wherein in determining the reach of the imaging device field of view, the controller takes into account one or more of locations of sensitive tissue structures in the workspace to be avoided, locations of target tissue structures in the workspace to be reached, planned trajectories of the instrument distal end portion, and planned end points of the instrument distal end portion and of the imaging device.

* * * * *